United States Patent
Bonutti

(10) Patent No.: US 10,065,009 B2
(45) Date of Patent: *Sep. 4, 2018

(54) METHODS FOR POSITIONING A MEDICAL DEVICE IN A RESPIRATORY SYSTEM

(71) Applicant: P Tech, LLC, Effingham, IL (US)

(72) Inventor: Peter M. Bonutti, Effingham, IL (US)

(73) Assignee: P Tech, LLC, Effingham, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/256,629

(22) Filed: Apr. 18, 2014

(65) Prior Publication Data

US 2014/0228679 A1 Aug. 14, 2014

Related U.S. Application Data

(63) Continuation of application No. 13/048,163, filed on Mar. 15, 2011, now abandoned, which is a (Continued)

(51) Int. Cl.
*A61B 5/06* (2006.01)
*A61M 16/04* (2006.01)
(Continued)

(52) U.S. Cl.
CPC ......... *A61M 16/0488* (2013.01); *A61B 1/005* (2013.01); *A61B 1/00082* (2013.01); (Continued)

(58) Field of Classification Search
CPC ........... A61B 5/06; A61B 8/461; A61B 5/065; A61B 8/4254; A61B 1/015; A61B 1/0676;
(Continued)

(56) References Cited

U.S. PATENT DOCUMENTS 2,463,149 A 3/1949 Caine
2,541,402 A 2/1951 Caine
(Continued)

OTHER PUBLICATIONS

Senyei et al., "Magnetic Guidance of Drug-Carrying Microspheres", J. Appl. Phys. 49(6):3578-3582 (U.S.A. 1978).
(Continued)

*Primary Examiner* — Jonathan Cwern
(74) *Attorney, Agent, or Firm* — Senniger Powers LLP

(57) ABSTRACT

A method for positioning a medical device in a respiratory system is provided. The method includes providing a medical device system including a positioning apparatus having a body section and an upper section, the upper section slidably coupled to the body section, a flexible guide rod, a visible light source, and a medical device for treating the patient slidably receivable on the flexible guide rod. The method also includes inserting the flexible guide rod into a treatment portion of a respiratory system, emitting visible light from the visible light source, visually observing, outside the patient's body, the emitted visible light, and slidably moving the medical device distally along the flexible guide rod toward the distal end of the flexible guide rod to a selected position relative to the distal end of the flexible guide rod and within said treatment portion of the respiratory system of the patient's body.

20 Claims, 14 Drawing Sheets

Related U.S. Application Data continuation of application No. 12/431,835, filed on Apr. 29, 2009, now abandoned, which is a continuation of application No. 10/990,870, filed on Nov. 17, 2004, now abandoned, which is a continuation of application No. 09/728,553, filed on Dec. 2, 2000, now Pat. No. 6,820,614.

(51) Int. Cl.

| | |
|---|---|
| *A61B 8/08* | (2006.01) |
| *A61B 8/12* | (2006.01) |
| *A61B 8/00* | (2006.01) |
| *A61M 25/01* | (2006.01) |
| *A61B 1/00* | (2006.01) |
| *A61B 1/005* | (2006.01) |
| *A61B 1/015* | (2006.01) |
| *A61B 1/06* | (2006.01) |
| *A61B 1/07* | (2006.01) |
| *A61M 25/09* | (2006.01) |
| *A61M 25/02* | (2006.01) |
| *A61M 25/00* | (2006.01) |

(52) U.S. Cl.
CPC .......... *A61B 1/00124* (2013.01); *A61B 1/015* (2013.01); *A61B 1/0676* (2013.01); *A61B 1/0684* (2013.01); *A61B 1/07* (2013.01); *A61B 5/065* (2013.01); *A61B 8/0841* (2013.01); *A61B 8/12* (2013.01); *A61B 8/4254* (2013.01); *A61B 8/4263* (2013.01); *A61B 8/445* (2013.01); *A61B 8/461* (2013.01); *A61M 16/0411* (2014.02); *A61M 16/0434* (2013.01); *A61M 16/0495* (2014.02); *A61M 16/0497* (2013.01); *A61M 25/0102* (2013.01); *A61M 25/0108* (2013.01); *A61M 25/09* (2013.01); *A61M 2025/0008* (2013.01); *A61M 2025/022* (2013.01); *A61M 2025/091* (2013.01); *A61M 2025/09008* (2013.01); *A61M 2205/0272* (2013.01); *A61M 2205/587* (2013.01)

(58) Field of Classification Search
CPC . A61B 1/00082; A61B 1/00124; A61B 1/005; A61B 1/07; A61B 1/0684; A61B 8/445; A61B 8/4263; A61B 8/12; A61M 16/04; A61M 2025/022; A61M 16/0497; A61M 16/0488; A61M 25/09; A61M 16/0411; A61M 25/0108; A61M 25/0102; A61M 16/0434; A61M 2205/587; A61M 2205/0272; A61M 2025/09008; A61M 2025/0008; A61M 2025/091
See application file for complete search history.

(56) References Cited

U.S. PATENT DOCUMENTS

| | | | |
|---|---|---|---|
| 2,862,498 A | 12/1958 | Weekes | |
| 3,314,431 A | 4/1967 | Taricco | |
| 3,833,033 A | 9/1974 | Taricco | |
| 3,996,939 A | 12/1976 | Sheridan | |
| 4,063,561 A | 12/1977 | McKenna | |
| 4,173,228 A | 11/1979 | Van Steenwyk | |
| 4,197,855 A | 4/1980 | Lewin | |
| 4,244,362 A | 1/1981 | Anderson | |
| 4,431,005 A | 2/1984 | McCormick | |
| 4,444,185 A * | 4/1984 | Shugar ............... 128/207.29 |
| 4,445,501 A | 5/1984 | Bresier | |
| 4,567,882 A * | 2/1986 | Heller ............... 600/249 |
| 4,593,687 A | 6/1986 | Gray | |
| 4,727,872 A | 3/1988 | Hawk | |
| 4,793,327 A | 12/1988 | Frankel | |
| 4,832,020 A | 5/1989 | Augustine | |
| 4,840,172 A | 6/1989 | Augustine | |
| 4,846,153 A | 7/1989 | Berci | |
| 4,865,586 A | 9/1989 | Hedberg | |
| 4,905,698 A | 3/1990 | Strohl | |
| 4,913,139 A | 4/1990 | Ballew | |
| 4,943,770 A | 7/1990 | Ashley-Rollman | |
| 4,960,122 A | 10/1990 | Mizus | |
| 4,983,165 A | 1/1991 | Loiterman | |
| 5,005,573 A | 4/1991 | Buchanan | |
| 5,042,486 A | 8/1991 | Pfeiler | |
| 5,099,845 A | 3/1992 | Besz | |
| 5,127,913 A | 7/1992 | Thomas | |
| 5,197,971 A | 3/1993 | Bonutti | |
| 5,211,165 A | 5/1993 | Dumoulin | |
| 5,235,970 A | 8/1993 | Augustine | |
| 5,257,636 A | 11/1993 | White | |
| 5,259,371 A | 11/1993 | Tonrey | |
| 5,259,377 A | 11/1993 | Schroeder | |
| 5,263,478 A | 11/1993 | Davis | |
| 5,325,873 A | 7/1994 | Hirschi | |
| 5,339,805 A | 8/1994 | Parker | |
| 5,353,787 A | 10/1994 | Price | |
| 5,353,807 A | 10/1994 | DeMarco | |
| 5,375,596 A | 12/1994 | Twiss | |
| 5,386,828 A | 2/1995 | Owens | |
| 5,425,367 A | 6/1995 | Shapiro | |
| 5,437,273 A * | 8/1995 | Bates ............... A61M 16/0488 |
| | | | 128/207.14 |
| 5,469,853 A | 11/1995 | Law | |
| 5,494,035 A | 2/1996 | Leuthold | |
| 5,540,691 A | 7/1996 | Elstrom | |
| 5,558,082 A | 9/1996 | Spencer | |
| 5,560,351 A | 10/1996 | Gravenstein | |
| 5,582,165 A | 12/1996 | Bryan | |
| 5,617,857 A | 4/1997 | Chader | |
| 5,622,169 A | 4/1997 | Golden | |
| 5,622,170 A | 4/1997 | Schulz | |
| 5,638,819 A | 6/1997 | Manwaring | |
| 5,642,730 A | 7/1997 | Baran | |
| 5,694,929 A | 12/1997 | Christopher | |
| 5,711,299 A | 1/1998 | Manwaring | |
| 5,729,129 A | 3/1998 | Acker | |
| 5,749,835 A | 5/1998 | Glantz | |
| 5,762,064 A | 6/1998 | Polvani | |
| 5,779,694 A | 7/1998 | Howard | |
| 5,782,765 A | 7/1998 | Jonkman | |
| 5,785,051 A | 7/1998 | Lipscher | |
| 5,817,057 A | 10/1998 | Berenstein | |
| 5,823,992 A | 10/1998 | Salmon | |
| 5,843,153 A | 12/1998 | Johnson | |
| 5,879,306 A * | 3/1999 | Fontenot et al. ............ 600/473 |
| 5,899,860 A | 5/1999 | Pfeiffer | |
| 5,906,579 A | 5/1999 | Vander Salm | |
| 5,913,820 A | 6/1999 | Bladen | |
| 5,944,023 A | 8/1999 | Johnson | |
| 5,954,649 A | 9/1999 | Chia | |
| 5,996,582 A | 12/1999 | Turnbull | |
| 6,014,580 A | 1/2000 | Blume | |
| 6,041,775 A | 3/2000 | Century | |
| 6,067,985 A * | 5/2000 | Islava ............... A61M 16/0488 |
| | | | 128/200.26 |
| 6,078,831 A | 6/2000 | Belef | |
| 6,081,741 A * | 6/2000 | Hollis ............ 600/424 |
| 6,161,032 A | 12/2000 | Acker | |
| 6,161,537 A | 12/2000 | Gravenstein | |
| 6,173,199 B1 | 1/2001 | Gabriel | |
| 6,175,756 B1 | 1/2001 | Ferree | |
| 6,188,355 B1 | 2/2001 | Gilboa | |
| 6,226,543 B1 | 5/2001 | Gilboa | |
| 6,226,547 B1 | 5/2001 | Lockhart | |
| 6,233,477 B1 | 5/2001 | Chia | |
| 6,246,898 B1 | 6/2001 | Vesely | |
| 6,298,261 B1 | 10/2001 | Rex | |
| 6,332,089 B1 | 12/2001 | Acker | |
| 6,349,720 B1 | 2/2002 | Clark | |
| 6,380,732 B1 | 4/2002 | Gilboa | |
| 6,432,041 B1 * | 8/2002 | Taniguchi ............ A61B 1/0055 |
| | | | 600/117 |

(56) References Cited

U.S. PATENT DOCUMENTS

| | | |
|---|---|---|
| 6,522,909 B1 | 2/2003 | Garibaldi |
| 6,527,761 B1 * | 3/2003 | Soltesz et al. ............... 604/516 |
| 6,553,993 B2 | 4/2003 | Toti |
| 6,574,498 B1 | 6/2003 | Gilboa |
| 6,580,938 B1 | 6/2003 | Acker |
| 6,593,884 B1 | 7/2003 | Gilboa |
| 6,615,155 B2 | 9/2003 | Gilboa |
| 6,672,308 B1 | 1/2004 | Gaspari |
| 6,702,780 B1 | 3/2004 | Gilboa |
| 6,711,429 B1 | 3/2004 | Gilboa |
| 6,820,614 B2 | 11/2004 | Bonutti |
| 7,320,319 B2 | 1/2008 | Bonutti |
| 7,575,550 B1 | 8/2009 | Govari |
| 2005/0103333 A1 | 5/2005 | Bonutti |
| 2009/0216066 A1 | 8/2009 | Bonutti |

OTHER PUBLICATIONS

Breyer et al., Ultrasonically Marked Catheter, a Method for Positive Echographic Catheter Position and Identification, Medical and Biological Engineering and Computing, May 1984, pp. 268-271.

Final Office Action dated Jun. 4, 2015 relating to U.S. Appl. No. 14/553,094, 13 pages.

Final Office Action dated Mar. 2, 2016 relating to U.S. Appl. No. 14/553,094, 11 pages.

Non-Final Office Action dated Sep. 15, 2015 relating to U.S. Appl. No. 14/553,094, 12 pages.

Non-Final Office Action dated Aug. 15, 2016 relating to U.S. Appl. No. 15/183,437, 15 pages.

Final Office Action dated Dec. 9, 2016 relating to U.S. Appl. No. 14/553,094, 12 pages.

Final Office Action dated Nov. 1, 2016 relating to U.S. Appl. No. 15/183,437, 14 pages.

Non Final Office Action dated May 25, 2017 relating to U.S. Appl. No. 14/553,094, 11 pages.

Non Final Office Action dated May 24, 2017 relating to U.S. Appl. No. 15/183,437, 14 pages.

Final Office Action dated Aug. 1, 2017 relating to U.S. Appl. No. 14/553,094, 10 pages.

Final Office Action dated Aug. 1, 2017 relating to U.S. Appl. No. 15/183,437, 11 pages.

* cited by examiner

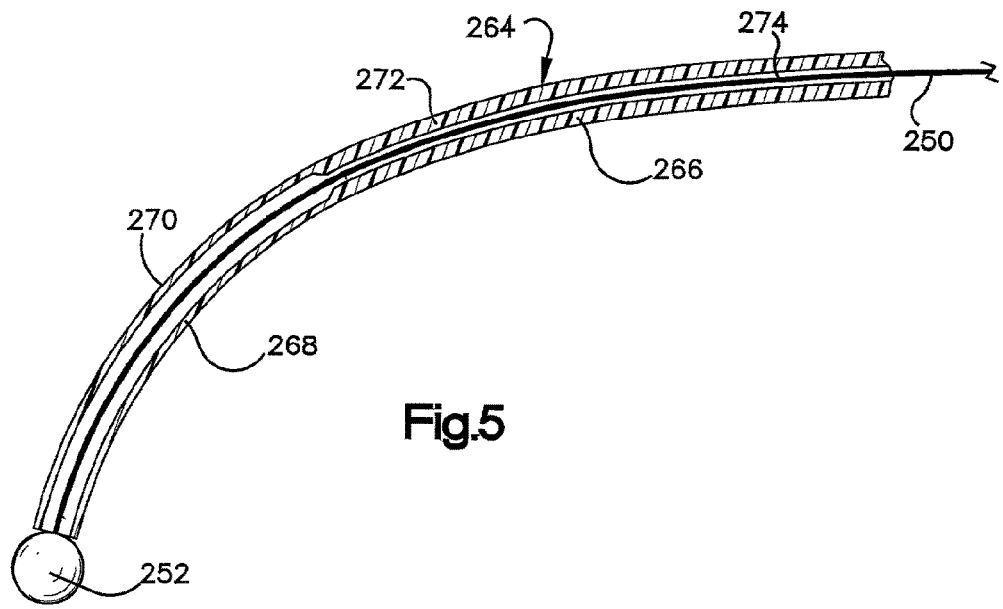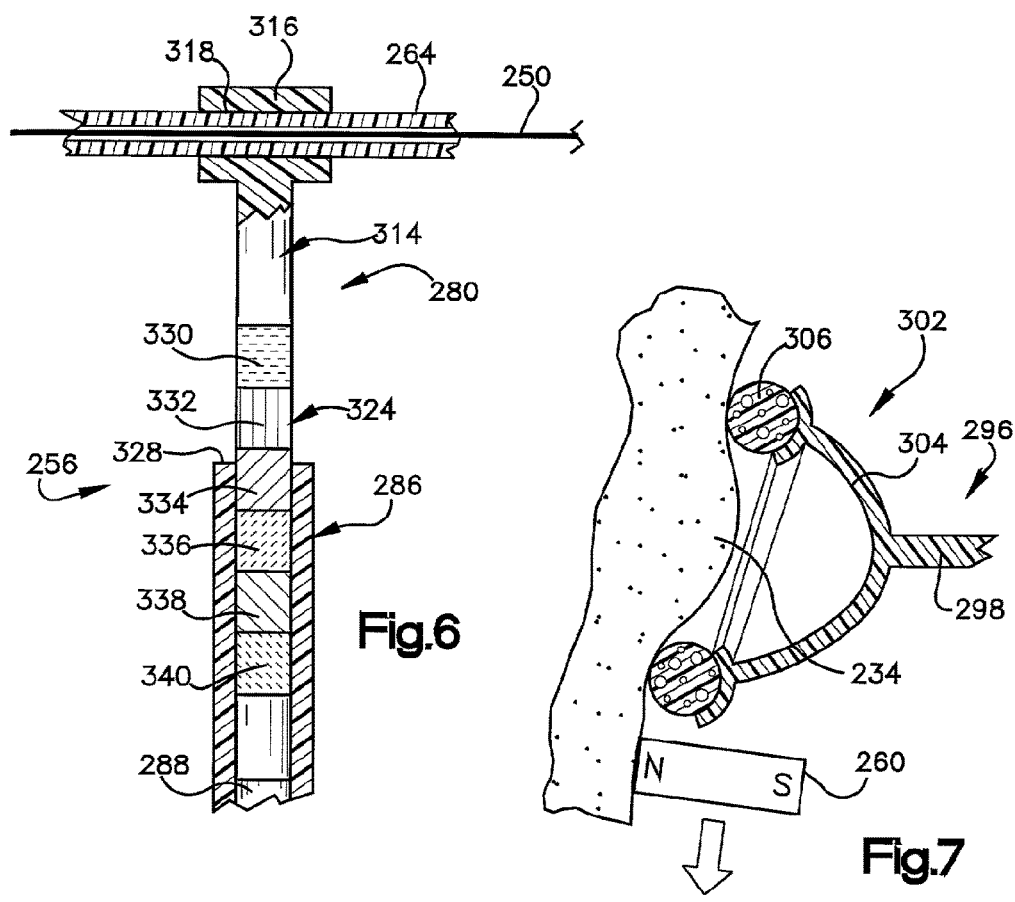

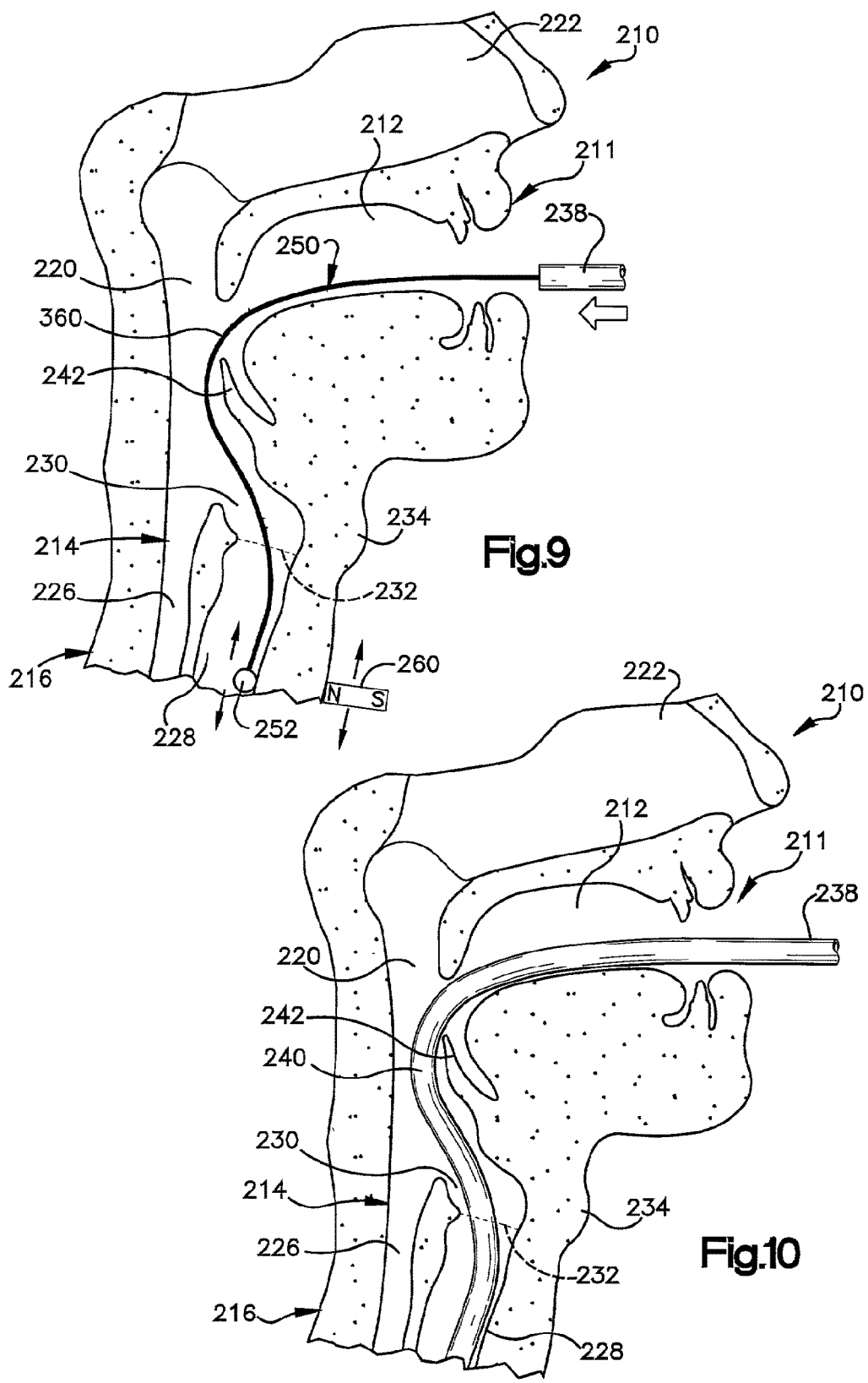

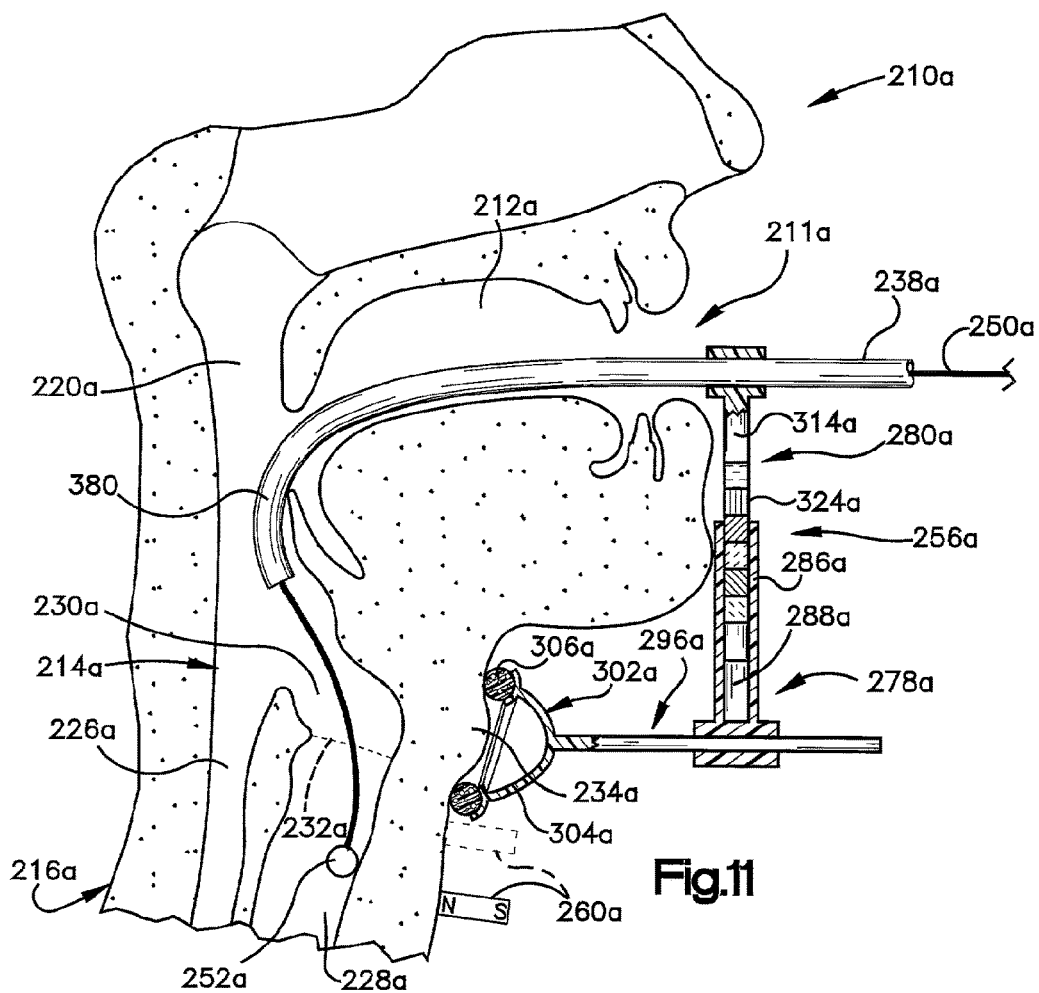

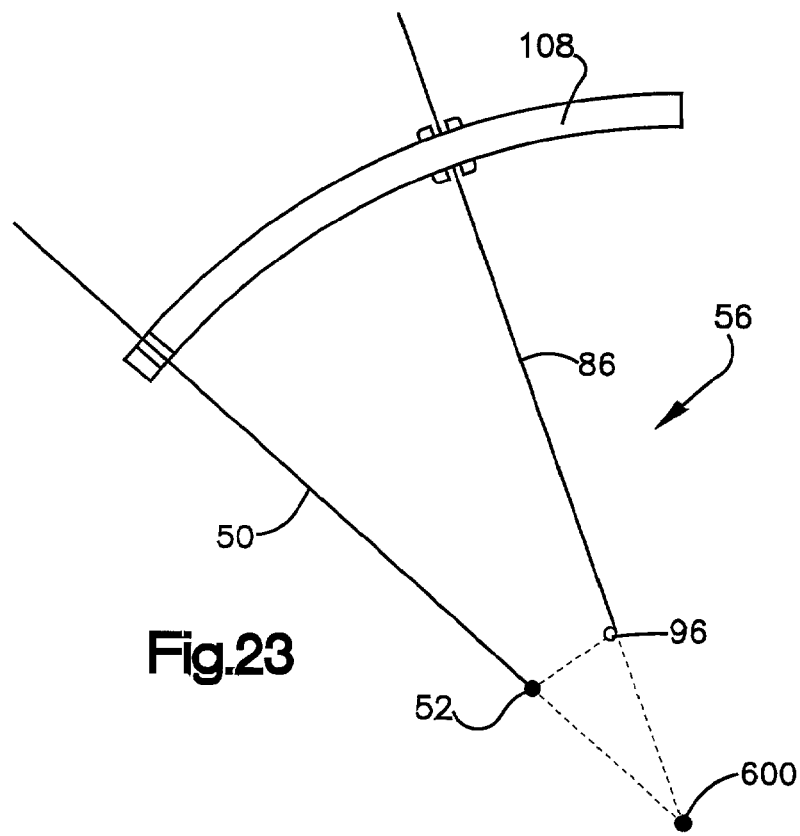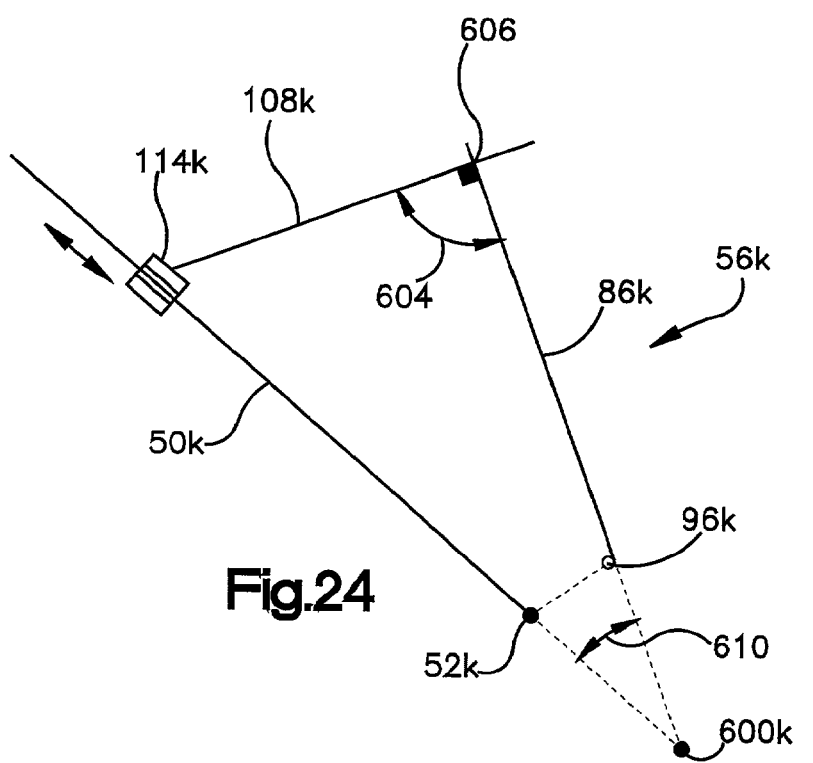

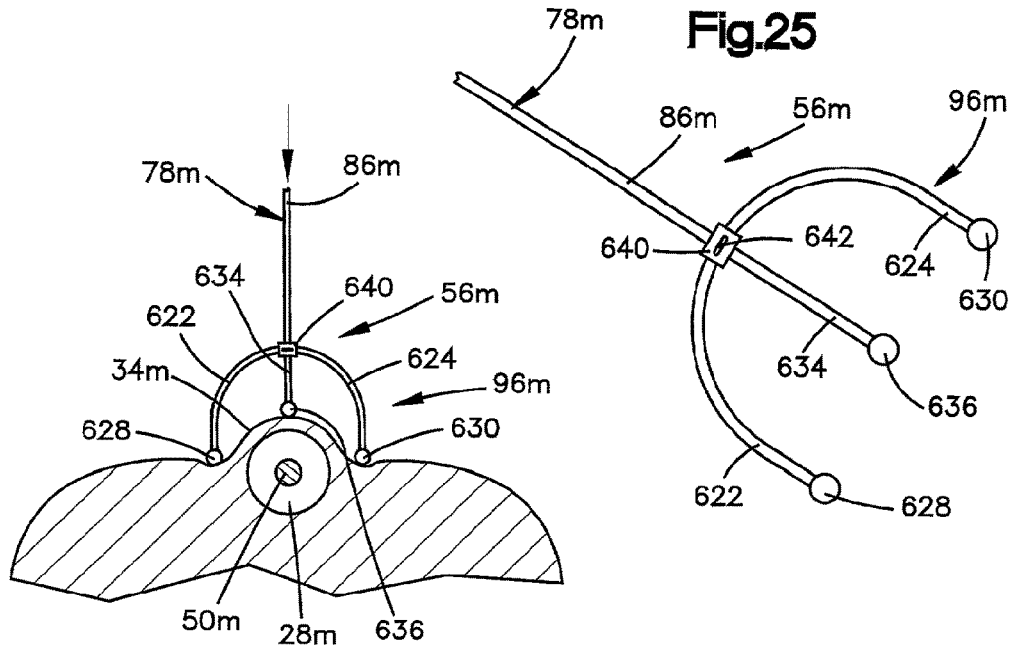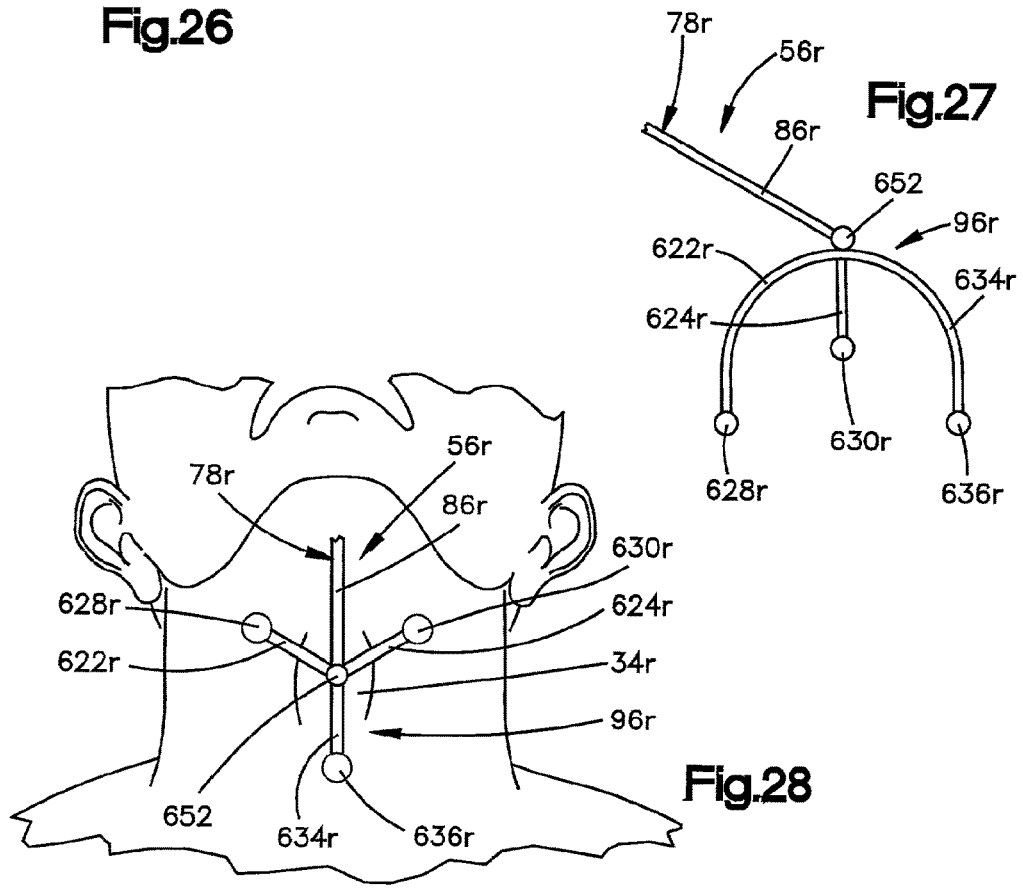

METHODS FOR POSITIONING A MEDICAL DEVICE IN A RESPIRATORY SYSTEM

CROSS-REFERENCE TO RELATED APPLICATION

This application is a continuation of U.S. patent application Ser. No. 13/048,163, filed Mar. 15, 2011, which is a continuation of U.S. patent application Ser. No. 12/431,835, filed Apr. 29, 2009, which is a continuation of U.S. patent application Ser. No. 10/990,870, filed Nov. 17, 2004, which is a continuation of U.S. patent application Ser. No. 09/728,553, filed on Dec. 2, 2000, now U.S. Pat. No. 6,820,614, the entire contents of which are incorporated by reference.

FIELD OF THE INVENTION

The present invention relates to a new and improved method and apparatus for use in tracheal intubination or other medical procedures

BACKGROUND OF THE INVENTION

Tracheal intubination has previously been utilized to provide an unobstructed air passage to a patient's lungs. Tracheal intubination is frequently done under emergency circumstances which are not optimal. It has previously been recognized that is necessary to have a tracheal tube bend around the patient's epiglottis and move from the patient's pharynx into the larynx at the upper end of the patient's trachea rather than into the patient's esophagus. However, it is difficult for a person inserting the tracheal tube to know where the leading end portion of the tracheal tube is located relative to the patient's larynx.

Various methods and devices for assisting in tracheal intubination are disclosed in U.S. Pat. Nos. 4,832,020; 4,865,586; 4,913,139; 5,353,787; 5,235,970; 5,560,351; and 5,694,929.

SUMMARY OF THE INVENTION

An improved method and apparatus for use in tracheal intubination or other medical procedure may include a positioning apparatus. When the positioning apparatus is used for tracheal intubination, the positioning apparatus is located relative to a patient's trachea by engaging a portion of the patient's body, such as the Adam's apple. A flexible guide rod may be moved relative to the positioning apparatus until a leading end portion of the guide rod has moved into the patient's trachea. A tracheal tube is slid along the guide rod into the patient's trachea.

During movement of the guide rod relative to the positioning apparatus, the guide rod may be moved through either a tubular guide member or a tracheal tube which extends through the patient's mouth into the patient's pharynx. Before beginning to move the guide rod, the distance which the guide rod is to be moved may advantageously determined. This may be done as a function of spacing between locations on the positioning apparatus. If desired, indicia may be provided on the positioning apparatus and cooperating indicia may be provided on the guide rod.

A magnet may be utilized to attract a leading end portion of the guide rod. The magnet is disposed outside of the patient's body and may be positioned adjacent to an anterior side of the trachea. Magnetic attraction between the magnet and the leading end portion of the guide rod deflects the guide rod. This steers the leading end portion of the guide rod into the entrance to the patient's trachea. A magnet may be used to steer a member relative to a patient's body tissue during performance of operations other than tracheal intubination.

In order to locate the guide rod and/or tracheal tube relative to the patient's trachea, an image of body tissue adjacent to the leading end portion of the guide rod and/or tracheal tube may be transmitted to a location outside of the patient's body. Movement of the guide rod and/or tracheal tube into the patient's trachea is interrupted when the image transmitted from the leading end portion of the guide rod or tracheal tube indicates that the leading end portion of the guide rod or tracheal tube has been moved to a desired position relative to the patient's trachea.

It is believed that transmission of an image of body tissue adjacent to the leading end portion of the tracheal tube may advantageously be performed when the tracheal tube is utilized without benefit of the positioning apparatus. However, the transmission of an image of body tissue adjacent to the leading end portion of the tracheal tube may be performed when the positioning apparatus is used in association with the tracheal tube. Positioning of the guide rod relative to the patient's trachea may also be facilitated by the transmitting of images of body tissue adjacent to a leading end portion of the guide rod.

Detectors and emitters may be utilized to detect the position of the leading end portion of the guide rod and/or the tracheal tube relative to the patient's trachea. When this is done, an emitter, such as a magnet or a light source, may be connected with a leading end portion of the guide rod and/or the tracheal tube. One or more detectors may be provided on the outside of the patient's neck to detect the output from the emitter when the guide rod and/or the tracheal tube are in a desired position relative to the patient's trachea. Alternatively, a detector may be connected with the leading end portion of a guide rod and/or tracheal tube and one or more emitters positioned relative to the outside of the patient's neck. The detector would provide an output indicating when the guide rod and/or tracheal tube is moved to a desired position relative to the patient's trachea.

During movement of the guide rod and/or tracheal tube along the patient's respiratory system and into the patient's trachea, force may be applied against the leading end portion of the guide rod and/or tracheal tube to steer the leading end portion of the guide rod and/or tracheal tube. The application of force against the leading end portion of the guide rod and/or tracheal tube may be accomplished by expanding an expandable element connected with the guide rod and/or the tracheal tube.

It should be understood that any one of the features of the present invention may be used separately or in combination with other features of the invention. It's believed that various combinations of the features, other than those disclosed herein, may advantageously be utilized and will be apparent to those skilled in the art from the description contained herein. In addition, it should be understood that features of the present invention may be used for purposes other than tracheal intubination.

BRIEF DESCRIPTION OF THE DRAWINGS

The foregoing and other features of the present invention will become more apparent upon a consideration of the following description taken in connection with the accompanying drawings wherein:

FIG. 5 is an enlarged schematic fragmentary sectional view of a portion of the apparatus of FIG. 4 and illustrating the relationship between a guide rod and a guide tube;

FIG. 6 is an enlarged schematic fragmentary sectional view of a portion of the apparatus of FIG. 4 and illustrating the relationship between the guide tube, guide rod, and a guide member in the positioning apparatus;

FIG. 7 is a schematic fragmentary sectional view illustrating a manner in which the positioning apparatus engages a patient's Adam's apple and the manner in which a magnet is moved along the outside of the neck of the patient;

FIG. 9 is a schematic fragmentary illustration of the guide rod with the positioning apparatus and guide tube of FIG. 4 removed after positioning of the guide rod relative to the patient's trachea;

FIG. 10 is a fragmentary schematic illustration, generally similar to FIG. 9, illustrating the manner in which a tracheal tube is moved along the guide rod into the patient's trachea;

FIG. 11 is a fragmentary schematic illustration, generally similar to FIG. 4, illustrating an embodiment of the apparatus in which the tracheal tube is used to guide movement of the guide rod;

FIG. 23 is a schematic illustration depicting the positioning apparatus of FIGS. 1 and 2;

FIG. 24 is a schematic illustration, generally similar to FIG. 23, illustrating another embodiment of the apparatus of FIGS. 1 and 2;

FIG. 25 is a fragmentary schematic illustration of a portion of a positioning apparatus having another embodiment of the positioning section;

FIG. 26 is a fragmentary schematic illustration depicting the relationship between the positioning section of FIG. 25 and a patient's Adam's apple during use of the positioning apparatus;

FIG. 27 is a fragmentary schematic illustration of a portion of a positioning apparatus having another embodiment of the positioning section; and FIG. 28 is a fragmentary schematic illustration depicting the relationship between the positioning section of FIG. 27 and a patient's Adam's apple during use of the positioning apparatus.

DETAILED DESCRIPTION OF THE INVENTION

General Description

Figure 1:
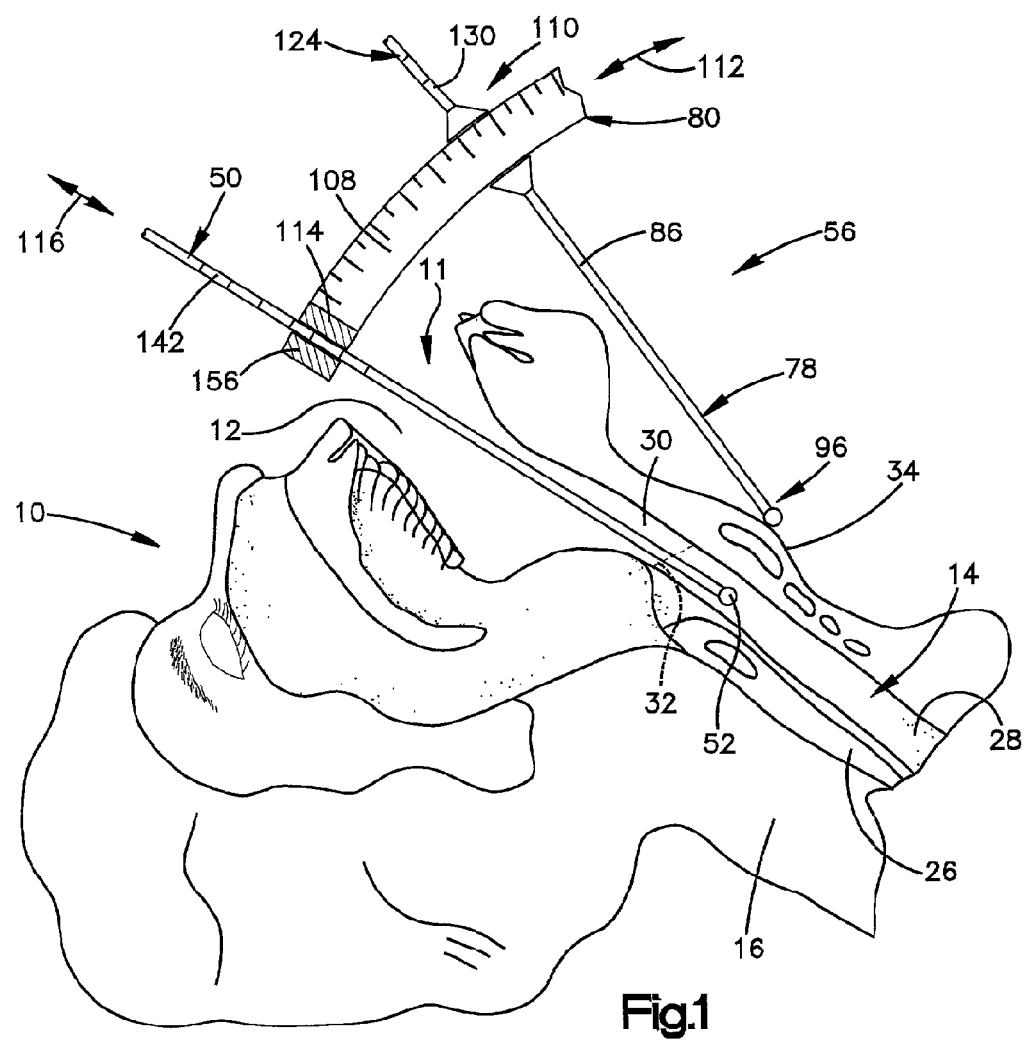
FIG. 1 is a fragmentary schematic illustration depicting the use of a positioning apparatus to position a guide rod relative to the mouth and trachea of a patient.

The present invention relates to a new and improved method and apparatus for use in tracheal intubation or other medical procedures. A portion of a patient's head 10 and respiratory system 11 has been illustrated schematically in FIG. 1. The schematicized illustration of the patient's head 10 and respiratory system 11 includes a mouth 12 which is connected with a throat 14 in a neck 16 of the patient.

A pharynx extends downward from a nasal cavity in the head 10 of the patient. The pharynx is connected with an esophagus 26 and a trachea 28 in the neck 16 of the patient. The esophagus 26 extends from the pharynx to the stomach of the patient. The trachea 28 extends from the pharynx to the bronchial tubes and lungs of the patient.

The trachea 28 (FIG. 1) has an upper end portion 30 which is referred to as the larynx. Vocal cords or folds 32 have been indicated schematically in FIG. 1 and are disposed in the larynx 30. The vocal cords 32 are adjacent to the Adam's apple 34 of the patient. The Adam's apple 34 is a laryngeal prominence formed by lamina of cartilage in the larynx.

Figure 2:
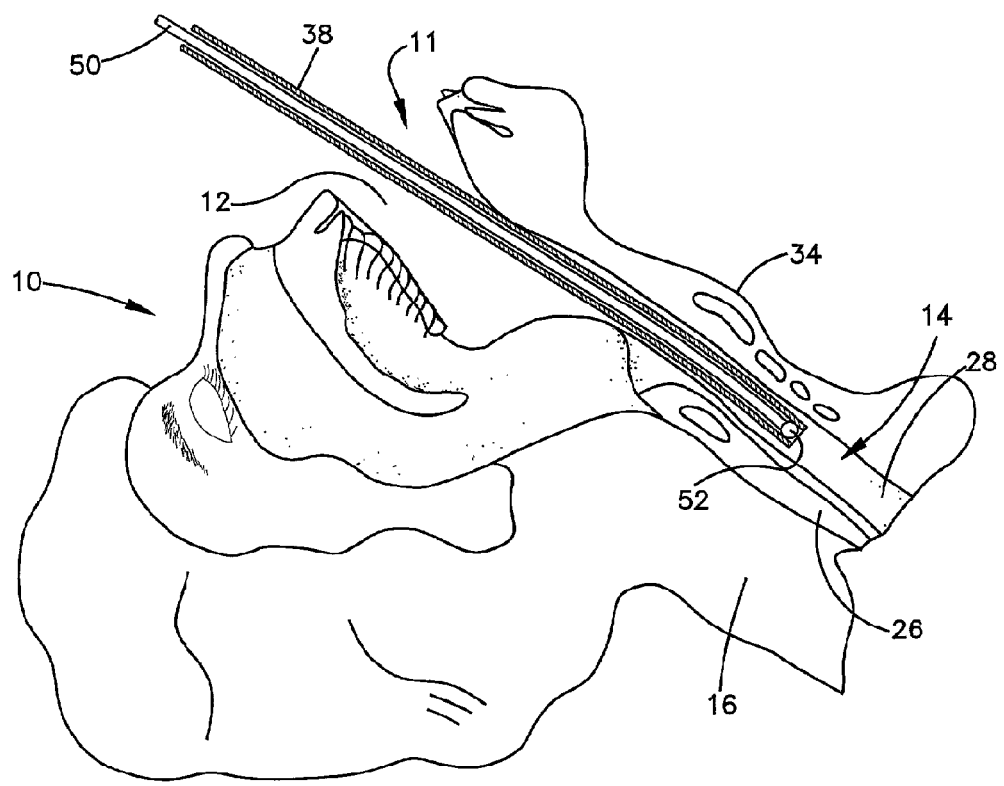
FIG. 2 a fragmentary schematic illustration depicting the manner in which a tracheal tube is moved along the guide rod of FIG. 1 into the trachea of the patient.

Opening of a passage for air from the patient's mouth to the patient's lungs may require insertion of a flexible tracheal tube 38 (FIG. 2). Movement of the flexible tracheal tube 38 from the patient's mouth 12 into the pharynx of the patient is relatively easily accomplished. However, directing the tracheal tube 38 into the patient's trachea 28 may present difficulties. This is because the tracheal tube must extend past the epiglottis into the larynx 30 at the upper end of the trachea 28. The tracheal tube 38 must not enter the esophagus 26 rather than the trachea 28. During movement of the leading end of the tracheal tube 38 through the larynx 30, it is desirable to have the tracheal tube near the central portion of the laryngeal cavity in order to minimize irritation of the vocal folds or cords 32 by the tracheal tube.

In accordance with one of the features of the present invention, a flexible guide wire or rod 50 (FIG. 1) is utilized to guide movement of the flexible tracheal tube 38 (FIG. 2) into the trachea 28. The flexible guide rod 50 has a soft generally spherical leading end portion 52. The leading end portion 52 of the guide rod 50 is formed of a resiliently compressible material which is readily deflected by engagement with the vocal cords or folds 32 and by engagement with the surface of the trachea 28. If desired, the leading end portion 52 of the guide rod 50 may be coated with a suitable lubricant to facilitate movement of the leading end portion between the vocal cords with minimum of irritation.

In accordance with another of the features of the invention, the guide wire 50 is initially positioned relative to the patient's trachea 28 with a positioning apparatus 56 (FIG. 1). The positioning apparatus 56 engages the patient's Adam's apple 34 to locate the positioning apparatus relative to the trachea 28 of the patient. In addition, the positioning apparatus 56 provides a measurement which is a function of the distance between the Adam's apple 34 and the mouth 12 of the patient. This measurement is utilized to determine the distance through which the guide rod 50 is to be moved relative to the positioning apparatus 56 as the guide rod is inserted into the trachea 28.

Positioning Apparatus

The positioning apparatus 56 has been and will be described herein in association with tracheal intubation. However, it is contemplated that the positioning apparatus 56 will be used in association with many other medical procedures where accurate positioning of an object relative to body tissue is desired. The positioning apparatus may be used in association with endoscopic, arthroscopic or fiber optic surgical procedures. It is believed that the positioning apparatus 56 will be used in conjunction with medical procedures where it is necessary to position an object at a location in a patient's body where there is only limited access.

The positioning apparatus 56 positions the guide rod 50 relative to the patient's trachea 28 during insertion of the guide rod into the patient's trachea. In addition, the positioning apparatus 56 provides an indication of the distance which the guide rod is to be moved into the patient's trachea. By using the positioning apparatus 56, a person moving the guide rod 50 into the patient's trachea 28 can know where the leading end portion 52 of the guide rod is located relative to the trachea.

The flexible guide rod 50 may be formed of either polymeric material or metal. The illustrated polymeric guide rod 50 has a relatively small diameter and is readily deflected. The guide rod 50 has a circular cross sectional configuration.

The guide rod 50 is axially movable relative to the positioning apparatus 56 under the influence of force manually applied to the portion of the guide rod disposed to the left (as viewed in FIG. 1) of the positioning apparatus 56. This force results in axial movement of the guide rod 50 relative to the positioning apparatus 56. In addition, the leading end 52 of the guide rod 50 may deflect body tissue to clear a passage for the guide rod 50.

As the guide rod 50 is moved axially relative to the positioning apparatus 56, the guide rod may be resiliently deflected by engagement with the body tissue of the patient. As the guide rod 50 is manually pushed toward the right (as viewed in FIG. 1), the leading end 52 of the guide rod moves toward the larynx 30.

The positioning apparatus 56 is used to locate the leading end portion 52 of the guide rod 50 as the guide rod moves toward the larynx 30. The positioning apparatus 56 includes a base section 78 and an arcuate upper section 80 (FIG. 1). The base section 78 engages the patient's Adam's apple 34 to locate the positioning apparatus 56 relative to the patient's trachea 28. The upper section 80 of the positioning apparatus 56 guides movement of the guide rod 50 during insertion of the guide rod into the patient's trachea 28.

The base section 78 and upper section 80 of the positioning apparatus 56 cooperate to provide a measurement of the distance between the patient's mouth 12 and the patient's Adam's apple 34. This distance will vary from patient to patient depending upon the size of the patient, the specific configuration of the head 10 of the patient, and other factors. The distance which the guide rod 50 must be moved axially into the patient's larynx 30 will vary as a function of variations in the distance between the patient's mouth 12 and the patient's Adam's apple 34. This is because the patient's Adam's apple 34 is located adjacent to the entrance to the trachea 28.

The positioning apparatus 56 can be used to position many different objects at desired locations in a patient's body. For example, the guide rod 50 or a similar member could be inserted into a patient's stomach or colon. The base section 78 of the positioning apparatus would be positioned in engagement with an exterior surface on the patient's body at a location where the leading end portion 52 of the guide rod 50 is to be moved. The upper section 80 of the positioning apparatus 56 would cooperate with the base section 78 and guide rod 50 to provide a clear indication of the location of the leading end portion 52 of the guide rod 50 relative to the patient's body tissue, for example, the patient's stomach or colon.

The base section 78 (FIG. 1) of the positioning apparatus 56 includes a tubular cylindrical body section 86. The base section 78 also includes a positioning section 96 which engages the patient's Adam's apple 34 and is supported by the body section 86. The positioning section 96 engages the patient's Adam's apple 34. Although the illustrated positioning section 96 (FIG. 1) engages only a single location on the patient's neck 16, the positioning section could be constructed so as to engage a plurality of locations on the patient's neck. For example, it may be preferred to use a positioning section 96 having two positioning fingers disposed on laterally opposite sides of the Adam's apple 34.

It is contemplated that the positioning section 96 could have many different constructions. It is believed that it may be particularly advantageous to utilize a positioning section 96 having the construction illustrated in FIGS. 25 and 26 herein. Alternatively, the positioning section 96 may have the construction illustrated in FIGS. 27 and 28 or FIGS. 4 and 7 herein if desired.

Force may be manually applied against the positioning section 96 to straighten the trachea 28 of the patient. Thus, the patient's trachea 28 may have a slight anterior bend when the patient's head 10 is in the position illustrated in FIG. 1. This slight bend can be eliminated by the manual application of minimal force to the positioning section 96. This force presses the positioning section 96 against the patient's neck.

Although it is preferred to use the patient's Adam's apple 34 to locate the positioning apparatus 56 relative to the patient's trachea 28, a different portion of the patient's body could be used to locate the positioning apparatus relative to the patient's trachea. For example, the patient's shoulders could be used. Alternatively, bones in the patient's neck 16 could be used to locate the positioning apparatus 56 relative to the patient's trachea 28. However, it is believed that it will be preferred to use the patient's Adam's apple 34 to locate the positioning apparatus 56 due to the close proximity of the patient's Adam's apple to the upper end of the patient's trachea 28.

The arcuate upper section 80 of the positioning apparatus 56 includes an arcuate member 108 which is slidably connected with the body section 86 at a connection 110. The connection 110 is movable axially along the cylindrical body section 86. The body section 86 is movable transversely to the arcuate member 108, in the manner indicated by the arrows 112 in FIG. 1. Suitable indicia, indicated by lines in FIG. 1, may be provided on the arcuate member 108 to indicate the position of the connection 110 relative to the arcuate member.

The connection 110 may include a plurality of set screws (not shown) having manually engagable flanges or arms. One of the set screws may be tightened to prevent movement between the body section 86 and the connection 110. Another set screw may be tightened to prevent movement between the arcuate member 108 and the connection 110.

When the connection 110 has been moved to a desired location along the body section 86, a set screw in the connection is tightened to hold the arcuate member 108 against axial movement along to the cylindrical body section 86. The arcuate member 108 is then moved transversely to the body section 86, that is, in the direction of the arrows 112, to position a guide section 114 in alignment with the patient's mouth 12 and trachea 28. When the tubular guide section 114 has been aligned with the patient's trachea 28, another set screw in the connection 110 is tightened to hold the arcuate member 108 against transverse movement relative to the body section 86.

The guide rod 50 extends through a cylindrical passage in the guide section 114. Therefore, transverse movement of the arcuate member 108 relative to the body section 86, that is, in the direction indicated by the arrows 112 positions the guide rod 50 in alignment with the patient's mouth 12. The guide rod 50 is axially movable 116 relative to the guide section 114 into the patient's mouth 12 and trachea 28.

In the illustrated embodiment of the invention, the distance between the patient's Adam's apple 34 and the arcuate member 108 is indicated by indicia 124 (FIG. 1). The indicia 124 is disposed on the cylindrical body section 86 of the positioning apparatus 56. The position of the connection 110 relative to the indicia 124 indicates the distance which the arcuate member is spaced from the positioning section 96. The distance which the connection 110 is spaced from the positioning section 96 is a function of the distance between the patient's Adam's apple 34 and the entrance to the patient's mouth 12.

In the illustrated embodiment of the invention, the indicia 124 is formed by a plurality of colored bands 130. Each of the bands 130 has a different color from the other bands. Each of the bands 130 has the same axial extent. However, the bands could have different axial extents if desired. Rather than using the colored bands 130 as the indicia 124, numerical indicia could be provided. However, it is believed that it may be easier to read the different colored bands 130 than to read numerical indicia.

Colored bands 142 are provided on the guide rod 50. The colored bands 142 have different colors which correspond to the colors of the bands 130 on the cylindrical body section 86 of the positioning apparatus 56. The colored bands 142 on the guide rod 50 are spaced from the end portion 52 of the guide rod by the same distance which correspondingly colored bands 130 on the body section 86 are spaced from the center of the Adam's apple 34.

The bands 142 on the guide rod 50 cooperate with an end portion 156 (FIG. 1) of the guide section 114 to indicate when the leading end portion 52 of the guide rod is in a desired position relative to the patient's trachea 28. Thus, assuming that a red colored band 130 on the cylindrical body section 86 of the positioning apparatus 56 is aligned with the connection 110, the red band on the guide rod 50 will be moved to a position in which it is adjacent to the guide section 114. When the guide rod 50 has been moved to a position in which the red band is adjacent to the guide section 114, the leading end portion 52 of the guide rod will have moved through a desired distance into the patient's trachea 28 and will be aligned with the patient's Adam's apple 34.

When the positioning apparatus 56 is to be associated with a different portion of a patient's body, the indicia 124 would be revised to correspond to the distance which the guide rod 50 is to be moved relative to the arcuate member 108 to bring the leading end portion 52 of the guide rod into alignment with the positioning section 96 or to a position spaced a desired distance from the positioning section. It is contemplated that the positioning apparatus 56 maybe used during endoscopic, arthroscopic, or fiber optic surgery at many locations in a patient's body, for example during surgery on joints in the patient's body.

The positioning apparatus 56 may be used in association with the delivery of medicants to relatively inaccessible locations in a patient's body. For example, a medicant could be connected with the leading end portion 52 of the guide rod 50 and released when the indicia 124 indicated that the medicant has been moved to a desired position relative to the positioning section 96. The medicant may be released by activating a holder, disposed at the leading end portion 52 of the guide rod. A Bowden cable or other actuator may extend through the guide rod to the medicant holder to operate the medicant holder from a closed condition to an open condition to release the medicant.

Tracheal Intubination

Once the guide rod 50 has been moved through a desired distance into the patient's trachea 28, the positioning apparatus 56 is separated from the guide rod 50 while the guide rod remains stationary relative to the patient's trachea. Thus, once the indicia 142 on the guide rod 50 indicates that the leading end portion 52 of the guide rod has been moved through a desired distance into the patient's trachea 28, axial movement of the guide rod 50 is interrupted. At this time, one of the colored bands 142 on the guide rod 50 corresponding to the one of the colored bands 130 aligned with the connection 110, is aligned with the end surface 156 on the guide section 114

The guide section 114 is then slid axially outward, that is toward the left as viewed in FIG. 1, along the guide rod 50. During this sliding movement of the guide section 114 along the guide rod 50, the guide rod is manually held against movement relative to the patient's mouth 12 and trachea 28. The upper section 80 and base section 78 are separated from the patient during movement of the guide section 114 along the guide rod 50. As this occurs, the guide rod 50 is stationary relative to the patient.

Once the upper section 80 has been separated from the guide rod 50, the tracheal tube 38 (FIG. 2) is slid along the guide rod 50 into the patient's trachea 28. Thus, the end of the guide rod 50 remote from the patient's mouth 12 and trachea 28 is inserted into the tracheal tube 38. As this is done, the guide rod 50 is manually held against movement relative to the patient's mouth 12 and trachea 28. The tracheal tube 38 is then moved axially along the guide rod 50 while the leading end portion 52 of the guide rod remains stationary in the patient's trachea.

As the tracheal tube 38 is moved axially along the guide rod 50, the guide rod directs the leading end portion of the tracheal tube into the patient's larynx 30 and past the vocal cords 32. The leading end of the tracheal tube 38 is centered in the space between the vocal cords and the entrance to the patient's trachea by the guide rod 50. This minimizes irritation of the patient's vocal cords 32. The tracheal tube 38 is moved along the guide rod 50 at least until the leading end of the tracheal tube engages the leading end portion 52 of the guide rod 50.

It is contemplated that it may be desired to move the tracheal tube 38 further into the patient's trachea 28 than the distance which the guide rod 50 is moved into the patient's trachea. If this is the case, the tracheal tube 38 is pushed axially along the guide rod 50 past the leading end portion 52 of the guide rod. As this occurs, the leading end portion 52 of the guide rod 50 is compressed slightly and enters the tracheal tube 38.

Once the tracheal tube 38 has been moved to a desired depth into the patient's trachea 28, the guide rod 50 is removed from the tracheal tube (FIG. 7). The tracheal tube 38 then provides a passage for the conduction air, other gases, and/or medication to the patient's lungs Laryngoscope This contemplated that a laryngoscope 170 (FIG. 3) maybe connected with the connection 110 which interconnects the body section 86 and arcuate upper section 80 of the positioning apparatus 56. The laryngoscope 170 and body section 86 are moveable relative to each other to enable the laryngoscope to be positioned in the patient's mouth 12. As the laryngoscope 170 is inserted into the patient's mouth 12, the laryngoscope engages the patient's tongue 276. The laryngoscope then holds the patients tongue in a desired position in the mouth 12 of the patient.

The laryngoscope 170 is then inserted further into the patient's mouth 12 to expose progressively deeper structures within the oropharynx. The laryngoscope 170 could be advanced to facilitate visualization of the glottic opening in a known manner. Although the laryngoscope may be provided as part of the positioning apparatus 56, in the manner illustrated in FIG. 3, it is contemplated that the laryngoscope 170 could be separate from the positioning apparatus if desired. Regardless of whether the laryngoscope 170 is formed as part of the positioning apparatus 56 or separate from the positioning apparatus, the laryngoscope is utilized in a known manner in management of the patient's tongue and airway.

Second Embodiment

A second embodiment of the invention is illustrated in FIGS. 4 through 10. Since the embodiment of the invention illustrated in FIGS. 4-10 is generally similar to embodiment of the invention illustrated in FIGS. 1-3, similar terminology will be utilized to refer to similar components.

Figure 4:
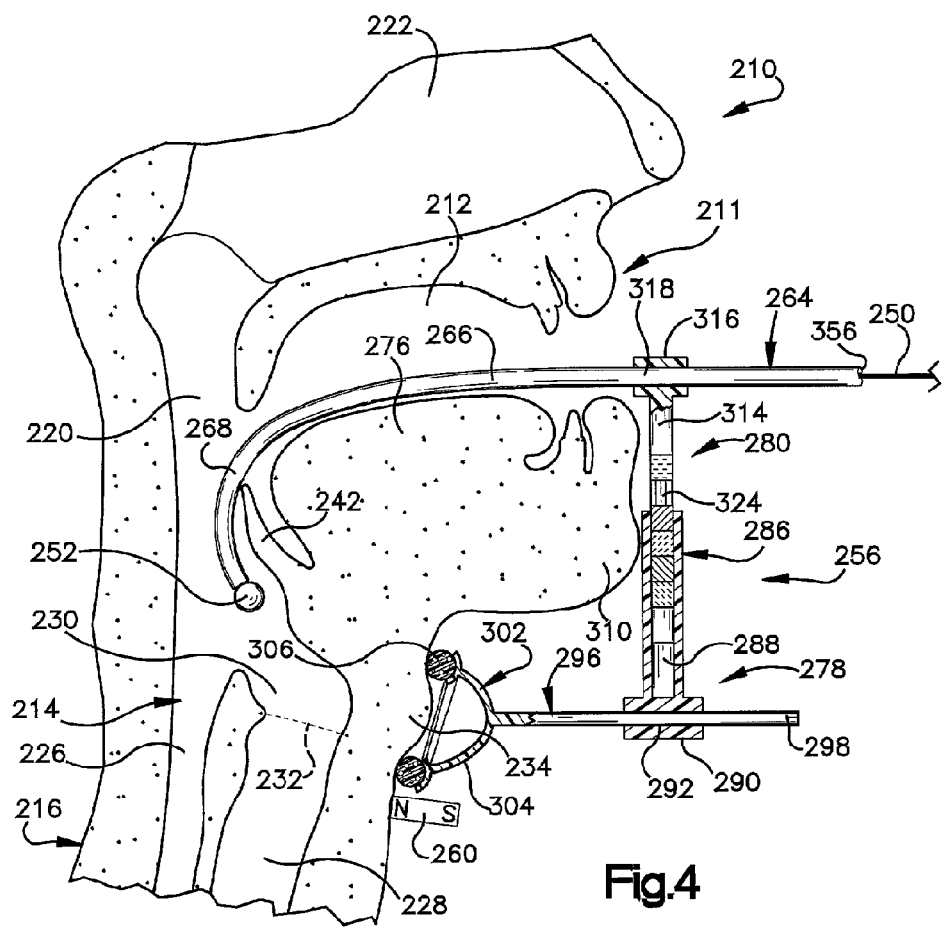
FIG. 4 is a fragmentary schematic illustration depicting the use of another embodiment of the positioning apparatus to position a guide rod relative to the mouth and trachea of a patient.

A portion of a patient's head 210 has been illustrated schematically in FIG. 4. The patient's head includes a mouth 212 which is connected with a palate 211, a throat 214, and a neck 216 of the patient. Although the patient's head 210 has been schematically illustrated in an upright orientation in FIG. 4, it should be understood that the patient's head could be in a different orientation if desired. For example, the patient's head 210 could be in the orientation illustrated in FIGS. 1 and 2 for the patient's head 10.

A pharynx 220 extends downward from a nasal cavity 222 in the head 210 of the patient. The pharynx 220 is connected with an esophagus 226 and a trachea 228 in the neck 216 of the patient. The esophagus 226 extends from the pharynx 220 to the stomach of the patient. The trachea 228 extends from the pharynx to the bronchial tubes and lungs of the patient.

The trachea 228 (FIG. 4) has an upper end portion 230 which is referred to as the larynx. Vocal cords or folds 232 have been indicated schematically in FIG. 3 and are disposed in the larynx 230. The vocal cords 232 are adjacent to the Adam's apple 234 of the patient. The Adam's apple 234 is a laryngeal prominence formed by lamina of cartilage in the larynx.

Opening of a passage for air from the patient's mouth to the patient's lungs may require insertion of a flexible tracheal tube 238 (FIG. 10). Movement of the flexible tracheal tube 238 from the patient's mouth 212 into the pharynx 220 of the patient is relatively easily accomplished. However, directing the tracheal tube 238 into the patient's trachea 228 may present difficulties. This is because an anterior bend 240 must be formed in the tracheal tube 238. The anterior bend 240 extends around the epiglottis 242 into the larynx 230 at the upper end of the trachea 228. The anterior bend 240 can be minimized by placing the patient in the orientation illustrated in FIGS. 1 and 2.

During movement of the leading end of the tracheal tube 238 through the larynx 230, it is desirable to have the tracheal tube near the central portion of the laryngeal cavity in order to minimize irritation of the vocal folds or cords 232 by the tracheal tube. In accordance with a feature of the present invention, a flexible guide wire or rod 250 (FIGS. 4 and 9) is utilized to guide movement of the flexible tracheal tube 238 (FIGS. 9 and 10) into the trachea 228. The flexible guide rod 250 (FIG. 9) has a soft generally spherical leading end portion 252. The leading end portion 252 of the guide rod 250 is formed of a resiliently compressible material which is readily deflected by engagement with the vocal cords or folds 232 and by engagement with the surface of the trachea 228. If desired, the leading end portion 252 of the guide rod 250 may be coated with a suitable lubricant to facilitate movement of the leading end portion between the vocal cords with minimum of irritation.

In accordance with another feature of the invention, the guide wire 250 is initially positioned relative to the patient's trachea 228 with a positioning apparatus 256 (FIG. 4). The positioning apparatus 256 engages the patient's Adam's apple 234 to locate the positioning apparatus relative to the trachea 228 of the patient. In addition, the positioning apparatus 256 provides a measurement which is a function of the distance between the Adam's apple 234 and the mouth 212 of the patient. This measurement is utilized to determine the distance through which the guide rod 250 is to be moved relative to the positioning apparatus 256 as the guide rod is inserted into the trachea 228.

In accordance with still another feature of the present invention, a magnet 260 (FIG. 4) is utilized to attract the leading end portion 252 of the guide rod 250 and to steer the leading end portion of the guide rod into the patient's trachea 228. The magnet 260 is a permanent magnet formed of a strongly magnetizable material such as cobalt and neodymium. Of course, other known magnetizable materials having high saturation magnetization values, such as cerium, praseodymium, and/or samarium with cobalt and/or other materials, could be used. Alternatively, the magnet 260 may be an electromagnet To enable the leading end portion 252 of the guide rod 250 to be attracted by a magnetic field emanating from the magnet 260, the leading end portion 252 of the guide rod contains ferrite particles. The ferrite particles may or may not be magnetized. Or course, other known magnetizable or magnetic particles could be utilized. When a magnet is positioned on the leading end portion 252 of the guide rod 250, the polarity of the leading end of the magnet on the guide rod is opposite from the polarity of the magnet 260.

As the guide rod 250 is moved downward (as viewed in FIG. 4) along the patient's pharynx toward the larynx 230, the leading end portion 252 of the guide rod enters the field of the magnet 260. The field of the magnet 260 has sufficient strength to cause the guide rod 250 to deflect slightly toward the right (as viewed in FIG. 4). As this occurs, the leading end portion 252 of the guide rod moves into the larynx 230 at a location adjacent to the center of the larynx. This enables the leading end portion 252 of the guide rod 250 to move between the vocal cords or folds 232 with a minimum of irritation to the vocal cords. Although the magnet 260 is described herein as steering the leading end portion 252 of the guide rod 250 into the trachea, it is contemplated that the magnet could be utilized to steer members at many different locations in a patient's body.

The magnet 260 may be an electromagnet. If the magnet 260 is an electromagnet, the magnet may be turned on and off, that is, energized and de-energized during steering of the leading end portion 252 of the guide 250. If desired, the leading end portion 252 of the guide rod 250 could also be formed by an electromagnet. If this was done, conductors for connecting the leading end portion 252 of the guide 250 would extend along the inside of the guide rod. By reversing the direction of current flow to either the electromagnet forming the magnet 260 or the electromagnet forming the leading end portion 252 of the guide rod 250, the two electromagnets could be made to sequentially attract and repel each other.

Steering of the leading end portion 252 of the guide rod 250 with the magnet 260 is facilitated by moving the magnet along the patient's neck 216, in the manner indicated schematically in FIG. 7. The magnet 260 may be moved up and down along the patient's neck. The magnet 260 may also be moved sidewards relative to the patient's neck. By moving the magnet 260 relative to the patient's neck, a magnetic field emanating from the magnet is effective to pull the leading end portion 252 of the guide rod 250 in the desired direction.

Although the use of the magnet 260 has been disclosed herein in association with the embodiment of the invention illustrated in FIGS. 4-10, it is contemplated that the magnet 260 could be used in association with other embodiments of the invention. For example, the magnet 260 could be used with the embodiment of the invention illustrated in FIGS. 1 and 2.

The magnet 260 may be used to steer devices other than the guide rod 250. When the positioning apparatus 56 (FIG. 1) is to be associated with a portion of a patient's body other than the trachea, the magnet 260 (FIG. 4) could be used to steer any one of many different devices to a desired location in the patient's body. A positioning apparatus, similar to the positioning apparatus 56 of FIG. 1 or the positioning apparatus 256 of FIG. 4, and a magnet, similar to the magnet 260 may be used during endoscopic, arthroscopic, or fiber optic surgery at many different locations in a patient's body. Thus, the magnet 260 may be used to steer a guide rod being positioned relative to a joint by a positioning apparatus, similar to the positioning apparatus 56 of FIG. 1 and the positioning apparatus 256 of FIG. 4, during surgery at the joint. The magnet 260 may also be used to position medicants at desired locations in the patient's body. Although it is believed that the magnet 260 will be advantageously used in association with a positioning apparatus similar to the positioning apparatus 56 of FIG. 1 or the other positioning apparatus 256 of FIG. 4, the magnet may be used in situations where the positioning apparatus is not required.

Positioning Apparatus of FIGS. 4-10

The positioning apparatus 256 (FIG. 4) positions the guide rod 250 relative to the patient's trachea 228 during insertion of the guide rod into the patient's trachea. In addition, the positioning apparatus 256 provides an indication of the distance which the guide rod is to be moved into the patient's trachea. By using the positioning apparatus 256, a person moving the guide rod 250 into the patient's trachea 228 can know where the leading end portion 252 of the guide rod is located relative to the trachea.

During movement of the guide rod 250 into the patient's trachea, the guide rod is moved axially through a flexible, generally cylindrical, guide tube 264 (FIG. 5). The guide tube 264 is formed of a resilient polymeric material. The guide tube 264 has a main section 266 and a leading end section 268. The leading end section 268 has a side wall 270 which is thinner than a side wall 272 of the main section 266. The side wall 270 is integrally molded as one piece with the thicker side wall 272. A generally cylindrical passage 274 (FIG. 5) extends axially through the guide tube 264.

The thin walled leading end section 268 of the guide tube 264 is molded so as to naturally assume the arcuate configuration illustrated in FIGS. 4 and 5. This enables the end section 268 of the guide tube 264 to be positioned in the patient's pharynx 220 (FIG. 4) with the end section forming a bend which extends around the upper end portion of the patient's epiglottis 242. Since the leading end section 268 has a relatively thin side wall (FIG. 5), the end section can be easily deflected as it is moved into position in the patient's pharynx 220. The thicker side wall 272 of the main section 266 of the guide tube 264 is effective to support the leading end section 268 in the patient's pharynx 220 and to depress a tongue 76 in the mouth 212 of the patient (FIG. 1).

The guide rod 250 may be formed of either polymeric material or metal. The illustrated polymeric guide rod 250 has a relatively small diameter and is readily deflected. The guide rod 250 has a circular cross sectional configuration.

The guide rod 250 extends axially through the guide tube 264 (FIG. 4). The guide rod 250 is axially movable relative to the guide tube 264 under the influence of force manually applied to the portion of the guide rod disposed to the right (as viewed in FIG. 4) of the positioning apparatus 256. This force results in axial movement of the guide rod 250 along the guide tube 264.

As the guide rod 250 is axially moved along the guide tube 264, the arcuate leading end section 268 of the guide tube 264 resiliently deflects the guide rod 250 to form the arcuate bend illustrated in FIG. 4. As the guide rod 250 is manually pushed toward the left (as viewed in FIG. 4), the leading end 252 of the guide rod moves downward (as viewed in FIG. 4) toward the larynx 230. As the leading end 252 of the guide rod 250 moves downward (as viewed in FIG. 4), tissues which may tend to block movement of the guide rod are pushed aside by the leading end of the guide rod. This clears a passage for the guide rod 250.

The positioning apparatus 256 is used to locate the leading end portion 252 of the guide rod 250 as the guide rod moves along the guide tube 264. The positioning apparatus 256 includes a base section 278 and an upper section 280 (FIG. 4). The base section 278 engages the patient's Adam's apple 234 to locate the positioning apparatus 256 relative to the patient's trachea 228. The upper section 280 of the positioning apparatus 256 holds the guide tube 264 which guides movement of the guide rod 250 during insertion of the guide rod into the patient's trachea 228.

The base section 278 and upper section 280 of the positioning apparatus 256 cooperate to provide a measurement of the distance between the patient's mouth 212 and the patient's Adam's apple 234. This distance will vary from patient to patient depending upon the size of the patient, the specific configuration of the head 210 of the patient, and other factors. The distance which the guide rod 250 must be moved axially relative to the guide tube 264 to move the leading end portion 252 of the guide rod into the patient's larynx 230 will vary as a function of variations in the distance between the patient's mouth 212 and the patient's Adam's apple 234. This is because the patient's Adam's apple 234 is located adjacent to the entrance to the trachea 228.

The base section 278 of the positioning apparatus 256 includes an upright tubular cylindrical body section 286. The body section 286 has a cylindrical chamber 288. The cylindrical upper section 280 of the positioning apparatus 256 is telescopically received in the chamber 288.

In addition, the base section 278 includes an end section 290. The end section 290 extends perpendicular to the body section 286. The end section 290 has a cylindrical central passage 292 which extends perpendicular to and intersects the central axis of the chamber 288. The body section 286 and the end section 290 are integrally molded as one piece of polymeric material.

The base section 278 also includes a positioning section 296 which engages the patient's Adam's apple 234 and is supported by the end section 290. The positioning section 296 includes a cylindrical support rod 298 which extends through the passage 292 and is connected with a locating portion 302 which engages the patient's Adam's apple 234. The locating portion 302 includes a generally hemispherical dome 304 and a resilient annular collar 306 which is connected to the rim of the dome 304. The collar 306 extends around the Adam's apple 234 and engages upper and lower sides and left and right sides of the Adam's apple to center the dome 304 on the Adam's apple.

If desired, the locating portion 302 could be constructed to engage only two sides of the Adam's apple 234. For example, the left and right sides of the Adam's apple 234. It is believed that it may be desired to form the locating portion 302 with the construction illustrated in FIGS. 25 and 26 herein. Alternatively, the locating portion 302 could be constructed so as to engage only the central portion of the Adam's apple 234.

However, it is believed that it may be desired to form the locating portion 302 so that it extends around the Adam's apple 234 so as to locate the positioning section 296 relative to the Adam's apple. Force may be manually applied against the positioning section 296 to minimize the anterior bend 240 (FIG. 10) which must be formed in the tracheal tube 238. The end section 290 is axially slidable along the support rod 298 so that the body section 286 is disposed adjacent to the chin 310 of the patient.

Although it is preferred to use the patient's Adam's apple 234 to locate the positioning apparatus 256 relative to the patient's trachea 228, a different portion of the patient's body could be used to locate the positioning apparatus relative to the patient's trachea. For example, the patient's shoulders could be used. Alternatively, bones in the patient's neck 216 could be used to locate the positioning apparatus 256 relative to the patient's trachea 228. However, it is believed that it will be preferred to use the patient's Adam's apple 234 to locate the positioning apparatus 256 due to the close proximity of the patient's Adam's apple to the upper end of the patient's trachea 228.

The upper section 280 of the positioning apparatus 256 includes a cylindrical rod portion 314 which is telescopically received in the body section 286 of the positioning apparatus. An upper end section 316 has a cylindrical passage 318 through which the guide tube 264 extends. The passage 318 has a longitudinal central axis which extends parallel to the longitudinal central axis of the passage 292 and to the longitudinal central axis of the support rod 298. The guide tube 264 is slidable in the passage 318.

The guide tube 264 extends from the passage 318 into the patient's mouth 212. Thus, the passage 318 in the upper section 280 of the positioning apparatus 256 is axially aligned with the patient's mouth 212. Similarly, the passage 292 (FIG. 4) in the end section 290 of the base section 278 of the positioning apparatus 256 is axially aligned with the patient's Adam's apple 234. Therefore, the positioning apparatus 256 can be utilized to measure the distance between the Adam's apple 234 and the patient's mouth 212.

The entrance through which the guide rod 250 must pass into the patient's trachea 228 is adjacent to the Adam's apple 234. Therefore, the distance through which the leading end portion 252 of the guide rod 250 must be moved relative to the guide tube 264 (FIG. 4) to enter the patient's trachea 228, is a function of the distance between the patient's Adam's apple 234 and the patient's mouth 212. The positioning apparatus 256 measures the distance between the patient's Adam's apple 234 and the patient's mouth by determining the position of the base section 278 and upper section 280 of the positioning apparatus relative to each other.

In the illustrated embodiment of the invention, the distance between the patient's Adam's apple 234 and the patient's mouth 212 is indicated by indicia 324 (FIG. 6). The indicia 324 is disposed on the cylindrical rod portion 314 of the upper section 280 of the positioning apparatus 256. The rod portion 314 is telescopically received in the cylindrical chamber 288 in the body section 286 of the positioning apparatus 256.

The position of an annular upper end surface 328 on (FIG. 6) the body section 286 relative to the indicia 324 indicates the distance which the rod portion 314 is extended from the body section 286. The distance which the rod portion 314 is extended from the body section 286 is a function of the distance between the patient's Adam's apple 234 and the entrance to the patient's mouth 212.

In the illustrated embodiment of the invention, the indicia 324 is formed by a plurality of colored bands 330, 332, 334, 336, 338 and 340 (FIG. 6). Each of the bands 330-340 has a different color from the other bands. It should be understood that a lesser or greater number of colored bands 330-340 could be provided if desired. It should also be understood that although the bands 330-340 have the same axial extent, the bands could have different axial extents if desired. Rather than using the colored bands 330-340 as the indicia 324, numerical indicia could be provided. However, it is believed that it may be easier to read the different colored bands 330-340 than to read numerical indicia.

Bands 342, 344, 346, 348, and 350 (FIG. 8) are provided on the guide rod 250. The colored bands 342-350 have different colors which correspond to the colors of the bands 132-140 on the rod portion 314 (FIG. 6) of the positioning apparatus 256. It should be understood that although only the bands 342-350 having colors corresponding to the colors of the bands 132-140 are illustrated, an additional band having a color corresponding to the color of the band 330 in FIG. 6 is provided on the guide rod 250.

The bands 342-350 (FIG. 8) on the guide rod 250 cooperate with an annular end surface 356 (FIG. 4) on the guide tube 264 to indicate when the leading end portion 252 of the guide rod is in a desired position relative to the patient's trachea 228. Thus, assuming that the colored band 334 on the rod portion 314 of the positioning apparatus 256 is aligned with the end surface 328 on the body section 286 (as illustrated in FIG. 6), the band 344 (FIG. 8) on the guide rod 250 will be moved to a position in which it is partially covered by the guide tube 264 and projects outward from the end surface 356 (FIG. 4) for a distance corresponding to the distance which the band 334 projects outward from the end surface 328 on the body section 286 (FIG. 5). The band 344 has a color which is the same as the color of the band 334. When the guide rod 250 has been moved to a position in which the band 344 is partially enclosed by the guide tube 264, the leading end portion 252 of the guide rod will have moved through a desired distance into the patient's trachea 228, for example, a distance of approximately ten centimeters.

The bands 342-350 (FIG. 8) on the guide rod 250 are spaced a predetermined distance from the end surface 356 (FIG. 4) on the guide tube 264 when the leading end portion 252 of the guide rod is disposed in abutting engagement with the leading end section 268 of the guide tube 264. During movement of the indicia on the guide rod 250 from a position spaced from the end surface 356 of the guide tube 264 to a position in which the leading band on the guide rod 150 is adjacent to the end surface 356, the leading end portion 252 of the guide rod 250 will have moved from the pharynx 220 of the patient and into the larynx 230 past the vocal cords 232.

As the guide rod 250 continues to be manually pushed into the guide tube 264, the leading end portion 252 of the guide rod advances downward (as viewed in FIG. 4) in the trachea 228 of the patient. Movement of the guide rod 250 into the trachea 228 of the patient is interrupted when the band 344 having a color corresponding to the color of the band 334 (FIG. 6) has been partially covered by the guide tube 264.

The magnet 260 is utilized to steer the guide rod 250 during movement of the leading end portion 252 of the guide rod from the patient's mouth 212 into the patient's trachea 228. As the leading end portion 252 of the guide rod 250 is moved downward along the inside of the patient's neck, the magnet 260 is moved downward along the outside of the patient's neck. The magnetic field provided by the magnet 260 is effective to pull the leading end portion 252 downward as the magnet moves downward. Eventually, the leading end portion 252 of the guide rod 250 and magnet 260 will move downward from the entrance to the trachea 228 through a desired distance, for example a distance of approximately ten centimeters. Of course, the leading end portion 252 of the guide rod 250 could be moved through a different distance into the trachea 228 if desired.

It is contemplated that the distance between the patient's Adam's apple 234 and the entrance to the patient's mouth 212 will vary from patient to patient. However, the distance which the leading end portion 252 of the guide rod 250 is moved into the patient's trachea 228 will remain constant at a desired distance, for example, ten centimeters. This is because as the distance measured by the positioning apparatus 256 increases, the distance which the guide rod 250 is moved relative to the guide tube 264 increases. Conversely, as the distance which is measured by the positioning apparatus 256 decreases, the distance which the guide rod 250 is moved relative to the guide tube 264 decreases. The distance which is measured by the positioning apparatus 256 varies as a function of the distance between the mouth 212 and larynx 230 of the patient.

Tracheal Intubination

Once the guide rod 250 has been moved through a desired distance into the patient's trachea 228, the guide tube 264 and positioning apparatus 256 are separated from the guide rod 250 while the guide rod remains stationary relative to the patient's trachea. Thus, once the indicia on the guide rod 250 indicates that the leading end portion 252 of the guide rod has been moved through a desired distance into the patient's trachea 228, axial movement of the guide rod 250 is interrupted. At this time, one of the colored bands 342-350 on the guide rod 250 corresponding to the one of the colored bands 330-340 aligned with the end surface 328 (FIG. 4) on the body section 286 of the positioning apparatus is aligned with the end surface 356 (FIG. 4) on the guide tube 264.

The guide tube 264 is then slid axially outward, that is toward the right as viewed in FIG. 4, along the guide rod 250. During this sliding movement of the guide tube 264 along the guide rod 250, the guide rod is manually held against movement relative to the patient's mouth 212 and trachea 228. The positioning apparatus 256 is moved away from the patient along with the guide tube 264.

Once the guide tube 264 has been separated from the guide rod 250 (FIG. 9), the tracheal tube 238 is slid along the guide rod 250 into the patient's trachea 228. Thus, the end of the guide rod 250 remote from the patient's mouth 212 and trachea 228 is inserted into the tracheal tube 238. As this is done, the guide rod 250 is manually held against movement relative to the patient's mouth 212 and trachea 228. The tracheal tube 238 is then moved axially along the guide rod 250 while the leading end portion 252 of the guide rod remains stationary in the patient's trachea. If desired, the magnet 260 may be utilized to attract the leading end portion 252 of the guide rod 250, in the manner illustrated in FIG. 9, to facilitate maintaining of the leading end portion of the guide rod stationary in the patient's trachea 228.

As the tracheal tube 238 is moved axially along the guide rod 250, the guide rod directs the leading end portion of the tracheal tube along a bend 360 (FIG. 9) formed in the guide rod. After the leading end portion of the tracheal tube 238 has moved around the bend 360, the leading end portion of the tracheal tube enters the patient's larynx and moves past the vocal cords 232. The leading end of the tracheal tube 238 is centered in the space between the vocal cords and the entrance to the patient's trachea by the guide rod 250. This minimizes irritation of the patient's vocal cords 232. The tracheal tube 238 is moved along the guide rod 250 at least until the leading end of the tracheal tube engages the leading end portion 252 of the guide rod 250.

It is contemplated that it may be desired to move the tracheal tube 238 further into the patient's trachea than the distance which the guide rod 250 is moved into the patient's trachea. If this is the case, the tracheal tube 238 is pushed axially along the guide rod 250 past the leading end portion 252 of the guide rod. As this occurs, the leading end portion 252 of the guide rod 250 is compressed slightly and enters the tracheal tube 238.

Once the tracheal tube 238 has been moved to a desired depth into the patient's trachea 228, the guide rod 250 is removed from the tracheal tube (FIG. 10). The tracheal tube 238 then provides a passage for the conduction air, other gases, and/or medication to the patient's lungs.

Method of Utilization

When the tracheal tube 238 is to be inserted into a patient's trachea 228, the guide rod 250 is first positioned relative to the guide tube 264 at a location spaced from the patient. At this time, the leading end portion 252 of the guide rod 250 is disposed in abutting engagement with the leading end portion 268 of the guide tube 264. The upper section 280 of the positioning apparatus 256 is loosely positioned on the guide tube 264. The lower or base section 278 of the positioning apparatus 256 is separate and spaced from the upper section 280 of the positioning apparatus. A suitable lubricant may be applied to the leading end portion 252 of the guide rod 250 and to the leading end portion 268 of the guide tube 264.

The guide tube 264 is then inserted into the patient's mouth 212. As the guide tube 264 is inserted into the patient's mouth, the leading end portion 268 of the guide tube 264 and the leading end portion 252 of the guide rod 250 move from the patient's mouth into the pharynx 220 of the patient. As the leading end portion 268 of the guide tube 264 moves into the pharynx 220 of the patient, the natural resilience of the material of the guide tube causes the guide tube to spring back to its initial or free configuration illustrated in FIGS. 3 and 4.

As the guide tube 264 and guide rod 250 are manually moved together into the patient's mouth 212, the guide tube bends itself around the upper (as viewed in FIG. 3) portion of the patient's epiglottis 242. This results in the leading end portion 252 of the guide rod 250 being pointed downward (as viewed in FIG. 3) toward the lower end portion of the patient's pharynx 220. A person initially inserting the guide tube 264 and guide rod 250 into the patient's mouth 212 can visually ascertain when the guide tube and guide rod have moved to the position illustrated in FIG. 3

When the guide tube 264 and guide rod 250 have been positioned in this manner relative to the patient's mouth 212 and pharynx 220, the positioning apparatus 256 is assembled. To assemble the positioning apparatus, the rod portion 314 of the upper section 280 is telescopically inserted into the chamber 288 in the body section 286 of the positioning apparatus. Contemporaneously therewith, the locating portion 302 of the positioning apparatus 296 is moved into engagement with the patient's Adam's apple 234. The base section 278 and upper section 280 of the positioning apparatus 256 are moved axially along the guide tube 264 and support rod 298 until the base section and upper section of the positioning apparatus 256 are adjacent to the patient's chin 310 (FIG. 4). At this time, the coincident central axes of the rod portion 314 and body section 286 of the positioning apparatus 256 will extend perpendicular to the central axes of the guide tube 264 and support rod 298.

The magnet 260 is then positioned immediately beneath the patient's Adam's apple 234. This enables the magnetic field from the magnet 260 to extend leftward and upward (as viewed in FIG. 4) to the entrance to the patient's larynx 230. This results in the magnet 260 and positioning apparatus 256 being disposed in the orientation illustrated in FIG. 3 relative to the patient.

Figure 3:
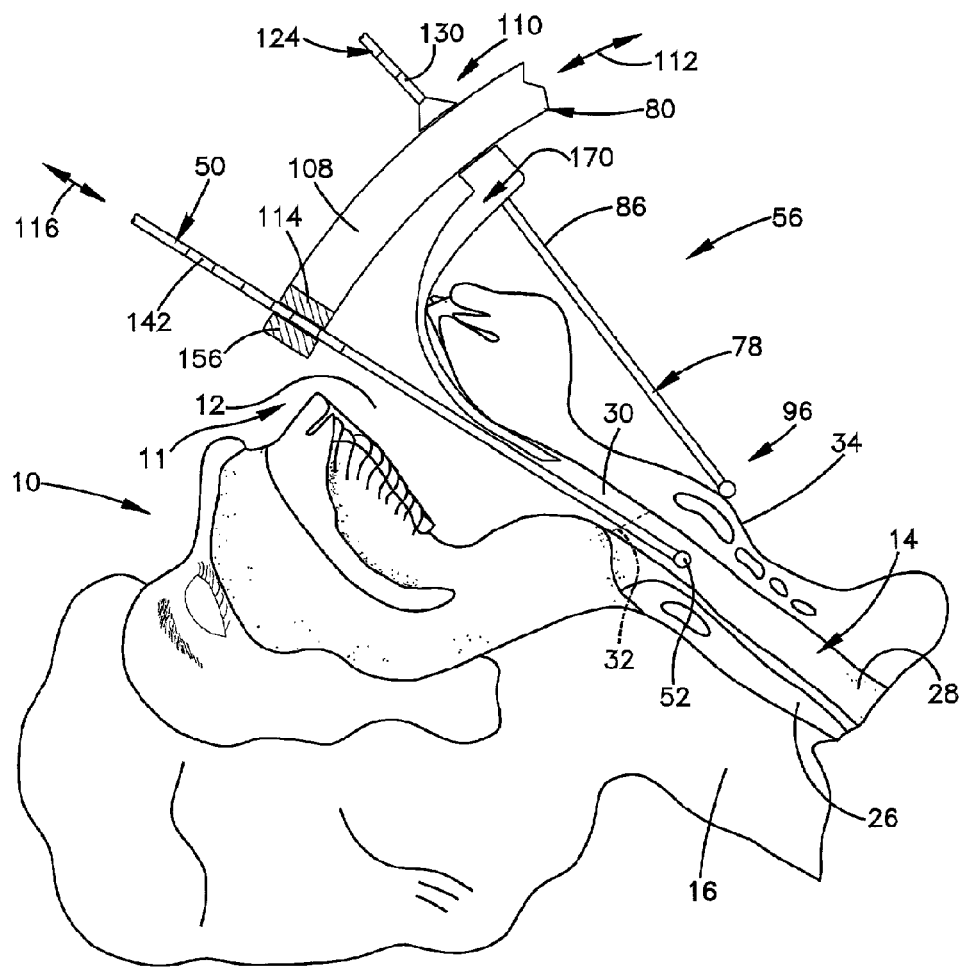
FIG. 3 is a fragmentary schematic illustration, similar to FIG. 1, illustrating the manner in which a laryngoscope may be combined with the positioning apparatus.

Once the positioning apparatus 256, guide tube 264 and guide rod 250 have been moved to the positions shown in FIG. 3 relative to the patient's head 210, the person using the positioning apparatus 256 visually determines the distance between the patient's Adam's apple 234 and the patient's mouth 212. This is accomplished by viewing the indicia 324 (FIG. 6) on the rod portion 314 of the positioning apparatus 256. By determining which of the bands 330-340 is aligned with the end surface 328 on the body section 286 of the positioning apparatus 256, the operator determines the distance between the patient's Adam's apple and the patient's mouth. The distance which the guide rod 250 must be moved into the patient's trachea 228 is a direct function of the distance between the patient's Adam's apple 234 and the patient's mouth 212.

The operator then begins to manually apply force against the rightward (as viewed in FIG. 4) portion of the guide rod 250 while holding the guide tube 264 against movement. This results in the leading end portion 252 of the guide rod moving downward toward the entrance to the patient's larynx 230. As the guide rod 250 begins to move downward, the bent leading end portion 268 of the guide tube 60 directs the leading end portion 252 of the guide rod 80 downward around the patient's epiglottis 242 in a direction toward the entrance to the larynx 230.

It is contemplated that the resiliently deflectable guide rod 250 will initially be formed with a bend which is a continuation of the bend in the leading end portion of the guide tube 264. Therefore, the natural resilience of the guide rod 250 will tend to cause the guide rod to bend rightward toward the patient's Adam's apple as the leading end portion 252 of the guide rod begins to move downward toward the larynx 230.

As the leading end portion 252 of the guide rod 250 approaches the entrance to the larynx 230, the field emanating from the magnet 260 attracts the leading end portion 252 of the guide rod 250. The magnetic attraction forces applied to the leading end portion 252 of the guide rod 250 also promote rightward (as viewed in FIG. 4) bending of the guide rod 250 toward the patient's Adam's apple 234. Thus, the combined effect of the magnet 260 and the natural resilience of the preformed guide rod 250 urge the leading end portions 52 of the guide rod 250 toward the entrance to the larynx 230 and away from the adjacent entrance to the esophagus 226. This ensures that the leading end portion 252 of the guide rod 250 enters the trachea 228 rather than the esophagus 226. If desired, the magnet 260 could be positioned above or on the patient's Adam's apple 234 and then moved downward as the guide rod 250 advances.

If desired, the flexible guide rod 250 could initially be formed with a straight configuration and only the magnet 260 would steer the leading end portion 252 of the guide rod into the entrance to the trachea 228. Alternatively, the use of the magnet 260 could be eliminated and only the preformed configuration of the guide rod 250 would be used to direct the leading end portion 252 of the guide rod into the entrance to the trachea 228. However, it is believed that it will be preferred to use both the preformed configuration of the guide rod 250 and the magnet 260 to direct the leading end portion 252 of the guide rod into the patient's trachea 228.

The colored bands 342-350 (FIG. 8) on the guide rod 250 cooperate with the end surface 356 (FIG. 4) of the guide tube 264 to provide an indication of the location of the leading end portion 252 of the guide rod relative to the patient's Adam's apple 234. As the leading end portion 252 of the guide rod 250 moves downward from the position shown in FIG. 3 toward the entrance to the larynx 230, the indicia bands 342-350 will move toward the end surface 356 of the guide rod 250. As the leading end portion 252 of the guide rod 250 moves through the entrance to the larynx 230, the indicia on the guide rod 250 will be approaching the end surface 356 of the guide tube 264.

Continued axial movement of the guide rod 250 relative to the stationary guide tube 264 moves the leading end portion 252 of the guide rod to a position immediately above the patient's vocal cords 232. As this occurs, the leading end portion 252 of the guide rod 250 is strongly attracted by the magnetic field emanating from the magnet 260. Due to the approach of the indicia on the guide rod 250 toward the end surface 356 of the guide tube 264, the operator realizes that the leading end portion 252 of the guide rod 250 is adjacent to the magnet 260 and moves the magnet downward (as viewed in FIG. 4) along the neck 216 of the patient as the guide rod 250 continues to be moved leftward through the stationary guide tube 264. As the magnet 260 is manually moved downward (as viewed in FIG. 4) with the leading end portion 252 of the guide rod 250, the magnet continues to attract the leading end portion of the guide rod.

One of the bands 330-340, having a particular color, for instance, red, on the rod portion 314 (FIG. 6) will be adjacent to the end surface 328 on the body section of the positioning apparatus 256. When a correspondingly colored band, that is, when the red band 344 on the guide rod 250 (FIG. 8), is partially covered by the guide tube 264 and extends axially outward from the end surface 356, the operator will know that the leading end portion 252 of the guide rod 250 will have moved past the vocal 232 to the desired position relative to the patient's trachea. Insertion of the guide rod 250 into the guide tube 264 is then interrupted.

After the guide rod 250 has been inserted for the desired distance into the patient's trachea 228, the guide tube 264 and positioning apparatus 256 are separated from the guide rod 250. During separation of the guide tube 264 and positioning apparatus 256 from the guide rod 250, the guide rod is maintained stationary relative to a patient's trachea 228. In the illustrated embodiment of the invention, the guide tube 264 is merely moved rightward (as viewed in FIG. 4) along the stationary guide rod 250 to disengage the guide tube and the positioning apparatus from the guide rod.

If desired, a slot could be provided in the guide tube 264 to facilitate disengagement of the guide tube from the guide rod. A corresponding slot could be formed in the end section 316 of the positioning apparatus 256. The slots in the guide tube 264 and end section 316 could be partially or fully blocked during insertion of the guide rod 250 into the guide tube 264. When the guide tube 264 is to be separated from the guide rod 250, that is after the guide rod has been inserted for the desired distance into the patient's trachea 228, latch or closure members for the slots could be moved to open positions and the guide tube 264 and apparatus 256 moved out of engagement with the stationary guide rod 250.

Once the guide tube 264 and positioning apparatus 256 have been disengaged from the guide rod 250, the guide rod is utilized to guide movement of the tracheal tube 238 into the patient's trachea 228. The tracheal tube 238 has a substantially larger diameter than the guide tube 264 to provide for a relatively large central opening through which air or other gas may pass into the patient's trachea 228.

When the tracheal tube 238 is to be moved into the patient's trachea 228, the guide rod 250 is telescopically inserted into the leading end of the tracheal tube. At this time, the right end (as viewed in FIG. 4) of the guide rod 250 will extend beyond the far right end of the tracheal tube 238. Therefore, the guide rod 250 can be manually grasped and the tracheal tube 238 moved axially along the guide rod while the guide rod remains stationary relative to the patient's trachea 228.

The tracheal tube 238 is moved leftward, in the manner indicated by the arrow in FIG. 9, along the stationary guide rod 250 into the patient's mouth 212. The tracheal tube 238 is then moved around the bend 360 in the stationary guide rod 250 and into the patient's trachea 228. Since the guide rod 250 extends from the patient's pharynx 220 into the trachea 228, the guide rod 250 blocks movement of the leading end portion of the tracheal tube 238 into the patient's esophagus 226. The guide rod 250 acts as a track along which the tracheal tube 238 moves into the patient's larynx 230 and not into the adjacent esophagus 226.

As the leading end portion of the tracheal tube 238 approaches and moves past the vocal cords 232, the guide rod 250 guides movement of the leading end portion of the tracheal tube in such a manner as to minimize irritation of the vocal cords. Thus, the guide rod 250 centers the leading end portion of the tracheal tube 238 in the space between the vocal cords. By lubricating the leading end portion of the tracheal tube 238 and centering the leading end portion of the tracheal tube in the space between the vocal cords 232, the tracheal tube can be moved into the patient's trachea 228 with a minimal amount of irritation to the vocal cords.

As the tracheal tube 238 is moved through the patient's larynx 230, the magnet 260 is disposed adjacent to the leading end portion 252 of the guide rod 250. Therefore, the leading end portion 252 of the guide rod 250 is attracted by the magnet 260 and tends to remain stationary in the patient's trachea 228. As the tracheal tube 238 is inserted into the patient's trachea 228, the leading end portion of the tracheal tube 238 moves past the leading end portion 252 of the guide rod 250. As this occurs, the leading end portion 252 of the guide rod 250 is slightly compressed and moves into the tracheal tube 238. Once the tracheal tube 238 has moved to a desired position relative to the trachea 228, the guide rod 250 is withdrawn from the tracheal tube 238 while the tracheal tube is maintained stationary relative to the patient's trachea.

In the embodiment of the invention illustrated in FIGS. 4-10, the magnet 260 (FIG. 4) is utilized to attract the leading end portion 252 of the guide rod 250. However, it is contemplated that the magnet 260 could be used for other purposes if desired. For example, the magnet 260 could be used to position a suture anchor relative to body tissue.

When the magnet 260 is to be utilized to position a suture anchor relative to body tissue, a leading end portion of the suture anchor is formed of a magnetizable material, such a ferrite. Alternatively, the leading end portion of the suture anchor could be formed of a magnetic material such as cobalt, neodymium, cerium, praseodymium, and/or samarium. If this was done, the magnet 260 would be oriented relative to the magnet on the suture anchor to have a pole of the magnet 260 of opposite polarity to the leading end of the suture anchor toward the suture anchor.

The trailing end portion of the suture anchor may be formed of a nonmagnetic material, such as a biodegradable polymer. The suture would extend through an opening in the nonmagnetic material of the trailing end portion of the suture anchor. Once the suture anchor had been moved to a desired position relative to body tissue by attraction of the magnet 260 for the leading end portion of the suture anchor, the leading end portion of the suture anchor may be separated from the trailing end portion of the suture anchor. The leading end portion of the suture anchor could then be removed from the patient's body to eliminate the possibility of an undesired interaction in the future with a magnetic field device, such as a magnetic resonance imaging device (MRI). The suture would be held in place by the nonmagnetic trailing end portion of the suture anchor Embodiment of FIG. 11

In the embodiment of the invention illustrated in FIGS. 4-10, a guide tube 264 is utilized to guide movement of the guide rod 250 as the guide rod is moved from the patient's pharynx 220 into the patient's trachea 228. The guide tube 264 is then removed and a tracheal tube 238 is slid along the guide rod 250 into the patient's trachea. In the embodiment of the invention illustrated in FIG. 11, the tracheal tube is used to guide movement of the guide rod into the patient's trachea. This eliminates the need for a separate guide tube. Since the embodiment of the invention illustrated in FIG. 11 is generally similar to the embodiment of the invention illustrated in FIGS. 4-9, similar numerals will be utilized to designate similar components, the suffix letter "a" being associated being associated with the numerals of FIG. 11 to avoid confusion.

A patient's head 210a (FIG. 11) includes a mouth 212a which is connected with a throat 214a in a neck 216a of the patient. A pharynx 220a is connected with an esophagus 226a and a trachea 228a. A larynx 230a forms an upper end portion of the trachea 228a and contains vocal cords 232a. An Adam's apple 234a is formed by laminae of cartilage in the patient's larynx 230a.

A positioning apparatus 256a is utilized to position a tracheal tube 238a and a guide rod or wire 250a during insertion of the guide rod and during insertion of the tracheal tube into the patient's trachea 228a. The tracheal tube 238a (FIG. 11) is flexible and is formed of a resilient polymeric material. The tracheal tube 238a is initially formed with a bend 380 in a leading end portion of the tracheal tube. When the tracheal tube 238a is released or unrestrained, the natural resilience of the tracheal tube causes the bend 380 to form in the manner illustrated in FIG. 10. However, the tracheal tube 238a is flexible so that the bend 380 is easily removed from the tracheal tube by the application of a relatively small force or pressure against the leading end portion of the tracheal tube.

In the embodiment of the invention illustrated in FIG. 10, the bend 380 in the tracheal tube 238a has a greater extent than a corresponding bend in a leading end section 268 of the guide tube 264 (FIG. 4). If desired, the bend in the tracheal tube 238a (FIG. 11) could be shortened so that the leading end portion of the tracheal tube 238a has a configuration which corresponds to the configuration of the guide tube 264 of FIG. 4

The positioning apparatus 256a (FIG. 11) includes a base section 278a and an upper section 280a. A rod portion 314a of the upper section 280a is telescopically received in a chamber 288a in the base section 278a. Indicia 324a on the rod portion 314a cooperates with a body section 286a of the base section 278a to provide a visual indication of the distance between the patient's Adam's apple 234a and the patient's mouth 212a in the manner previously described in conjunction with the positioning apparatus of FIG. 4.

The base section 278a of the positioning apparatus 256a includes a positioning section 296a which engages the patient's Adam's apple 234a. The positioning section 296a includes a locating portion 302a which engages the patient's Adam's apple 234a. The locating portion 302a includes a dome 304a and a soft annular collar 306a. Rather than using the collar 306a, it may be preferred to utilize a pair of positioning fingers which engage the neck 216a of the patient at laterally opposite sides of the Adam's apple 234a.

Indicia (not shown) is provided on the guide rod 250a to indicate the position of the guide rod relative to a proximal end of the tracheal tube 238a, that is, the right end as viewed in FIG. 11. It should be understood that the tracheal tube 238a and the guide rod 250a extend toward the right from the fragmentary end portions illustrated in FIG. 11. The indicia on the guide rod 250a is formed by bands corresponding to the bands 342-350 of FIG. 8. Rather than cooperating with the end 156 (FIG. 4) of a guide tube 264, the bands on the guide rod 250a (FIG. 11) cooperate with an end (not shown) of the tracheal tube 238a to indicate the position of the guide rod 250a relative to the tracheal tube 238a.

When the guide rod 250a is to be moved from the patient's pharynx 220a into the patient's trachea 228a, the guide rod is moved axially relative to the stationary tracheal tube 238a. As this occurs, a leading end portion 252a of the guide rod 250a moves downward (as viewed in FIG. 11) past the patient's vocal cords or folds 32a and into the patient's trachea. As the leading end portion 252a of the guide rod 250a moves from the patient's pharynx 220a into the patient's trachea 228a, the leading end portion of the guide rod gently deflects body tissue. For example, the leading end portion 252a of the guide rod 250a may gently engage and slightly deflect the patient's vocal cords or folds 32a.

A magnet 260a is initially positioned adjacent to the patient's Adam's apple 234a, in the manner indicated in dashed lines in FIG. 11. Ferrite particles in the soft, resiliently compressible leading end portion 252a of the guide wire 250a are attracted by the magnet 260a. This attraction causes the leading end portion 252a of the guide wire 250a to move into the open upper end portion of the trachea 228 rather than into the adjacent open upper end portion of the esophagus 226a. In addition, movement of the leading end portion 252a of the guide wire 250a into the open upper end portion of the trachea 228 is promoted by the bend 380 in the tracheal tube 238a. If desired, the magnet 260a could initially be positioned on or above the patient's Adam's apple 234a and moved downward from there.

As the guide wire continues to be inserted into the tracheal tube 238a, the guide wire moves downward in the patient's trachea 228a. At the same time, the magnet 260a is moved downward along the outer side of the patient's neck 216a. The indicia (not shown) on the guide rod 250a provides an indication to an operator of the position of the leading end portion 252a of the guide rod. This enables the operator to follow the leading end portion 252a of the guide rod 250a with the magnet 260a as the guide rod continues to be moved through the tracheal tube 238a into the patient's trachea 228a.

Once the guide rod 250a has been moved for a desired distance into the trachea 228a, the guide rod 250a is held stationary relative to the patient's trachea. The tracheal tube 238a is then moved axially toward the left (as viewed in FIG. 11) and downward into the patient's trachea 228a. During this downward movement of the tracheal tube 238a, the guide rod 250a blocks sidewise movement of the leading end of the tracheal tube so that the tracheal tube enters the larynx 230a rather than the adjacent open upper end of the esophagus 226a. As the tracheal tube 238a continues to be inserted into the trachea 228a, the leading end of the tracheal tube 238a moves into engagement with the leading end portion 252a of the guide rod 250a. The leading end portion 252a of the guide rod 250a is then compressed somewhat by the leading end portion of the tracheal tube 238a and moves into the passage in the tracheal tube. The tracheal tube 238*a* is then moved further into the trachea 228*a*.

After the tracheal tube 238*a* has been positioned relative to the patient's trachea, the guide rod 250*a* is withdrawn from the tracheal tube while the tracheal tube remains stationary relative to the patient's trachea 228*a*. The positioning apparatus 256*a* is then separated from the tracheal tube 238*a*.

Figure 12:
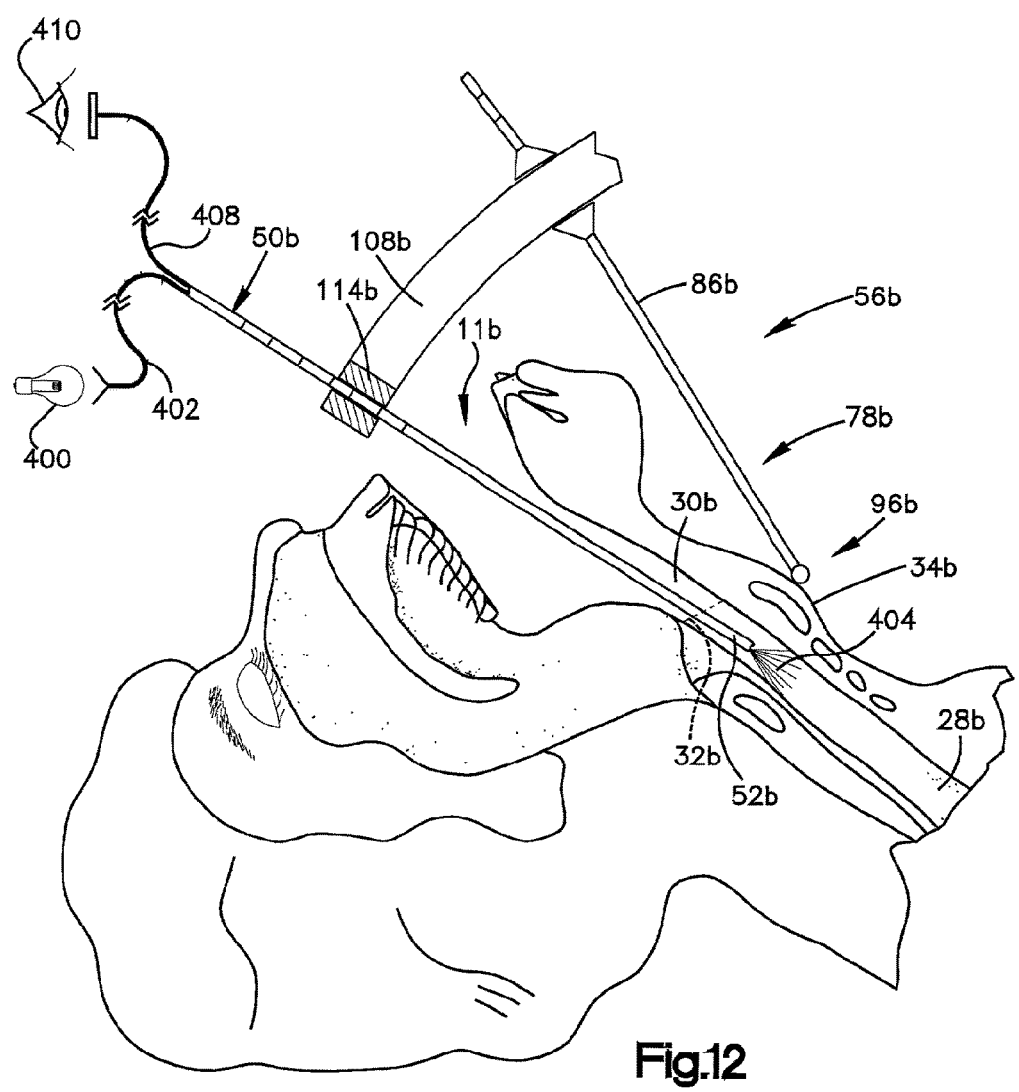
FIG. 12 is a fragmentary schematic illustration, similar to FIG. 1, illustrating an embodiment of the positioning apparatus which transmits an image of body tissue adjacent to a leading end portion of the guide rod.

Embodiment of FIG. 12

In the embodiment of the invention illustrated in FIG. 1, a leading end portion 52 of the guide wire or rod 50 is inserted between the vocal cords or folds in the respiratory system 11 of the patient. It's contemplated that movement of the leading end portion 52 of the guide rod 50 between the vocal cords 32 to a desired depth in the patient's trachea 28 may be facilitated by transmitting images of body tissue adjacent to the leading end portion of the guide rod to a viewing location outside of the patient's body. Since the embodiment of the invention illustrated in FIG. 12 is generally similar in the embodiment invention illustrated in FIGS. 1 and 2, similar numerals will be utilized to designate similar components, the suffix letter "b" being added to the numerals of FIG. 12 in order to avoid confusion.

A positioning apparatus 56*b* is utilized to position a flexible guide rod 50*b* relative to the patient's respiratory system 11*b*. The positioning apparatus 56*b* includes a body section 86*b* and a base section 78*b* which is connected with a positioning section 96*b*. The positioning section 96*b* engages the patient's Adam's apple 34*b*. An arcuate member 108*b* is connected with the base section 78*b*. The guide rod 50*b* is moveable relative to a guide section 114*b* connected with arcuate member 108*b*. The construction and the manner of using the positioning apparatus 56*b* and guide rod 50*b* is the same as was previously described in conjunction with the embodiment invention illustrated in FIGS. 1 and 2.

In accordance with a feature the embodiment invention illustrated in FIG. 12, light from a light source 400 is conducted through a fiber optic tube 402 to a leading end portion 52*b* of the flexible guide rod 50*b*. The light transmitted from the light source 400 through the fiber optic tube 402 to the leading end portion 52*b* of the guide rod 50*b* is directed from the leading end portion of the guide rod on to adjacent body tissue, in the manner indicated schematically at 404 in FIG. 12. If desired, a plurality of fiber optic tubes 402 could be provided to conduct light from the light source 400 to the leading end portion 52*b* of the guide rod. These fiber optic tubes could be bundled together or could be spaced part at the leading end portion 52*b* of the guide rod 50*b*.

The light 404 which illuminates the body tissue immediately ahead of the leading end portion 52*b* of the guide rod 50*b* is reflected from the body tissue and is transmitted through a fiber optic tube 408 to the eye 410 of a viewer. This results in the transmission of an image of the body tissue adjacent to the leading end portion 52*b* of the guide rod 50*b* to the viewer to facilitate visualization, by the viewer, of the body tissue. If desired, a plurality of fiber optic tubes 408 could be provided to conduct light from the leading end portion 52*b* of the guide rod to the eye 410 of the viewer. These fiber optic tubes could be bundled together or could be spaced apart at the leading end portion 52*b* of the guide rod 50*b*.

By visualizing the body tissue immediately ahead of the leading end portion 52*b* of the guide rod 50*b*, the viewer can determine the location of the leading end portion of the guide rod relative to the larynx 30*b* and vocal chords 32*b* of a patient as the leading end portion of the guide rod moves into the larynx and between the vocal chords. Since the light 404 illuminates body tissue immediately ahead of the leading end portion 52*b* of the guide rod 50*b*, the light enables the viewer to continuously visualize where the leading end portion 52*b* of the guide rod 50*b* is located along the insertion path in the respiratory system 11*b* of the patient.

In the embodiment invention illustrated in FIG. 12, the fiber optic tubes 402 and 408 extend through the guide rod 50*b* to enable an image of body tissue immediately ahead of the leading end portion 52*b* of the guide rod to be transmitted to a viewer. It is contemplated that movement of a tracheal tube, corresponding to tracheal tube 38 of FIG. 2, along the guide rod 50*b* into the patient's respiratory system 11*b* will be facilitated by illuminating body tissue immediately ahead of the leading end portion of the tracheal tube. Therefore, the side wall of the tracheal tube may be provided with fiber optic tubes which transmit light from a light source, such as a light source 400, to a location immediately ahead of the leading end portion of the tracheal tube and transmit an image of illuminated body tissue immediately ahead of the leading end portion of tracheal tube to a viewer.

As the tracheal tube is moved along the guide rod 50*b* into the patient's respiratory system, in the manner previously explained in conjunction with the embodiment invention illustrated in FIG. 2, body tissue immediately ahead of the leading end portion 52*b* of the stationary guide rod 50*b* is illuminated and body tissue immediately ahead of the tracheal tube is illuminated. Therefore, as the leading end portion of the tracheal tube approaches the vocal chords 32*b*, a surgeon or other viewer can easily determine the location of the leading end portion of the tracheal tube relative to the vocal chords. As the leading end portion of the tracheal tube approaches the leading end portion 52*b* of the guide rod, the image transmitted to the viewer will be of body tissue illuminated by both light transmitted from the leading end portion 52*b* of the guide rod and light transmitted from the leading end portion of the tracheal tube.

The leading end portion of the tracheal tube may be inserted into trachea 28*b* of a patient for greater distance than the distance which the guide rod 50*b* is inserted into the trachea. As the leading end portion of the tracheal tube moves past the leading end portion 52*b* of the guide rod 50*b*, illumination from the leading end portion of the guide rod 50*b* will be at least partially blocked from transmission back to the viewer through fiber optics in the tracheal tube. Therefore, the viewer will easily be able to determine when the leading end portion of the tracheal tube has moved past the leading end portion of the guide rod 50*b*.

Although the eye 410 of a viewer has been schematically illustrated in FIG. 12, it is contemplated that the image transmitted through the fiber optic tube 408 may be displayed on a viewing screen. If this was done, the image transmitted through the fiber optic tube 408 would be transmitted to a computer and a viewing screen associated with the computer would display an image of the body tissue immediately ahead of the leading end portion 52*b* of the guide rod 50*b*. As the tracheal tube is moved along the guide rod into the patient's respiratory system 11*b*, an image of body tissue immediately ahead of the leading end portion of the tracheal tube may also be transmitted to the computer.

A second computer screen may be utilized to display an image of the body tissue immediately ahead of the leading end portion of the tracheal tube. If this is done, the surgeon or other viewer would be able to see an image of body tissue immediately ahead the leading end portion 52*b* of the guide rod 50*b* and an image of body tissue immediately ahead of the leading end portion of the tracheal tube. When simultaneously viewing the two images on two separate screens or on separate portions of a single screen, the surgeon or other viewer would be able to determine the positions of the leading end portions of both the guide rod 50b and the tracheal tube relative to each other and to the respiratory system 11b of a patient.

Although it's preferred to utilize the tracheal tube and it's associated illumination system in conjunction with the guide rod 50b, the tracheal tube may be utilized by itself. Thus, fiber optic tubes which extend through the side wall of the tracheal tube and correspond to the fiber optic tubes 402 and 408 of FIG. 12, would provide an image of the body tissue immediately ahead of the leading end portion of the tracheal tube as the tracheal tube is moved into the patient's respiratory system 11b along an insertion path. The image transmitted from the leading end portion of the tracheal tube to the eye of the viewer or to a display screen would enable a surgeon or other viewer to determine the location of the leading end portion of the tracheal tube relative to the patient's respiratory system 11b.

When the tracheal tube and it's associated illumination and image transmitting systems are utilized without guide rod 50b, the positioning apparatus 56b may be modified to guide movement of the tracheal tube in much the same manner as in which the positioning apparatus 56b is utilized to guide movement of the guide rod 50b. If this is done, colored bands or other indicia could be provided on the tracheal tube to indicate the position of the tracheal tube in the same manner as previously discussed in connection with the guide rods 50 and 250.

It is contemplated that the positioning apparatus 56b may be used for purposes other than tracheal intubation. Thus, the positioning apparatus 56b may be used to position devices other than the guide rod 50b during endoscopic, arthroscopic, or fiber optic surgery at any one of many locations in a patient's body. A magnet, similar to the magnet 260 of FIGS. 4 and 7 may be used to steer a leading end portion of the device being positioned in the patient's body. The leading end portion of the device being positioned in the patient's body may be located at a position adjacent to or spaced a desired distance from a positioning section, corresponding to the positioning section 96b, by the use of suitable indicia, which may be similar to the indicia used in conjunction with the guide rods 50 and 250.

When the positioning apparatus 50b is to be used to position a medicant or a device of any desired type at a selected location in a patient's body, the positioning section 96b is positioned in engagement with a selected portion of the patient's body. The selected portion of the patient's body may be a portion of the patient's body other than the Adam's apple 34b. Although it is believed that it will probably be preferred to engage an exterior surface on the patient's body with the positioning section 96b, the positioning section could be placed in engagement with a surface disposed within the patient's body if desired While the positioning section 96b is engaging the selected portion of the patient's body, the guide rod 50b or a similar elongated member is moved relative to the guide section 114b connected with the arcuate member 108b. The leading end portion 52b of the guide rod 50b or similar elongated member is then moved into the patient's body. The leading end portion 52b may be moved into the patient's body through a naturally occurring opening or through an incision formed in the patient's body.

The image transmitted through the guide rod or similar elongated member 50b to the viewer will indicate when the leading end portion 52b has moved to a desired position in the patient's body. Once the leading end portion 52b of the guide rod or similar elongated member 50b has moved to the desired position relative to the patient's body, any desired procedure may be performed in the patient's body. For example, a surgical procedure could be conducted with one or more devices connected with the leading end portion 52b of the guide rod or similar elongated member. The positioning apparatus 56b may be used to position a therapeutic agent or device at the desired position in the patient's body.

Figure 13:
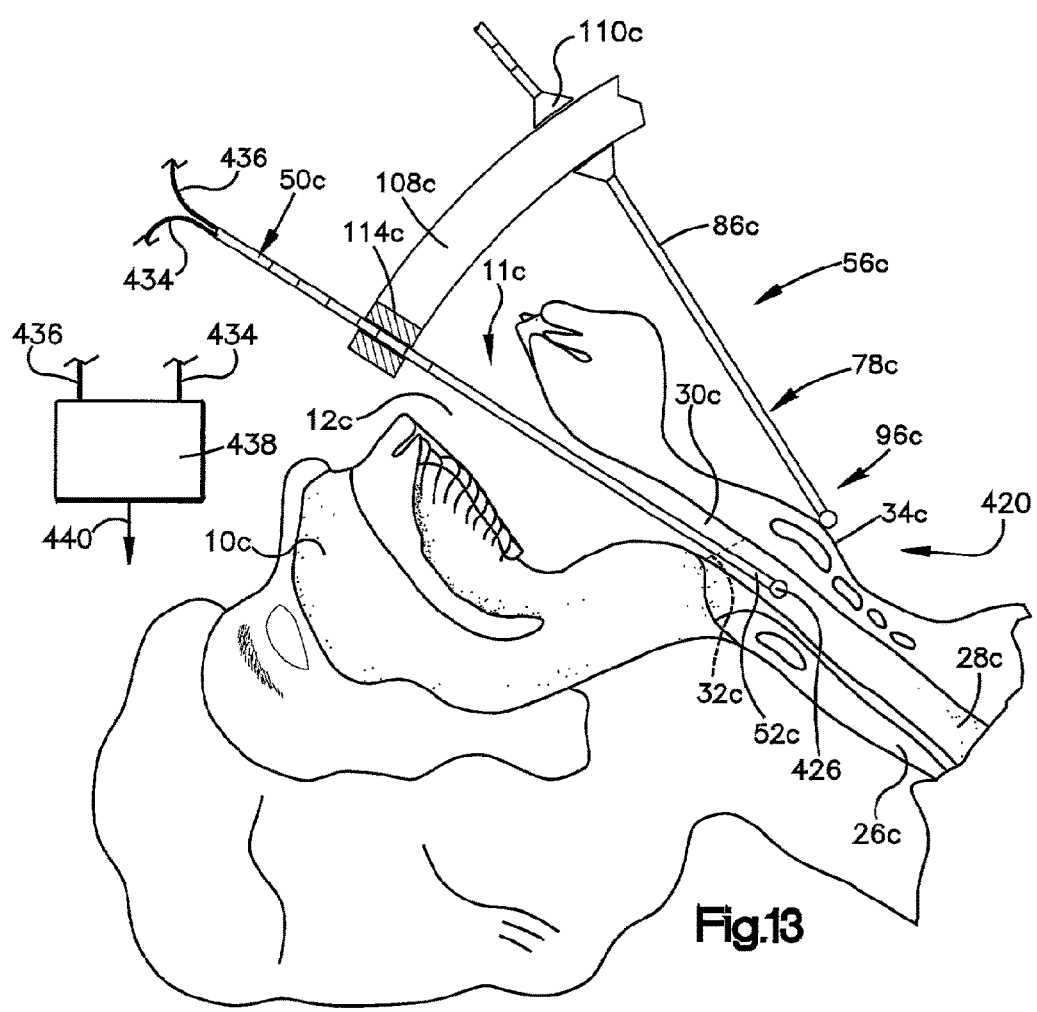
FIG. 13 is a fragmentary schematic illustration, generally similar to FIGS. 1 and 12, of an embodiment of the invention in which a detector on a leading end portion of a guide rod detects emitters disposed on the neck of the patient.
Figure 14:
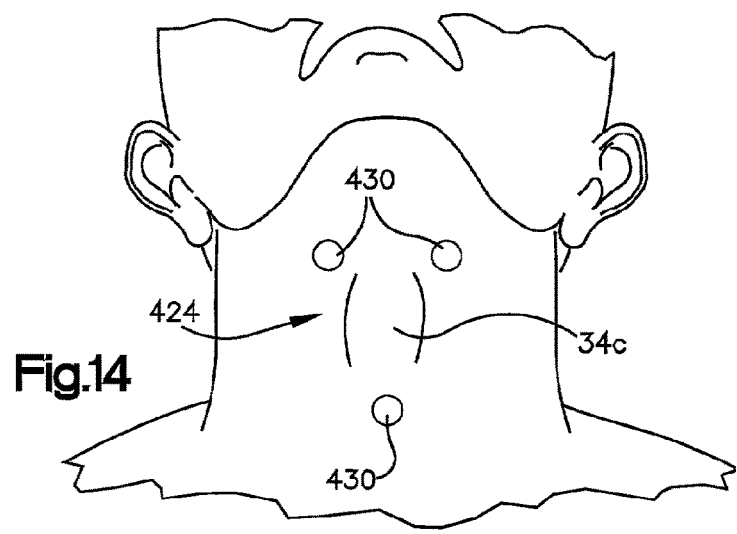
FIG. 14 is a fragmentary schematic illustration, depicting the manner in which a plurality of emitters are arranged in an array around the Adams's apple of the patient of FIG. 13.

Embodiment of FIGS. 13 and 14

In the embodiment invention illustrated in FIG. 12, the light source 400 and fiber optic tube 402 function as an emitter which emits illumination 404 onto body tissue immediately ahead of the leading end portion 52b of the guide rod 50b to facilitate visualization of the body tissue. In the embodiment invention illustrated in FIGS. 13 and 14, a plurality of emitters are positioned adjacent to an outer side surface of the patient's neck. A detector on a leading end portion of a guide rod is moved into the patient's respiratory system. Since the embodiment invention illustrated in FIGS. 13 and 14 is generally similar to the embodiment invention illustrated in FIGS. 1, 2 and 12, similar numerals will be utilized to identify similar components, the suffix letter "c" being associated with the numerals of FIGS. 13 and 14 to avoid confusion A positioning apparatus 56c (FIG. 13) is utilized to position a flexible guide wire or rod 50c relative to a respiratory system 11c of a patient. The respiratory system 11c of the patient extends from the mouth 12c of head 10c through a larynx 30c to a trachea 28c of the patient. The positioning apparatus 56c engages an Adam's apple 34c of a patient to locate the guide rod 50c relative to the patient's respiratory system 11c.

The positioning apparatus 56c has the same general construction and mode operation as the positioning apparatus 56 of FIGS. 1 and 2. The positioning apparatus 56c includes a base section 78c having a body section 86c which is pivotally connected with a positioning section 96c. The positioning section 96c engages an outer surface of the neck of the patient adjacent to the Adam's apple 34c to locate the positioning apparatus 56c relative to the patient's respiratory system 11c. If desired, the positioning apparatus 96c could include a collar which would extend around the patient's Adam's apple 34c in the matter previously described in conjunction with the embodiment invention illustrated in FIG. 7. Alternatively, the positioning apparatus 96c could include a pair of fingers which engage opposite lateral sides of the patient's Adam's apple.

An arcuate member 108c is connected with and is moveable relative to the body section 86c of the positioning apparatus 56c at a connection 110c. A flexible guide rod 50c is axially slidable relative to a guide section 114c which is connected with the arcuate member 108c. The construction of the positioning apparatus 56c is the same as was previously described in conjunction with the embodiment invention illustrated in FIGS. 1 and 2.

In accordance with a feature of the embodiment invention illustrated in FIG. 13, a sensor assembly 420 is provided to inform a surgeon or other user of the positioning apparatus 56c, of the position of the guide rod 50c relative to the patient's respiratory system 11c. The sensor assembly 420 includes an emitter portion 424 (FIG. 14) which provides an output and a detector portion 426 (FIG. 13) which responds to the output from the emitter portion 424. In the embodiment of invention illustrated in FIGS. 13 and 14, the emitter portion 424 is positioned on an outer side surface of the neck of the patient adjacent to the Adam's apple 34c. The detector portion 426 is connected with a leading end portion 52c of a guide rod 50c. However, it should be understood that the emitter portion 424 could be connected with the guide rod 50c and the detector portion 426 positioned adjacent to the Adam's apple 34c of the patient.

In the illustrated embodiment invention, the emitter portion 424 of the sensor assembly 420 includes a plurality of emitters units 430 which are positioned an array which extends around the Adam's apple 34c (FIG. 14) of the patient. The emitter units 430 are secured to the neck of the patient by a suitable adhesive. The emitter units 430 may be positioned in any desired spatial relationship with the patient's Adam's apple 34c.

Alternatively, the emitter units 430 may be connected with the positioning section 96c. Thus, the positioning section 96c of the positioning apparatus 56c is provided with three fingers which engage the neck of the patient adjacent to the Adam's apple 34c. Each of the emitter units 430 may be connected with one of the fingers of the positioning section 96c. The positioning section 96c would accurately locate the emitter units 430 relative to the patient's Adam's apple 34c.

In the embodiment of the invention illustrated in FIG. 13, the positioning section 96c engages the Adam's apple 34c and the emitter units are disposed in a generally circular array which extends around the Adam's apple 34c. However, it should be understood that the emitter units 430 could be connected with a collar, similar to the collar 306 of FIG. 7. The collar may be connected with the positioning section 96c (FIG. 13). Alternatively, the collar could be separate from the positioning apparatus.

Although it is preferred to utilize the positioning apparatus 56c in conjunction with the guide rod 50c, in the manner previously described in conjunction with the embodiment of the invention illustrated in FIG. 1, it is contemplated that the positioning apparatus 56c may be omitted and the guide rod 50c moved along an insertion path into the patient's respiratory system without benefit of the assistance provided by the positioning apparatus. If this is done, the emitter units 430 (FIG. 14) could be connected with a support structure which holds the emitter units 430 in a fixed relationship relative to each other and facilitates positioning of the emitter units relative to the patient's Adam's apple 34c. For example, a positioning section having a plurality of fingers, could be manually centered on the patient's Adam's apple 34c to locate the emitter units 430 relative to the Adam's apple. Similarly, a collar, corresponding to the collar 306 of FIG. 7, could be provided on a circular or oval support which would extend around the patient's Adam's apple 34c to locate the emitter units 430 relative to the patient's Adam's apple. Regardless of the specific structure which is utilized to position the emitter units 430 relative to each other, this apparatus could be manually positioned relative to the patient's Adam's apple 34c without being connected with a positioning apparatus having a construction similar to the construction of the positioning apparatus 56c.

When the positioning apparatus 56c is to be utilized to assist in the positioning of the guide rod 50c relative to the patient's respiratory system 11c, the positioning section 96c is positioned in engagement with the patient's Adam's apple 34c. The emitter units 430 may be suitably mounted on the positioning section 96c. This would locate the emitter units 430 relative to the patient's Adam's apple 34c (FIG. 14). It should be understood that the emitter units 430 could be mounted on a support other than the positioning section 96c if desired. Of course, the emitter units 430 may be secured directly to the neck of the patient by a suitable adhesive, as illustrated in FIG. 14. When this is done, a support structure interconnecting the emitter units 430 may be used to facilitate positioning of the emitter units relative to the patient's Adam's apple 34c.

The arcuate member 108c is then positioned axially along the body section 86c. When the arcuate member 108c has been moved to a desired position relative to the body section 86c, the connection 110c is secured to hold the arcuate member against axial movement along the body section. The arcuate member 108c is then moved relative to the body section 86c to position the guide section 114c and the leading end portion 52c of the guide rod 50c in alignment with the entrance to the patient's mouth 11c. The guide rod 50c is then moved into the patient's respiratory system 11c along an insertion path.

As the guide rod 50c is moved along the insertion path into the patient's respiratory system 11c, the detector portion 426 of the sensor assembly 420 approaches the emitter units 430. As this occurs, the detector portion provides an output over leads 434 and 436 to a computer or micro processor 438. The computer or micro processor has an output, indicated schematically at 440, which can be viewed by a surgeon or other individual moving the guide rod 50c along the insertion path into the patient's respiratory system 11c.

The computer output may include a display having a schematic illustration of a typical patient's respiratory system. The positions of the emitter units 430 relative to the typical respiratory system and the position of the detector portion 426 relative to the emitter units 430 would be indicated on the display. Thus, a display screen connected with the computer 438 has an illustration representative of the patient's respiratory system 11c. A plurality of indicators are provided on the display screen to indicate the positions of the emitter units 430 relative to the schematic illustration of the patient's trachea. An indicator is provided to indicate the position of the leading end of the guide rod 50c relative to the schematic illustration of the patient's respiratory system. The display screen has one illustration of the patient's respiratory system 11c as viewed in a medial plane and another illustration of the patient's respiratory system as viewed in a frontal plane. Indicators corresponding to the emitter units 430 and detector 426 are provided in both illustrations.

As the leading end portion 52c of the guide rod 50c moves along the insertion path into the patient's respiratory system 12c, the detector portion 426 of the sensor assembly 420 approaches the emitter portion 424 of the sensor assembly. As this occurs, the strength of the output from the detector portion 426 through the leads 434 and 436 increases. As the strength of the output from the detector portion 426 increases, the computer and the associated display indicates to an operator of the apparatus 56c that the leading end portion 52c of the guide rod 50c is approaching a junction between the patient's esophagus 26c and the pharynx.

If the guide rod continues movement along its intended course of insertion, that is, into the patient's larynx 30c and not into the patient's esophagus 26c, the strength of the output signal provided by the detector portion 426 will increase. However, if the leading end portion 52c of the guide rod 50c enters the patient's esophagus 26c, the strength of the output signal from the detector portion 426 will decrease. The decreasing strength of the signal from the detector portion 426 provides a clear indication to the operator of the apparatus 56c that the leading end portion 52c of the guide rod 50c has deviated from its intended course.

As the detector portion 426 of the sensor assembly 420 moves between the patient's vocal chords 32c into alignment with the emitter portion 424 of the sensor assembly 420, the strength of the signal transmitted to the computer 438 will be maximized. As the guide rod 50c continues to be moved into the patient's trachea 28c along the insertion path, the strength of the signal transmitted through the leads 434 and 436 to the computer 438 will decrease to indicate to the operator of the apparatus 56c that the leading end portion 52c of the guide rod has moved past the patient's Adam's apple 34c.

Although it is believed that it will be preferred to display the output of the computer 438 in association with one or more illustrations of the patient's respiratory system 11c in the manner previously mentioned, the computer output information could be transmitted in a different manner if desired. For example, the computer 438 could have a light display system which indicates how close the detector 426 is to the emitter units 430. Similarly, the computer 438 could have an audio output which indicates how close the detector 426 is to the emitter units. Of course, the computer could have an output which is a combination of a display screen, lights and/or audio signals.

Once the guide rod 50c has been moved to the desired position along the patient's respiratory system 11c, the positioning apparatus 56c may be disconnected from the guide rod 50c. A tracheal tube, corresponding to tracheal tube 38 of FIG. 2, is then moved along the guide rod 50c into the patient's trachea 28c. The manner in which the tracheal tube is moved along the guide rod 50c into the patient's trachea 28c is the same as was previously discussed in conjunction with the embodiment of the invention illustrated in FIGS. 1 and 2. A magnet, corresponding to the magnet 260 of FIGS. 4 and 7, may be utilized to steer the leading end portion of the guide rod 50c. If desired, an electromagnet which can be turned on and off may be utilized.

The tracheal tube which is utilized in association with the guide rod 50c of FIG. 13 may have the same construction as the tracheal tube 38 utilized with the guide rod 50 of FIG. 2. Alternatively, the tracheal tube utilized with the guide rod 50c may have a second detector portion, having the same construction as the detector portion 426 of the guide rod 50c. If the tracheal tube is provided with a second detector portion, the emitter portion 424 of the sensor assembly 420 is maintained in position relative to the patient's Adam's apple 34c.

By providing the tracheal tube with a second detector portion, and by maintaining the emitter portion 424 in position relative to the patient's Adam's apple 34c, the output from the second detector portion may be utilized to locate the leading end portion of the tracheal tube as the tracheal tube is moved along the guide rod 50c into the patient's respiratory system 11c. If this is done, leads, corresponding to the leads 434 and 436 would extend along the side wall of the tracheal tube from the second detector portion to the computer 438. The output from the computer 438 would indicate the position of the leading end portion of the tracheal tube relative to the emitter 424. The output from the second detector portion on the leading end portion of tracheal tube would indicate the position of the leading end portion of the tracheal tube relative to the position of the leading end portion of the guide rod 50c.

The output from the computer may be a display having the construction previously described in conjunction with the guide rod 50c. Thus, a display screen connected with the computer 438 has an illustration representative of the patient's respiratory system 11c. A plurality of indicators are provided on the display screen to indicate the positions of the emitter units 430 relative to the patient's trachea. An indicator is provided to indicate the position of the leading end of the tracheal tube relative to the patient's respiratory system. The display screen has one illustration of the patient's respiratory system 11c as viewed in a medial plane and another illustration of the patient's respiratory system as viewed in a frontal plane. Indicators corresponding to the emitter units 430 and detector on the tracheal tube are provided in both illustrations.

In the embodiment of the invention illustrated in FIGS. 13 and 14, the emitter units 430 are magnets which emit a magnetic field. The detector portion 426 is a magnetometer which responds to variations in the strength of a magnetic field. Thus, the output from the detector portion 426 increases as the detector portion moves closer to the patient's Adam's apple 34c and the magnets forming the emitter units 430. The detector portion 436 may be Hall effect device, magnetoresistor, or a galvanometer device. Regardless of what specific type of magnetic field responsive device is utilized to form the detector portion 426 of the sensor assembly, the output from the detector portion will vary as the distance between the leading end portion 52c of the guide rod 50c and the magnets in the emitter units 430 varies.

In the embodiment of the invention illustrated in FIGS. 13 and 14, the sensor assembly 420 is the type which responds to a magnetic field. However, it is contemplated that the sensor assembly 420 could be constructed so as to respond to other types of emissions. For example, light sources could be utilized as the emitter units 430 and the detector portion 436 may be a photo cell which responds to variations in the amount of light received. Alternatively, the emitter units 430 could be sources of radio frequency radiation and the detector portion 426 could be constructed so as to have an output which varies as the distance between the detector portion and the sources of radio frequency radiation varies. If desired, the emitter units 430 could be ultrasonic transducers and the detector 426 could respond to ultrasonic energy.

The sensor assembly 420 has been illustrated in FIGS. 13 and 14 in association with the positioning apparatus 56c. However, it should be understood that the sensor assembly 420 could be utilized in association with the positioning apparatus 256 of FIGS. 4-10 or the positioning apparatus 256a of FIG. 11. If this was done, the use of the magnet 260 or 260a (FIGS. 4, 7 and 11) may be eliminated to avoid interference with magnetic fields from the emitter units 430. Of course, if the emitter units provided outputs which were not affected by the magnetic field from the magnets 260 and 260a, the magnets 260 and 260a could still be utilized.

The positioning apparatus 56c and sensor assembly 420 have been illustrated in association with a tracheal intubination procedure. It is contemplated that the positioning apparatus 56c and/or sensor assembly 420 may be used in association with other medical procedures if desired. For example, the positioning apparatus 56c and/or sensor assembly 420 may be used in the performance of endoscopic, arthroscopic or fiber optic surgical procedures. The positioning apparatus 56c and/or sensor assembly 420 may be used in association with surgery on joints or other portions of a patient's body. The positioning apparatus 56c and/or sensor assembly 420 may be used to deliver medicants to a desired location in a patient's body Embodiments of FIGS. 15 and 16

Figure 15:
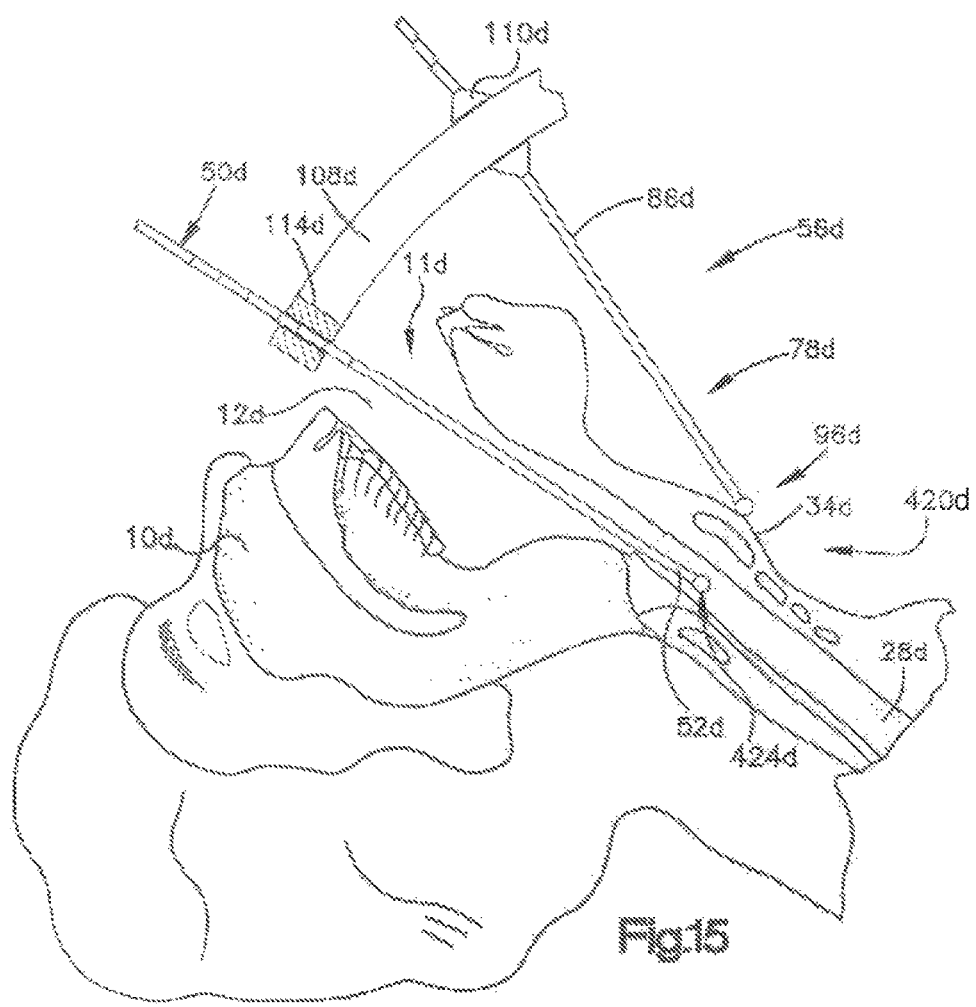
FIG. 15 is a fragmentary schematic illustration, generally similar to FIG. 13, of an embodiment of the invention in which detectors on the neck of the patient detect an emitter on a leading end portion of the guide rod.
Figure 16:
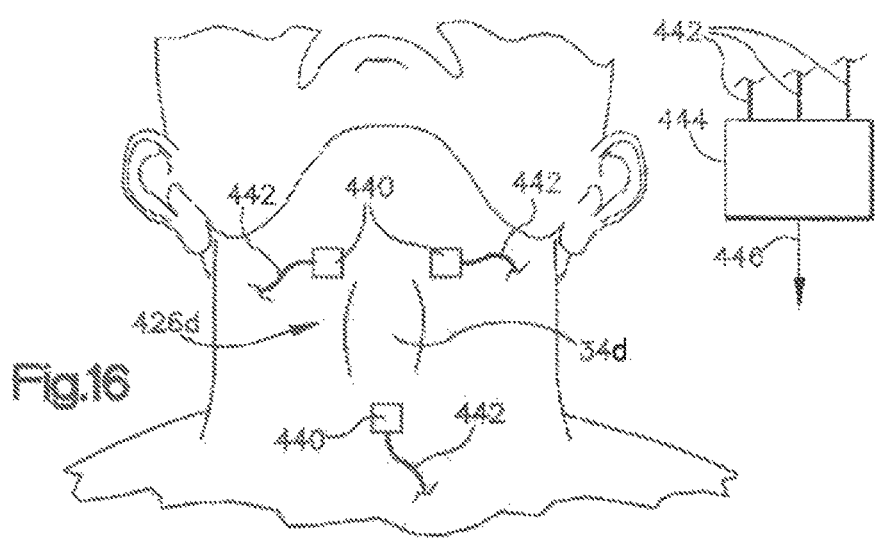
FIG. 16 is a fragmentary schematic illustration, generally similar to FIG. 14, illustrating a manner in which a plurality of detectors are positioned in an array around the Adam's apple on the neck of the patient of FIG. 15.

In the embodiment of the invention illustrated in FIGS. 13 and 14, the emitter portion 424 of the sensor assembly 420 is disposed adjacent to the outer surface of the neck of the patient while the detector portion 426 of the sensor assembly is connected with the guide rod 50c. In the embodiment of the invention illustrated in FIGS. 15 and 16, the detector portion of the sensor assembly is disposed adjacent to the outer surface of the patient's neck and the emitter portion of the sensor assembly is connected with the leading end portion of the guide rod. Since the embodiment of the invention illustrated FIGS. 15 and 16 is generally similar to the embodiment of the invention illustrated in FIGS. 1, 2, 13 and 14, similar numerals will be utilized to identify similar components, the suffix letter "d" being associated with the numerals of FIGS. 15 and 16 to avoid confusion.

The positioning apparatus 56d is utilized to position a flexible guide rod 50d relative to a patient's respiratory system 11d. The positioning apparatus 56d includes a base section 78d having a body section 86d and a positioning section 96d. An arcuate member 108d is connected with the body section 86d at a connection 110d. When the arcuate member 108d has been moved to a desired position along the base section 86d, the connection 110d is actuated to hold the member 108d against axial movement along the body section 86d. When the guide section 114d has been moved into alignment with the patient's mouth 12d, the connection 110d is again actuated to hold the arcuate member 108d against movement relative to the base section 86d.

The guide section 114d cooperates with the flexible guide rod 50d to position the guide rod during movement of the guide rod into the patient's respiratory system 11d along an insertion path. The general construction and mode of operation of the positioning apparatus 56d is the same as was previously described in conjunction with the positioning apparatus 56 of FIGS. 1 and 2.

In accordance with a feature of this embodiment of the invention, a sensor assembly 420d is provided to sense when the guide rod 50d has moved to a desired position relative to the patient's respiratory system 11d. The sensor assembly 420d includes a detector portion 426d (FIG. 16) and an emitter portion 424d (FIG. 15).

The sensor portion 426d of the sensor assembly 420d is positioned on the outer surface of a neck of a patient (FIG. 16) adjacent to the patient's Adam's apple 34d. The emitter portion 424d is connected with a leading end portion 52d of the guide rod 50d (FIG. 15). The sensor portion 426d (FIG. 16) is mounted directly on the patient's neck by a suitable adhesive. However, if desired, the sensor portion 426d could be connected with the positioning section 96d of the positioning apparatus 56d. If this is done, when the positioning section 96d of the positioning apparatus 56d is positioned in engagement with the patient's Adam's apple 34d, the sensor portion 426 of the sensor assembly 420d would also positioned relative to the patient's Adam's apple. However, if desired, the sensor portion 426d could be mounted on a support and positioned relative to the patient's Adam's apple 34d independently of the positioning section 96d of the positioning apparatus 56d.

The sensor portion 426d of the sensor assembly 420d includes a plurality of sensor units 440 which are disposed in an array around the patient's Adam's apple 34d (FIG. 16). The sensor units 440 have leads 442 which are connected with a computer or micro processor 444. The computer or micro processor 444 has an output, indicated schematically in 446 in FIG. 16, which is indicative of the position of the emitter portion 424d of the sensor assembly 420d relative to the position of the sensor portion 426d of the sensor assembly. The emitter portion 424d of the sensor assembly 420d is connected with the leading end portion 52d of the guide rod 50d.

During use of the positioning apparatus 56d, the leading end portion 52d of the flexible guide rod 50d is aligned with the mouth 12d of head 10d of the patient. The guide rod 50d is then moved into the patient's respiratory system 11d along an insertion path. As the guide rod 50d is moved into the patient's respiratory system 11d, the emitter portion 424d of the sensor assembly 420d approaches the sensor portion 426d of the sensor assembly 420d. As this occurs, the strength of the output from the sensor units 440 increases.

The increasing strength of the output from the sensor units 440 results in a change in the output 446 from the computer 444. The output 446 from the computer 444 may take the form of a display which schematically indicates the position of the emitter portion 424d of the sensor assembly 420d relative to the sensor portion 426d of the sensor assembly. Thus, a display screen for the computer 444 may have a schematic illustration representative of a typical patient's respiratory system. The display screen would indicate the position of the sensor portion 426d of the sensor assembly 420d relative to the patient's respiratory system and the position of the emitter portion 424d of the sensor assembly 420d relative to the patient's respiratory system. Since the emitter portion 424d is connected with the leading end portion 52d of the guide rod 50d, the display for the computer 444 would indicate the position of the leading end portion 52d of the guide rod relative to the patient's Adam's apple 34d.

Although it is believed that the use of a display screen may be preferred, the output 446 from the computer 444 could take a different form if desired. For example, the computer could have an audio output. Alternatively, a display graph formed of a series of lights could provide a visual output. As the emitter portion 424d approaches the sensor units 440, the number of illuminated lights in the series of lights would increase. When the emitter portion 424d is aligned with the center of the array of sensor units 440 and the patient's Adam's apple 34d, the entire series of lights would be illuminated. Of course, the output 446 from the computer 444 could include both audio and visual outputs.

In the embodiment of the invention illustrated in FIGS. 15 and 16, the emitter portion 424d of the sensor assembly 420d is a magnet which emits a magnetic field. The sensor portion 426d of the sensor assembly 420d has an output which varies as a function of the strength of the magnetic field at the sensor units. Therefore, as the leading end portion 52d of the guide rod 50d approaches the patient's Adam's apple 34d, the strength of the magnetic field to the sensor units 440 increases and the output transmitted to the computer 444 increases.

In the specific embodiment of the invention illustrated in FIG. 16, the sensor units 440 are Hall effect devices. However, it is contemplated that other known devices which respond to variations in a magnetic field may be utilized in place of the Hall effect devices which form the sensor units 440. For example, magnetoresistors could be utilized as the sensor units 440 in place of the Hall effect devices.

Once the guide rod 50d has been positioned relative to the patient's respiratory system 11d, the positioning apparatus 56d is disconnected from the guide rod 50d while the guide rod is maintained stationary relative to the patient's respiratory system 11d. A flexible tracheal tube, corresponding to the tracheal tube 38 of FIG. 2, is then moved along the guide rod 50d into the patient's respiratory system 11d. The manner of insertion of the tracheal tube into the patient's respiratory system 11*d*, by sliding the tracheal tube along the guide rod 50*d*, is the same as was previously described in conjunction with the embodiment of the invention illustrated in FIG. 2.

It is contemplated that the sensor portion 426*d* of the sensor assembly 420*d* can be utilized in association with the tracheal tube. Thus, the tracheal tube can be provided with a second emitter portion having the same construction as the emitter portion 424*d*. In the embodiment of the invention illustrated in FIGS. 15 and 16, a magnet, which emits a magnetic field, would be mounted on a leading end portion of the tracheal tube.

As the tracheal tube having an emitter, is moved along the guide rod 50*d*, the magnet on the leading end portion of the tracheal tube would have an effect on the sensor units 440. The effect on the magnet on the sensor units 440 increases as the leading end portion of the tracheal tube approaches the patient's Adam's apple 34*d*. It is contemplated that the tracheal tube may be inserted into the patient's trachea 28*d* further than the guide rod 50*d*. If this is done, the output from the sensor units 440*d* diminishes in magnitude as the leading end portion of the tracheal tube is moved down the patient's trachea past the sensor units.

Although it is preferred to utilize the sensor assembly 420*d* in association with the positioning apparatus 56*d*, the sensor assembly could be utilized separately from the positioning apparatus. For example, the sensor units 440 may be mounted in an array on a separate support structure. The support structure would be positioned in an engagement with the exterior of the patient's neck with the array of sensor units 440 centered about the patient's Adam's apple, in the manner illustrated schematically in FIG. 16.

The guide rod 50*d* would then be moved along the patient's respiratory system 11*d* without benefit of the positioning apparatus 56*d*. As the guide rod 50*d* moves along the patient's respiratory system 11*d*, the strength of the magnetic field from the emitter portion 424*d* of the sensor assembly 420*d* detected by the sensor units 440 would increase. This would result in an increase in the output from the sensor units 440 to the computer 444. The output 446 from the computer 444 would indicate to the operator moving the guide rod 50*d*, the position of the guide rod along an insertion path into the patient's respiratory system 11*d*.

Once the guide rod 50*d* has been positioned in the foregoing manner relative to the patient's respiratory system 11*d*, without benefit of the positioning apparatus 56*d*, the tracheal tube would be moved along the guide rod into the patient's respiratory system 11*d*. The tracheal tube could have the same construction and move in the same manner as the tracheal tube 38 of FIG. 2.

Alternatively, the tracheal tube could be provided with a second emitter portion, corresponding to the emitter portion 424*d* of the sensor assembly 420. Thus, a magnet could be provided on the leading end portion of the tracheal tube. As the leading end portion of the tracheal tube moves along the insertion path into the patient's respiratory system 11*d*, the magnetic field detected by the sensor units 440 would increase due to the magnet connected with the leading end portion of the tracheal tube approaching the magnet on the leading end portion 52*d* of the guide rod 50*d*.

It is also contemplated that the tracheal tube could be positioned relative to the patient's respiratory system 11*d* without benefit of the guide rod 50*d*. The tracheal tube would be provided with an emitter corresponding to the emitter 424*d*. As tracheal tube is moved into the patient's respiratory system 11*d* without benefit of the guide rod 50*d*, the output from the emitter connected to the leading end portion of the tracheal tube would be detected by the sensor units 440. The output from the sensor units 440 would indicate the position of the leading end portion of the tracheal tube relative to the patient's respiratory system 11*d*.

In the embodiment of the invention illustrated in FIGS. 13-16, magnets have been utilized as emitter units. The magnets which form the emitter portion 424 of the sensor assembly 420 are permanent magnets formed of a strongly magnetizable material such as cobalt or neodymium. Of course, other know magnetizable materials having saturation magnetization values, such as cerium, praseodymium and or samarium with cobalt and/or other materials could be used. Alternatively, the magnets in the emitter portion 424 (FIG. 14) and 424*d* (FIG. 15) could be electromagnets.

The detector portion 426 (FIG. 13) and 426*d* (FIG. 16) of the sensor assemblies 420 and 420*d* may be any known device which respond to changes in the strength and/or direction of a magnet field. For example, the detector portions 426 include one or more Hall effect devices and/or one or more magnetoresistors.

Although the emitter portions 424 and 424*d* of the sensor assemblies 420 and 420*d* have been described herein as emitting magnetic fields, it is contemplated that the emitter portions 424 and 424*d* could have outputs other than a magnetic field. For example, the emitter portions 424 and/or 424*d* (FIGS. 14 and 15) could be miniaturized radio frequency devices. Thus, the emitter portions of the sensor assemblies could be formed by radio signal transmitters having miniaturized radio circuitry which provide a radio frequency output signal. If a radio frequency transmitter is utilized in the emitter portion 424 or 424*d* of the sensor assemblies, the sensor portion 426 or 426*d* would be a radio frequency receiver. The radio frequency receiver could include a receiving antenna which receives radio frequency signals. The field of the antenna may be controlled by appropriate placement, orientation, and/or configuration of the antenna.

Alternatively, the emitter portions 424 and 424*d* could emit ultrasonic energy. The sensor portion 426 or 426*d* would respond to ultrasonic energy.

Figure 17:
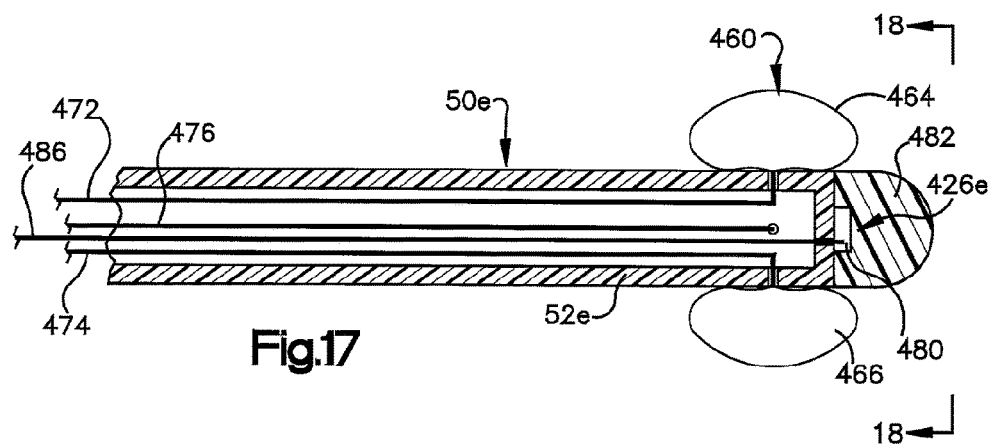
FIG. 17 is an enlarged schematic fragmentary sectional view of the leading end portion of a guide rod on which a detector and a plurality of expandable steering elements are disposed.
Figure 18:
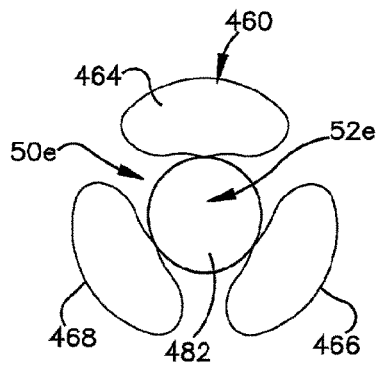
FIG. 18 is a plan view, taken generally along the line 18-18 of FIG. 17, further illustrating the relationship of the expandable steering elements to the leading end portion of the guide rod.

Embodiment of FIGS. 17 and 18

In the embodiment of the invention illustrated in FIGS. 13 and 14, the sensor assembly 420 includes a detector portion 426 which is disposed on the leading end portion 52*c* of the guide rod 50*c* and responds to a magnetic field. The operator of the positioning apparatus 56*c* is informed, by a display system connected with the computer 438, of the position of the leading end portion 52*c* of the guide rod 50*c* relative to the patient's respiratory system 11*c*. In the embodiment of the invention illustrated in FIG. 17 an 18, the leading end portion of the guide rod is steerable to enable the other operator to alter the course of movement of the leading end portion of the guide rod to maintain the leading end portion of the guide rod on a desired insertion path into the patient's respiratory system. Since the embodiment of the invention illustrated in FIGS. 17 and 18 is generally similar in the embodiment of the invention illustrated in FIGS. 13-16, similar numerals will be utilized to designate similar components, the suffix letter "e" being associated with the numerals of FIGS. 17 and 18 to avoid confusion.

The embodiment of the invention illustrated in FIGS. 17 and 18 is utilized with a positioning apparatus having the same construction as the positioning apparatus of FIGS. 1, 2, and 13-16. However, the embodiment of the invention illustrated in FIGS. 17 and 18 could be used with the positioning apparatus 256 and/or 256*a* of FIGS. 4-11 if desired. The guide rod 50e of FIGS. 17 and 18 is provided with a steering apparatus 460. The steering apparatus 460 is operable to change the course of movement of the leading end portion 52e of the flexible guide rod 50e as the guide rod moves along the insertion path into the patient's respiratory system.

The steering apparatus 460 applies force against body tissue in the patient's respiratory system to deflect the leading end portion 52e of the flexible guide rod 50e away from an undesired course of movement. For example, when the leading end portion of the guide rod 50e is approaching a junction between the patient's esophagus 26 (FIG. 1) and trachea 28, the steering apparatus 460 (FIGS. 17 and 18) may be activated to deflect the leading end portion 52e of the guide rod 50e away from the entrance to the patient's esophagus. Similarly, when the leading end portion 52e of the guide rod 50e is approaching the larynx 30, the steering apparatus 460 may be activated to align the leading end portion 52e of the guide rod with an opening between vocal chords in the patient's larynx.

In the illustrated embodiment of the invention, the steering apparatus 460 includes a plurality of expandable elements 464, 466 and 468 (FIG. 18). Although three expandable elements 464-468 have been illustrated as being disposed in a circular array about the leading end portion 52e of the guide rod 50e, a greater or lesser number of expandable elements could be provided in association with the leading end portion of the guide rod if desired.

The expandable elements 464, 466 and 468 are individually activatable so that one, two or all three of the expandable elements can be expanded. For example, just the expandable element 464 (FIG. 18) may be expanded to apply force against the leading end portion 52e of the guide rod 50e to move the guide rod downward (as viewed in FIG. 18) relative to a path of movement of the guide rod through the patient's respiratory system. Alternatively, the expandable elements 466 and 468 may be expanded at the same time to deflect the leading end portion 52e of the guide rod 50e upward (as viewed in FIG. 18). It is believed that it may be desired to center the leading end portion 52e of the guide rod 50e in a passage in the patient's respiratory system. When this is to be done, all three expandable elements 464, 466, and 468 would be expanded.

In the illustrated embodiment of the invention, the expandable elements 464, 466 and 468 are balloons or bladders which are expanded under the influence of fluid pressure, that is, under the influence of either a gas or a liquid. To enable the expandable elements 464, 466 and 468 to be individually expanded, conduits 472, 474 and 476 are each connected in fluid communication with one of the expandable elements 464, 466 or 468. For example, when the expandable element 464 is to expanded, fluid under pressure is connected through the conduit 472 to the expandable element 464. Similarly, when the expandable element 466 is to expanded, fluid under pressure is connected through the conduit 474 to the expandable element 466. Finally, when the expandable element 468 is to be expanded, fluid under pressure is connect through the conduit 476 to the expandable element 468

After one or more of the expandable element 464-468 have been expanded to steer the leading end portion 52e of the guide rod 50e, the expandable elements 464, 466 and/or 468 are contracted. This may be accomplished by connecting the conduits 472, 474 and/or 476 with a source of suction or low pressure. The expandable elements 464, 466 and 468 are contracted under the influence of their own natural resilience. If desired, springs could be provided in association with the expandable elements to contract the expandable elements 464-468.

The contracted expandable elements 464, 466 and 468 are disposed in engagement with an outer side surface of the leading end portion 52e of the guide rod 50e. If desired, recesses could be provided in the leading end portion of the guide rod 50e to receive each of the expandable elements 464, 466 and 468 when the expandable elements are in their contracted condition.

It is believed that it will be preferred to form the expandable elements 464, 466 and 468 of a resiliently stretchable polymeric material so that the expandable elements can be expanded, under the influence of fluid pressure, by stretching the material of the expandable elements. When the expandable elements are to be deflated, the resiliently stretched elastomeric material of the expandable elements 464-468 will tend to force fluid out of the expandable elements and cause them to return to their contracted conditions. When the retracted, the expandable elements 464, 466 and 468 are disposed in either separate recesses or a single annular recess which extends around the leading end portion of the guide rod 50e. The contracted expandable elements do not project outward from the outer side surface of the guide rod 50e. Alternatively, the contracted expandable elements 464-468 could be contracted, under the influence of their own natural resilience, into tight abutting engagement with the outer side surface of the guide rod 50e.

It is contemplated that the conduits 472, 474 and 476 and expandable elements 464, 466 and 468 may be formed in a manner similar to that disposed in U.S. patent application Ser. No. 08/470,142 filed Jun. 6, 1995 by Peter M. Bonutti et al. and entitled Method Of Using Expandable Cannula. The disclosure of the aforementioned application Ser. No. 08/470,142 is hereby incorporated herein in its entirety by this reference thereto. Alternatively, the expandable elements 464, 466 and 468 could be formed in manners similar to that disclosed in U.S. Pat. Nos. 3,833,003 and/or 5,197,971.

Although the illustrated expandable elements 464-468 are expanded under the influence of fluid pressure, they could be expanded in a different manner if desired. For example, mechanical actuators could be provided. The mechanical actuators may be utilized to move members which are not balloons.

In order to enable an operator of the positioning apparatus to determine the location of the leading end portion 52e of the guide rod 50e relative to the patient's respiratory system, a sensor assembly, similar to the sensor assembly 420 of FIGS. 13 and 14, is utilized in association with the steering apparatus 460. In the embodiment of the invention illustrated in FIG. 17, the detector portion 426e of the sensor assembly includes a detector 480 which responds to an output from an emitter portion of the sensor assembly. The detector 480 is enclosed by a soft dome or cap 482 which forms part of the leading end portion 52e of the guide rod 50e. The dome or cap 482 cushions engagement of the leading end portion 52e of the guide rod 50e with body tissue along the patient's respiratory system. In addition, the dome 482 protects the detector portion 426e.

The detector 480 may be a Hall effect device which cooperates with emitters, which are magnets, in the manner described in conjunction with FIGS. 13 and 14. Alternatively, the detector 480 may respond to radio frequency radiation. If desired, the detector 480 could be constructed so as to respond to ultrasonic energy. Rather than providing a detector 480 on the leading end portion 52e of the guide rod 50e, an emitter could be provided in the manner described in conjunction with FIGS. 15 and 16.

The detector portion 426e (FIG. 17) is connected with a computer, similar to the computer 438 of FIG. 13, by a lead 486 (FIG. 17). The output from the computer indicates to an operator the position of the leading end portion 52e of the guide rod 50e relative to the patient's respiratory system. The output of the computer will also indicate to the operator when the leading end portion 52e of the guide rod 50e may deviate from the intended course of insertion of the guide rod into the patient's respiratory system.

When the output from the computer indicates that the leading end portion of the guide rod may not move along the intended insertion path, the operator may initiate expansion of one or more of the expandable elements 464-468. The expandable elements will apply force against the patient's body tissue and against the leading end portion 52e of the guide rod 50e to deflect the guide rod in such a manner as to maintain the guide rod on its intended insertion path into the patient's respiratory system.

As was previously described in conjunction with the embodiments of the invention illustrated in FIGS. 13-16, a visual display system, illustrative of the patient's respiratory system, may be connected with the computer which receives the output from a sensor assembly 420 or 420d. By viewing an illustration depicting the location and path of movement of the leading end portion 52e of the flexible guide rod 50e, an operator will know when to expand one or more of the expandable elements 464, 466 and 468.

It is contemplated that the steering apparatus 460 and position sensing assembly may be used with devices for purposes other than tracheal intubination. For example, the steering apparatus 460 and position sensing assembly used with the guide rod 50e of FIG. 17 could be used in association with a device which is used to position medicant at a selected location in a patient's body. It is also contemplated that the steering apparatus 460 and position sensing assembly could be used in conjunction with endoscopic, arthroscopic, or fiber optic surgery.

Figure 19:
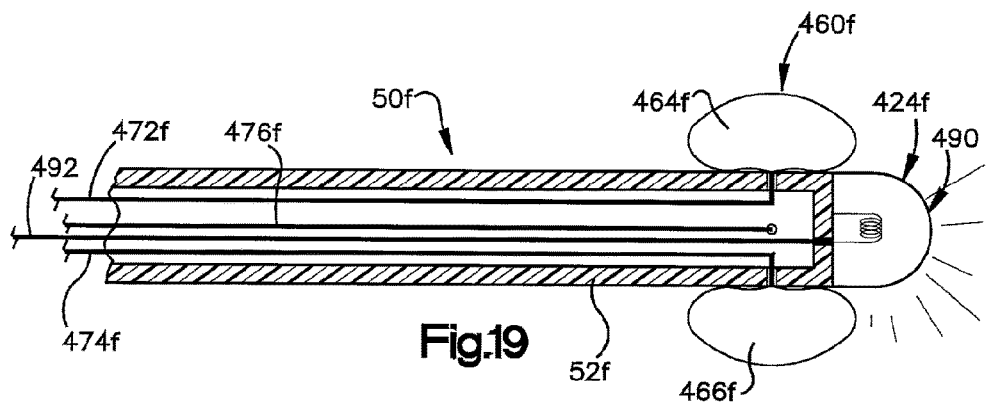
FIG. 19 is a schematic fragmentary sectional view of a leading end portion of a guide rod on which an emitter and a plurality of expandable steering elements are disposed.

Embodiment of FIG. 19.

In the embodiment of the invention illustrated in FIGS. 17 and 18, the steering apparatus 460 is disclosed in conjunction with the guide rod 50e which is used with a sensor assembly, corresponding with the sensor assembly 420 of FIG. 13, in which the detector portion is disposed on the leading end portion 52e of the guide rod. In the embodiment of the invention illustrated in FIG. 19, the steering apparatus is disposed in association with a guide rod having an emitter portion of a sensor assembly disposed on the leading end portion of the guide rod in the manner illustrated in FIGS. 15 and 16. Since the embodiment of the invention illustrated in FIG. 19 is generally similar to the embodiments of the invention illustrated in FIG. 13-18, similar numerals will be utilized to designate similar components, the suffix letter "f" being associated with the numerals of FIG. 19 in order to avoid confusion.

A guide rod 50f has a leading end portion 52f. The guide rod 50f is used with a positioning apparatus similar to the positioning apparatus 56d of FIG. 15. The flexible guide rod 50f (FIG. 19) is associated with a sensor assembly corresponding to the sensor assembly 420d of FIG. 15. Thus, the guide rod 50f has an emitter portion 424f (FIG. 19) which is connected with the leading end portion 52f of the guide rod. The output from the emitter portion 424f is detected by suitable detectors disposed adjacent to the exterior surface of the patient's neck and to the patient's Adam's apple, in the manner illustrated schematically in FIG. 16.

In the embodiment of the invention illustrated in FIG. 19, the emitter portion 424f includes a light source 490. The light source 490 is connected with source of electrical energy by a lead 492. The light source 490 has been illustrated schematically in FIG. 19 as being an incandescent light source. However, it may be preferred to provide a solid state device as a light source 490. For example, one or more light emitting diodes could be disposed on the leading end portion 52f of the guide rod 50f to function as a light source.

It is contemplated that the electrical energy conducted over the lead 492 to the light source 490 may be varied as the light source moves along the insertion path into the patient's respiratory system. For example, if the light source is pulsed from a maximum light emission level to a minimum light emission level, detection of the location of the leading end portion 52f of the guide rod 50f may be facilitated.

The light source 490 may be detected by suitable photo optic devices, such as photo cells or may be visually detected by the operator of the apparatus associated with the guide rod 50f. When the light source 490 is to be detected by the operator of the positioning apparatus, that is, when the operator is to function as the detector portion of the sensor assembly, it is believed that pulsing the light source will facilitate visual detection of the light source by the operator. It should be understood that both photo electric detection apparatus and visual detection by the operator could be utilized to locate the position of the leading end portion 52f of the guide rod 50f as the guide rod is moved into the patient's respiratory system.

A steering apparatus 460f (FIG. 19) is connected with the leading end portion 52f of the guide rod 50f. The steering apparatus 460f includes a plurality of expandable elements 464f and 466f. Although only two expandable elements 464f and 466f have been illustrated schematically in FIG. 19, it should be understood that a third expandable element, corresponding to the expandable element 468 of FIG. 18, is connected with the leading end portion 52f of the guide rod 50f. The expandable elements are connected with a source of inflation fluid by conduits 472f, 474f and 476f.

When one or more of the expandable elements connected with the leading end portion 52f (FIG. 19) of the guide rod 50f are to be expanded, fluid under pressure is conducted to the expandable elements. For example, when the expandable element 464f is to be operated from a contracted condition to an expanded condition, fluid under pressure, which may be either a gas or liquid, is conducted through the conduit 472f to the expandable element 464f. As the expandable element 464f is operated from a contracted condition to an expanded condition of the influence of fluid pressure, the expandable element applies force against the adjacent body tissues in the patient's respiratory system and applies force against the leading end portion 52f of the guide rod 50f. The force applied against the leading end portion 52f of the guide rod 50f deflects the leading end portion 52f of the guide rod 50f downward (as used in FIG. 19) to maintain the guide rod on the intended path of insertion into the patient's respiratory system. The output from the emitter portion 424f of the sensor assembly enables the operator to determine when it is necessary to expand one or more of the expandable elements and to determine which of the expandable elements to be expanded.

In the embodiment of the invention illustrated in FIG. 19, the emitter on the leading end portion of the guide rod 50f is a light source 490. However, a different type of emitter could be provided if desired. For example, the emitter could be a magnet which cooperates with detectors in the manner previously described in conjunction with FIGS. 15 and 16. Alternatively, the emitter could be a miniaturized radio frequency transmitter.

Figure 20:
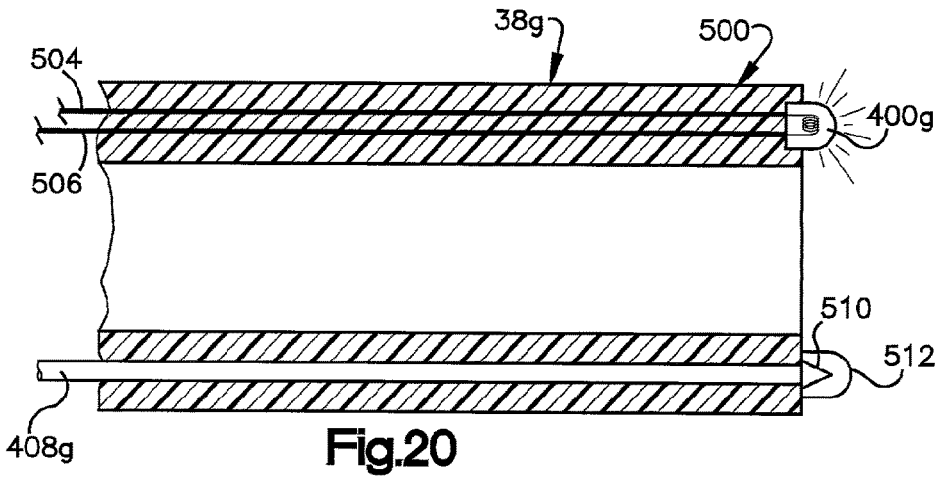
FIG. 20 is an enlarged schematic fragmentary sectional view of a leading end portion of a tracheal tube and illustrating the manner in which a light source and light conductor are disposed on the tracheal tube to facilitate visualization of tissue disposed adjacent to the leading end portion of the tracheal tube.

Embodiment of FIG. 20

In the embodiment of the invention illustrated in FIGS. 13 through 19, sensor assemblies have been illustrated as being associated with a guide rod of a positioning apparatus. In the embodiment of the invention illustrated in FIG. 12, fiber optics are utilized in association with a light source to enable an operator to view images of body tissue immediately ahead of the leading end portion of a guide rod 50*b*. In the embodiment of the invention illustrated in FIG. 20, a light source and fiber optics are associated with a tracheal tube to enable an operator to view images of body tissue immediately ahead of a leading end portion of the tracheal tube during of insertion of the tracheal tube into a patient's respiratory system. Since the embodiment of the invention illustrated in FIG. 20 is generally similar to the embodiments of the invention illustrated in FIGS. 1, 2 and 12, similar numerals will be utilized to designate similar components, the suffix letter "g" being associated with the numerals of FIG. 20 to avoid confusion.

A flexible tracheal tube 38*g* (FIG. 20) has a leading end portion 500. A light source 400*g* is disposed on the leading end portion 500 of the tracheal tube 38*g*. The light source 400*g* is connected with a source of electrical energy by leads 504 and 506. When the tracheal tube 38*g* is moving along an insertion path into a patient's respiratory system, the light source 400*g* illuminates body tissue immediately ahead of the leading end portion 500 of the tracheal tube 38*g*.

In the embodiment of the invention illustrated in FIG. 20, the light source 400*g* is mounted on the leading end portion of the tracheal tube 38*g*. However, it is contemplated that the light source could be disposed at a location remote from the leading end portion 500 of the tracheal tube 38*g* and illumination transmitted from the light source to the leading end portion of the tracheal tube through a fiber optic tube, corresponding to the fiber optic tube 402 of FIG. 12. Of course, a plurality of fiber optic tubes could be utilized if desired.

The light source 400*g* has been illustrated schematically in FIG. 20 as being an incandescent light source. However, it is contemplated that one or more solid state devices, such as light emitting diodes, could form the light source 400*g* if desired. A plurality of light sources 400*g* could be disposed in a circular array on the leading end portion 500 of the tracheal tube 38*g*.

A prismatic lens 510 is also mounted on the leading end portion 500 of the tracheal tube 38*g*. The lens 510 is enclosed by a transparent dome 512 which is connected with the leading end portion 500 of the tracheal tube 38*g*. Light is transmitted from the lens 510 through a fiber optic tube 408*g* to the eye of a viewer or to a display unit associated with a computer. The lens 510 is oriented so that images of body tissue immediately ahead of the leading end portion 500 of the tracheal tube 38*g* are transmitted through the fiber optic tube 408*g*. Although only a single light source 400*g* and single lens 510 have been illustrated schematically in FIG. 20, it should be understood that a plurality of light sources and/or a plurality of lenses may be mounted on the leading end portion 500 of the tracheal tube 38*g*.

The flexible tracheal tube 38*g* may be utilized in association with the positioning apparatus 56 of FIGS. 1 and 2 or with the positioning apparatus 256 of FIG. 4. Alternatively, the tracheal tube 38*g* may be utilized by itself, that is without a positioning apparatus. If the tracheal tube 38*g* is utilized with a positioning apparatus similar to the positioning apparatus 56 or 256, the tracheal tube may be moved along a guide rod similar to the guide rod 50 or the guide rod 250 as the tracheal tube is moved into a patient's respiratory system. However, the tracheal tube may be moved along a guide rod into a patient's respiratory system without utilizing a positioning apparatus, similar to the positioning apparatus 56 or 256 of FIGS. 1 and 4.

The tracheal tube 38*g* may be moved along an insertion path into a patient's respiratory system without benefit of a guide rod. If desired, a steering apparatus, corresponding to the steering apparatus 460 and 460*f* of FIG. 17-19, may be associated with the leading end portion of the tracheal tube 38*g*. Thus, expandable elements, corresponding to the expandable elements 464, 466 and 468 of FIG. 18 may be connected with the leading end portion 500 of the tracheal tube 38*g*. The expandable elements connected with the leading end portion 500 of the tracheal tube 38*g* may be connected in fluid communication with a source of fluid under pressure through conduits disposed in the side wall of the tracheal tube. Since images of body tissue immediately ahead of the leading end portion of the tracheal tube are transmitted through the fiber optic tube 408*g*, an operator who is positioning the tracheal tube relative to a patient's respiratory system will be able to view images of the body tissue and, from these images, be able to determine when to activate one or more expandable elements of a steering apparatus connected with the leading end portion 500 of the tracheal tube 38*g*.

Figure 21:
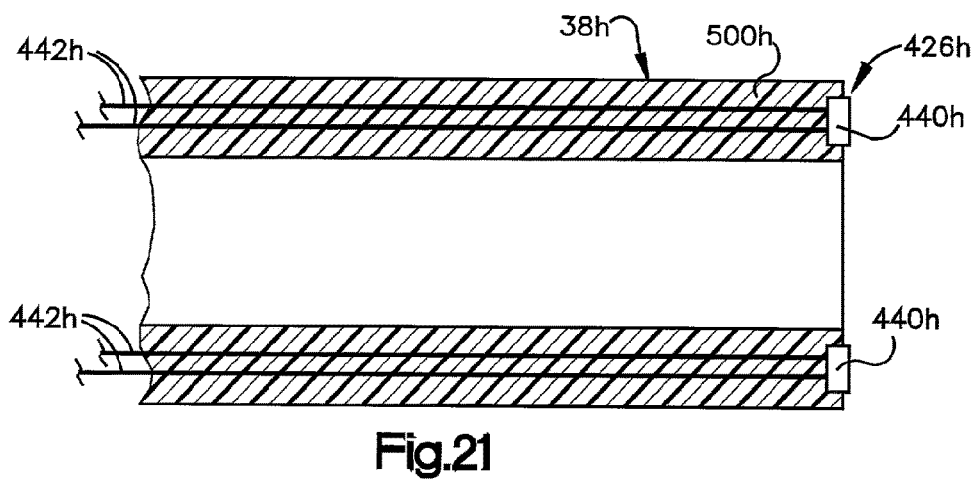
FIG. 21 is an enlarged schematic fragmentary sectional view of a leading end portion of a tracheal tube and illustrating a plurality of detectors which are disposed on the leading end portion of tracheal tube.

Embodiment of FIG. 21

In the embodiment of the invention illustrated in FIG. 20, images of patient's body tissue are transmitted from the leading end portion of the tracheal tube for viewing by an operator who is inserting the tracheal tube into the respiratory system of a patient. In the embodiment of the invention illustrated in FIG. 21, the tracheal tube is associated with a sensor assembly having the same construction as the sensor assembly 420 of FIGS. 13 and 14. Since the embodiment of the invention illustrated in FIG. 21 is generally similar to the embodiment of the invention illustrated in FIGS. 13, 14 and 20, similar numerals will be utilized to designate similar components, the suffix letter "h" being associated with the numerals of FIG. 21 to avoid confusion.

A tracheal tube 38*h* (FIG. 21) has a leading end portion 500*h*. A detector portion 426*h* is provided on the leading end portion 500*h* of the tracheal tube 38*h*. The detector portion 426*h* cooperates with an emitter portion of a sensor assembly having the same construction as the emitter portion 424 (FIG. 14) of the sensor assembly 420.

The tracheal tube 38*h* includes a plurality of magnetic flux sensor units 440*h* which respond to variations in a magnetic flux field in which the sensor units are exposed. In the illustrated embodiment of the invention, the sensor units 440*h* are Hall effect devices. However, the sensor units 440*h* could be other known types of devices which respond to a magnetic flux field The sensors 440*h* are connected with a computer, similar to the computer 438 of FIG. 13, by a plurality of leads 442*h*. The computer to which the leads 442*h* are connected has a display unit which displays an image of a typical respiratory system. The display indicates the position of the leading end portion 500*h* of the tracheal tube 38*h* relative to the patient's respiratory system In addition, the computer display may also indicate the position of a guide rod, corresponding to the guide rod 50*c* of FIG. 13, relative to the patient's respiratory system. Therefore, the computer display shows the position of the leading end portion 500*h* of the tracheal tube 38*h* relative to the leading end portion 52c (FIG. 13) of the guide rod 50c. Although the tracheal tube 38h may advantageously be utilized in association with a guide rod, similar to the guide rod 50c, it is contemplated that the tracheal tube 50h could be utilized by itself without an associated guide rod. Of course, if the tracheal tube 38h was utilized by itself without a guide rod similar to the guide rod 50c of FIG. 13, the output from the computer would indicated the position of the leading end portion 50h of the tracheal tube 38h relative to the patient's respiratory system and would not indicate the location of the guide rod.

It is contemplated that a steering apparatus similar to the steering apparatus 460 of FIG. 17 may be utilized with the tracheal tube 38h (FIG. 21). A plurality of expandable elements, corresponding to the expandable elements 464, 466 and 468 of FIG. 18, would be connected with the leading end portion 50h of the tracheal tube 38h. The cooperation between the Hall effect devices forming the sensor units 440h and the magnets of an associated detector portion of a sensor assembly would enable an operator inserting the tracheal tube 38h into a patient's respiratory system to determine when one or more of the expandable elements should be expanded to steer the leading end portion 500h of the tracheal tube 38h.

Figure 22:
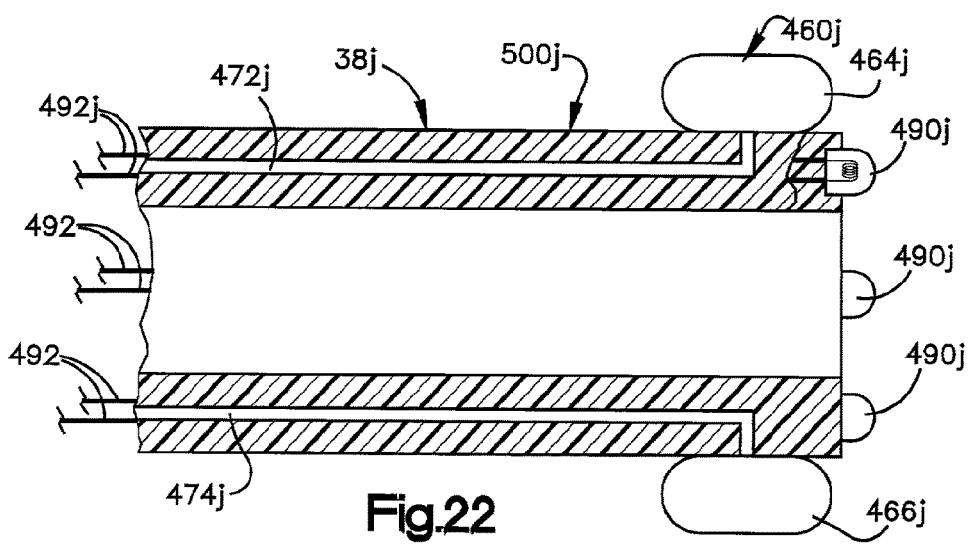
FIG. 22 is an enlarged schematic fragmentary sectional view of a leading end portion of a tracheal tube illustrating the manner in which a plurality of emitters and expandable steering elements are mounted on the leading end portion of the tracheal tube.

Embodiment of FIG. 22

In the embodiment of the invention illustrated in FIG. 19, a light source 490 and steering apparatus 460f is associated with the leading end portion 52f of a guide rod 50f. In the embodiment of the invention illustrated in FIG. 22, a plurality of light sources and a steering apparatus are associated with the leading end portion of a tracheal tube. Since the embodiment of the invention illustrated in FIG. 22 is generally similar to the embodiments of the invention illustrated in FIGS. 19-21, similar numerals will be utilized to designate similar components, the suffix letter "j" being associated with the numerals of FIG. 22 to avoid confusion.

A tracheal tube 38j has a leading end portion 500j. A plurality of light sources 490j are mounted on the leading end portion 500j of the tracheal tube 38j. The light sources 490j are energized by electrical energy connected over leads 492j. Although the light sources 490j have been indicated schematically in FIG. 22 as being incandescent light sources, it is contemplated that solid state devices, such as light emitting diodes, could be utilized as the light sources if desired.

The steering apparatus 460j is mounted on the leading end portion 500j of the tracheal tube 38j. The steering apparatus 460j includes a plurality of expandable elements 464j and 466j. Although only two expandable elements 464j and 466j have been illustrated schematically in FIG. 22, it should be understood that there are three expandable elements connected with the leading end portion 500j of the tracheal tube 38j. The expandable elements are disposed in an array around the end of the tracheal tube in much the same manner as illustrated schematically in FIG. 18 in association with the guide rod 50e The expandable elements 464j and 466j are connected with conduits 472j and 474j. The conduits 472j and 474j are formed in the side wall of the tracheal tube 38j in the manner indicated schematically in FIG. 22. Of course, a third conduit is provided to conduct fluid to and from a third expandable element on the end portion 500j of the tracheal tube 38j. It should be understood that the conduits 472j and 474j could be formed separately from the tracheal tube 38j if desired.

When the steering apparatus 460j is to be utilized to change the course of movement of the leading end portion 500j of the tracheal tube 38j relative to a patient's respiratory system, one or more of the expandable elements in the steering apparatus 460j is inflated under the influence of fluid pressure conducted through an associated conduit. For example, if the expandable element 464j is to be operated from a contracted condition to the expanded condition illustrated schematically in FIG. 22, fluid pressure is connected through the conduit 472j. As the expandable element 464j expands, forces are applied against tissue in the patient's respiratory system by the expandable element 464j. At the same time, the expandable element 464j is effective to apply force against the leading end portion 500j of the tracheal tube 38j to deflect the tracheal tube downward (as viewed in FIG. 22

It is contemplated that the tracheal tube 38j may be utilized in association with a guide rod, such as the guide rod 50f of FIG. 19 or the guide rod 50 of FIG. 1. However, if desired, the tracheal tube 38j could be inserted into a patient's respiratory system without the benefit of a guide rod.

When the tracheal tube 38j is to be inserted into a patient's respiratory system, either with or without a guide rod, the light sources 490j are energized. Energization of the light sources 490j results in the emission of light which can be detected by photo cells or similar devices positioned adjacent to the outside of the patient's neck. If desired, the photo cells could be eliminated and an operator could visually locate the leading end portion 50j of the tracheal tube 38j by viewing the illumination conducted through the patient's body tissues to the surface of the patient's neck. It is contemplated that an operator will, in all probability, locate the leading end portion 500j of the tracheal tube 38j by a combination of the output from photo detectors and visually viewing the patient's neck. If desired, the light sources 490 can be pulsed to provide a variation in the illumination from the light sources to facilitate visual locating of the leading end portion of the tracheal tube 38j by an operator When the inflatable elements 464j and/or 466j are to be operated from the expanded condition illustrated in FIG. 22 to a contracted condition, the conduits 472j and 474j may be exhausted to atmosphere. It is believed that it may be preferred to connect the conduits 472j and 474j with a source of low pressure or suction so that fluid is drawn out of the expandable elements.

As the fluid pressure in the expandable elements 460j and 466j is reduced, the natural resilience of the expandable elements causes them to contract tightly against the leading end portion 500j of the tracheal tube 38j. If desired, a plurality of recesses may be provided in the leading end portion 500j of the tracheal tube 38j to receive the expandable elements 464j and 466j. Of course, if additional expandable elements are associated with the leading end portion 500j of the tracheal tube 38j, additional recesses would be provided to receive these expandable elements when they are contracted.

Various types of emitters and detectors have been illustrated in FIGS. 20, 21 and 22 in association with the tracheal tube 38j. It should be understood that any of the emitters or detector systems previously described in association with a guide rod may be utilized in association with a tracheal tube. For example, a radio frequency transmitter and a receiver may be utilized as the emitter portion and the sensor portion of a sensor assembly which is utilized to detect the location of the leading end portion of a tracheal tube relative to a patient's respiratory system.

Although it is believed that it will probably be preferred to utilize a steering apparatus, similar to the steering apparatus 460*j* in association with the tracheal tube, the steering apparatus could be omitted if desired.

Positioning Apparatus—General—Mode of Operation

The general mode operation of the positioning apparatus 56 of FIG. 1 is illustrated schematically in FIG. 23. As was previously explained, the positioning apparatus 56 includes an arcuate member 108. The arcuate member 108 has a center of curvature indicated at 600 in FIG. 23.

The body section 86 of the positioning apparatus 56 has a central axis which extends through the center 600. The positioning section 96 is connected with an end of the body section 86 which is disposed closest to the center 600 of curvature of the arcuate member 108. The indicia 124 (FIG. 1) on the body section 86 is effective to indicate the length of the body section 86.

The guide rod 50 also has a central axis which extends through the center 600 of curvature of the arcuate section 108. The indicia 142 (FIG. 1) on the guide rod 50 indicates the distance from the leading end portion 52 of the guide rod 50 from the arcuate member 108. The guide rod 50 and body section 86 of the positioning apparatus 56 are both radiuses from the center 600 of curvature of the arcuate member. When the indicia 142 (FIG. 1) indicates that the guide rod 50 (FIG. 23) extends from the arcuate member 108 for the same distance as the body section 86, the leading end portion 52 of the guide rod 50 is aligned with the positioning apparatus 96. Since the positioning apparatus 96 is accurately located relative to the patient's respiratory system 11 (FIG. 1) by engagement with the patient's Adam's apple 34, the position of the leading end portion 52 of the guide rod relative to the patient's larynx 30 is known when the leading end portion 52 of the guide rod 50 is aligned with positioning apparatus 96.

An alternative embodiment of the positioning apparatus 56 is illustrated in FIG. 24. Since the embodiment of the positioning apparatus illustrated in FIG. 24 is generally similar to the embodiment of the positioning apparatus 56 illustrated in FIGS. 1 and 23, similar numerals will be utilized to indicate similar components, the suffix letter "k" being associated with the components of FIG. 24 to avoid confusion.

A positioning apparatus 56*k* includes a body section 86*k*. A positioning section 96*k* is connected with an end portion of the body section 86*k*. The positioning section 96*k* engages the patient's Adam's apple, in the manner previously described in conjunction with the apparatus 56 of FIG. 1.

In the embodiment of the invention illustrated in FIG. 24, a member 108*k* is fixedly connected with the body section 86*k* and extends at a known angle, indicated at 604 in FIG. 24. A guide section 114*k* is disposed at an end of the member 108*k* opposite from the connection 606 with the body section 86*k*. The guide rod section 114*k* guides movement of a guide rod 50*k* along a path which extends through a center 600*k*.

The center 600*k* is disposed at the intersection of a longitudinal central axis of the body section 86*k* and a longitudinal central axis of the guide rod 50*k*. An angle, indicated at 610 in FIG. 24, formed between the longitudinal central axis of the body section 86*k* and the guide rod 50*k* is known. The distance from the positioning section 96*k* to the connection 606 between the body section 86*k* and member 108*k* is known. The angles 604 and 610 are known. The length of the member 108 is also known. Therefore the distance which the guide rod 50*k* must extend from the guide section 114*k* to have the leading end portion 52*k* of the guide rod aligned with the positioning section 96*k* can readily be determined by trigonometric functions.

It should be understood that features of any one embodiment of the invention may be used with features of other embodiments of the invention. For example, the positioning apparatus 256 of FIGS. 4-10 could have the same construction as the positioning apparatus 56 of FIGS. 1-3. Similarly, the magnet 260 of FIG. 4 could be used with the embodiment of the invention illustrated in FIGS. 1-3. The sensor assemblies 420 could be used with either the positioning apparatus 56 of FIG. 1 or the positioning apparatus 256 of FIGS. 4-10. Other combinations of features of the invention will undoubtedly be utilized.

Embodiment of FIGS. 25 and 26

In the embodiments of the invention illustrated in FIGS. 1-24, the positioning apparatus 56 has a positioning section 96 which engages the patient's Adam's apple 34. In the embodiment of the invention illustrated in FIGS. 25 and 26, the positioning apparatus engages a plurality of locations on the patient's neck. Since the embodiment of the invention illustrated in FIGS. 25 and 26 is generally similar to the embodiments of the invention illustrated in FIGS. 1-24, similar numerals will be utilized to designate similar components, the suffix letter "m" being associated with the numerals of FIGS. 25 and 26 to avoid confusion.

A positioning apparatus 56*m* is utilized to position a guide rod 50*m* corresponding to the guide rod 50 of FIG. 1, relative to a patient's trachea 28*m* during insertion of the guide rod into the patient's trachea. In addition, the positioning apparatus 56*m* provides an indication of the distance which the guide rod 50*m* is to be moved into the patient's trachea 28*m*. The positioning apparatus 56*m* includes a base section 78*m* which is connected with an arcuate upper section, corresponding to the arcuate upper section 80 of FIG. 1. The base section 78*m* includes a tubular cylindrical body section 86*m*. The base section 78*m* also includes a positioning section 96*m*. The positioning section 96*m* locates the positioning apparatus 56*m* relative to the patient's Adam's apple 34*m*.

In accordance with a feature of the embodiment of the invention illustrated in FIGS. 25 and 26, the positioning section 96 includes a pair of positioning fingers 622 and 624 which engage the neck 16*m* of the patient at locations disposed on laterally opposite sides of the Adam's apple 34*m*. Thus, the positioning finger 622 is provided with a relatively soft resilient spherical end portion 628 which is pressed against the patient's neck 16*m* at a location adjacent to the left (as viewed in FIG. 26) side of the patient's Adam's apple. Similarly, the positioning finger 624 has a soft resilient spherical end portion 630 which is pressed against the patient's neck 16*m* at a location adjacent to the right (as viewed in FIG. 26) side of the patient's Adam's apple 34*m*. The positioning fingers 622 and 624 cooperate with the patient's Adam's apple 34*m* to locate the positioning section 96*m* laterally relative to the patient's Adam's apple 34*m*.

In the embodiment of the positioning section 96*m* illustrated in FIGS. 25 and 26, the positioning section is provided with a straight center positioning finger 634 which is formed as a continuation of the tubular cylindrical body section 86*m* of the positioning apparatus 56*m*. Thus, the body section 86*m* and center positioning finger 634 are integrally formed as one piece. The center positioning finger 634 has a soft resilient spherical end portion 636 which is pressed against the patient's Adam's apple 34*m* at the center of the patient's Adam's apple.

Force may be applied against the body section 86*m* of the positioning apparatus 56*m* and transmitted to the patient's neck 16*m* to straighten the trachea of the patient. Thus, a slight bend in the trachea can be minimized by the manual application of a relatively small force to the positioning apparatus 56m. This force is transmitted through the end portions 628 and 630 of the positioning fingers 622 and 624 to the patient's neck to straighten the patient's neck. In addition, a portion of the force will be transmitted through the center positioning finger 634 directly to the patient's Adam's apple 34m.

The position of the end portions 628 and 630 of the positioning fingers 622 and 624 relative to the body section 86m of the base section 78m of the positioning apparatus 56m (FIG. 25) can be varied. Thus, the positioning fingers 622 and 624 are fixedly connected to a slide block 640 which is axially movable along the body section 86m. The body section 86m extends through a cylindrical central opening in the slide block 640. A set screw 642 (FIG. 25) having manually engagable wings or flanges can be tightened to hold the positioning fingers 622 and 624 in a desired position relative to the body section 86m of the positioning apparatus 56m. This enables the length of the center positioning finger 634 to be adjusted. By adjusting the length of the center finger 634, a relatively small amount of force can be transmitted through the center finger 634 directly to the patient's Adam's apple 34m and substantially larger forces can be transmitted through the positioning fingers 622 and 624 to the patient's neck 16m to locations disposed on opposite sides of the patient's Adam's apple 34m.

It should be understood that the positioning section 96m of FIGS. 25 and 26 can be utilized in any of the positioning apparatus disclosed in FIGS. 1 through 24 herein. When the positioning section 96m is to be associated with the positioning apparatus 56c of FIG. 13, the emitter units 430 (FIG. 14) could be mounted on or adjacent to the end portions 628, 630 and 636 (FIGS. 25 and 26) of the positioning fingers 622, 624 and 634. Similarly, when the positioning section 96m is utilized in association with the positioning apparatus 56d of FIGS. 15 and 16, the sensor units 440 may be disposed adjacent to and connected with the end portions 628, 630 and 636 (FIG. 25) of the positioning fingers 622, 624 and 634.

Figure 8:
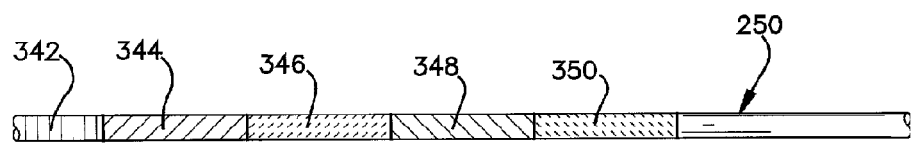
FIG. 8 (on sheet 3 of the drawings) is an enlarged fragmentary schematic illustration of indicia on a portion of the guide rod of FIG. 4.

It should be understood that the positioning apparatus 56m (FIGS. 25 and 26) may be associated with guide rods having the construction of the guide rod 50 of FIG. 1, the guide rod 250 of FIGS. 4 and 8, the guide rod 50e of FIGS. 17 and 18, or the guide rod 50f of FIG. 19. It should also be understood that the positioning apparatus 56m may be associated with a tracheal tube having the construction of any one of the tracheal tubes 38 (FIG. 2), 238 (FIGS. 9 and 10), 38g (FIG. 20), 38h (FIG. 21), or 38j (FIG. 22).

Embodiment of FIGS. 27 and 28

In the embodiment of the invention illustrated in FIGS. 25 and 26, the positioning fingers 622 and 624 are fixedly connected with the body section 86m of the positioning apparatus 56m by the slide block 640 while the positioning fingers 634 is integrally formed as one piece with the body section 36m. In the embodiment of the invention illustrated in FIGS. 27 and 28, the positioning fingers are movable relative to the body section of the positioning apparatus. Since the embodiment of the invention illustrated in FIGS. 27 and 28 is generally similar to the embodiments of the invention illustrated in FIGS. 1-26, similar numerals will be utilized to designate similar components, the suffix letter "r" being associated with the numerals of FIGS. 27 and 28 to avoid confusion.

A positioning apparatus 56r positions a guide rod, corresponding to the guide rod 50 of FIG. 1, relative to a patient's trachea during insertion of the guide rod into the patient's trachea. In addition, the positioning apparatus 56r provides an indication of the distance which the guide rod is to be moved into the patient's trachea. Although only a portion of the positioning apparatus 56r is illustrated in FIGS. 27 and 28, it should be understood that the positioning apparatus may have the same general construction as the positioning apparatus of any one of the embodiments illustrated in FIGS. 1-19.

The positioning apparatus 56r includes a base section 78r which is connected with an arcuate upper section corresponding to the arcuate upper section 80 of FIG. 1. The upper section of the positioning apparatus 56r guides movement of a guide rod, corresponding to the guide rod 50 of FIG. 1, during insertion of the guide rod into the patient's trachea.

In accordance with a feature of the present invention, a positioning section 96r is connected with the base section 78r. The positioning section 96r locates the positioning apparatus 56r relative to the patient's Adam's apple 34r (FIG. 28). The positioning section 96r is connected with an end of a body section 86r of the positioning apparatus 56r by a universal pivot connection 652. The pivot connection 652 allows the orientation of the base section 78r of the positioning apparatus 56r to be changed in any direction relative to the positioning section 96r. Thus, the body section 86r of the positioning apparatus 56r can be raised or lowered (as viewed in FIG. 27) or pivoted to the left or right (as viewed in FIG. 28

The positioning section 96r includes a plurality of positioning fingers 622r, 624r and 634r. The positioning fingers 622r, 624r and 634r are provided with soft resilient spherical end portions 628r, 630r, and 636r. Although the positioning section 96r may be located in any one of many different orientations relative to the patient's Adam's apple 34r, the position section 96r is illustrated in FIG. 28 with the end portions 628r and 630r disposed on laterally opposite sides of the patient's Adam's apple 34r. The end portion 636r is disposed adjacent to the lower end portion of the patient's Adam's apple 34r. If desired, the orientation of the positioning section 96r could be rotated by 180 degrees from the orientation illustrated in FIG. 28. If this was done, the end portion 636r on the positioning finger 634r would be disposed adjacent to the upper portion of the patient's Adam's apple 34r. It is believed that it will probably be preferred to align the pivot connection 652 with the center of the patient's Adam's apple 34r. However, if desired, the pivot connection 652 could be offset from the center of the patient's Adam's apple 34.

In the embodiments of the invention illustrated in FIGS. 25-28, the positioning sections 96m and 96r have been illustrated as having three positioning fingers. However, it is contemplated that the positioning sections could have either a greater number of positioning fingers or a lesser number of positioning fingers if desired. For example, the center positioning finger 634 of the embodiment of the invention illustrated in FIGS. 25 and 26 could be omitted. If this was done, the positioning finger 622 would be positioned on one side of the patient's Adam's apple 34m and the positioning finger 624 would be positioned on the laterally opposite side of the patient's Adam's apple, in the manner illustrated in FIG. 26, without engaging the central portion of the patient's Adam's apple. Alternatively, the positioning section 96m or 96r could be provided with four positioning fingers. If this was done, two of the positioning fingers would be positioned in engagement with the neck of the patient adjacent to one side of the patient's Adam's apple and the other two positioning fingers would be positioned in engagement with the patient's neck on a laterally opposite side of the patient's Adam's apple.

CONCLUSION

An improved method and apparatus for use in tracheal intubination or other medical procedures may include a positioning apparatus 56, 256. When the positioning apparatus 56, 256 is used for tracheal intubation, the positioning apparatus is located relative to a patient's trachea 28, 228 by engaging a portion of the patient's body, such as the Adam's apple 34, 234. A flexible guide rod 50, 250 may be moved relative to the positioning apparatus until a leading end portion 52, 252 of the guide rod has moved into the patient's trachea. A tracheal tube 38, 238 is slid along the guide rod into the patient's trachea.

During movement of the guide rod 50, 250 relative to the positioning apparatus 56, 256, the guide rod may be moved through either a tubular guide member 264 or a tracheal tube 38, 238 which extends through the patient's mouth into the patient's pharynx. Before beginning to move the guide rod 50, 250, the distance which the guide rod is to be moved may advantageously determined. This may be done as a function of spacing between locations on the positioning apparatus 56, 256. If desired, indicia 124, 324 may be provided on the positioning apparatus 56, 256 and cooperating indicia 142, 342-350 may be provided on the guide rod 50, 250.

A magnet 260 may be utilized to attract a leading end portion 252 of the guide rod 250. The magnet 260 is disposed outside of the patient's body and may be positioned adjacent to an anterior side of the trachea. Magnetic attraction between the magnet 260 and the leading end portion 252 of the guide rod deflects the guide rod. This steers the leading end portion of the guide rod 250 into the entrance to the patient's trachea. A magnet may be used to steer a member relative to a patient's body tissue during performance of operations other than tracheal intubation In order to locate the guide rod 50, 250 and/or tracheal tube 38, 238 relative to the patient's trachea, an image of body tissue adjacent to the leading end portion of the guide rod and/or tracheal tube may be transmitted to a location outside of the patient's body (FIGS. 12 and 20). Movement of the guide rod 50, 250 and/or tracheal tube 38, 238 into the patient's trachea is interrupted when the image transmitted from the leading end portion of the guide rod or tracheal tube indicates that the leading end portion of the guide rod or tracheal tube has been moved to a desired position relative to the patient's trachea.

It is believed that transmission of an image of body tissue adjacent to the leading end portion of the tracheal tube 38, 238 may advantageously be performed when the tracheal tube is utilized without benefit of the positioning apparatus 56, 256. However, the transmission of an image of body tissue adjacent to the leading end portion of the tracheal tube 38, 238 may be performed when the positioning apparatus is used in association with the tracheal tube. Positioning of the guide rod 50, 250 relative to the patient's trachea may also be facilitated by the transmitting of images of body tissue adjacent to a leading end portion of the guide rod.

Detectors and emitters 424, 426 may be utilized to detect the position of the leading end portion of the guide rod 50, 250 and/or the tracheal tube 38, 238 relative to the patient's trachea. When this is done, an emitter 424, such as a magnet or a light source, may be connected with a leading end portion 52, 252 of the guide rod 50, 250 and/or the tracheal tube 38, 238. One or more detectors 426 may be provided on the outside of the patient's neck to detect the output from the emitter 424 when the guide rod 50, 250 and/or the tracheal tube 38, 238 are in a desired position relative to the patient's trachea. Alternatively, a detector 426 may be connected with the leading end portion of a guide rod 50, 250 and/or tracheal tube 38, 238 and one or more emitters 424 positioned relative to the outside of the patient's neck. The detector 426 would provide an output indicating when the guide rod 50, 250 and/or tracheal tube 38, 238 is moved to a desired position relative to the patient's trachea.

During movement of the guide rod 50, 250 and/or tracheal tube 38, 238 along the patient's respiratory system and into the patient's trachea, force may be applied against the leading end portion 52, 252 of the guide rod and/or tracheal tube to steer the leading end portion of the guide rod and/or tracheal tube. The application of force against the leading end portion 52, 252 of the guide rod 50, 250 and/or tracheal tube 38, 238 may be accomplished by expanding an expandable element 464-468 connected with the guide rod 50, 250 and/or the tracheal tube 38, 238.

It should be understood that any one of the features of the present invention may be used separately or in combination with other features of the invention. It's believed that various combinations of the features, other than those disclosed herein, may advantageously be utilized and will be apparent to those skilled in the art from the description contained herein. In addition, it should be understood that features of the present invention may be used for purposes other than tracheal intubation. From the above description of the invention, those skilled in the art will perceive improvements, changes and modifications. Such improvements, changes and modifications within the skill of the art are intended to be covered by the appended claims.

What is claimed:

1. A method for positioning a medical device in a respiratory system of a patient, the method comprising:

providing a medical device system including a positioning apparatus configured to enable the insertion of a flexible guide rod into a passage of the patient's respiratory system and a guide tube in which the flexible guide rod is slidably received, the positioning apparatus having a body section and an upper section, the body section having a cylindrical central passage, the upper section slidably coupled to the body section such that the upper section slidably moves relative to the body section, and the upper section having a cylindrical passage, such that at least a portion of the cylindrical passage of the upper section and a portion of the cylindrical passage of the body section are parallel, the flexible guide rod having a distal end, a visible light source operatively connected to the flexible guide rod such that visible light from the visible light source can be emitted outward from adjacent the distal end of the flexible guide rod, and a medical device for treating the patient slidably receivable on the flexible guide rod;

inserting the flexible guide rod and the guide tube together along a first respiratory system passage of the patient's respiratory system until a distal end of the flexible guide rod is located at a first rod location adjacent an opening to a second respiratory system passage of the patient's respiratory system extending transverse to the first respiratory system passage and an open distal end of the guide tube is located at a first tube location adjacent the opening to the second respiratory system passage;

maintaining the guide tube in position so that the distal end of the guide tube is located generally at the first tube location;

while performing the step of maintaining the guide tube in position, advancing the flexible guide rod through the guide tube so that the distal end of the flexible guide rod moves in a distal direction relative to the open distal end of the guide tube from the first rod location, to a second rod location in the second respiratory system passage;

emitting visible light from the visible light source outward from adjacent the distal end of the flexible guide rod while performing the step of advancing the flexible guide rod such that the emitted visible light is transmitted outward from within the patient's respiratory system and through the patient's body as the flexible guide rod is advanced;

visually observing, outside the patient's body, the emitted visible light that is transmitted outward through the patient's body to determine the location of the distal end of the flexible guide rod as the flexible guide rod is advanced; and slidably moving, after said performing the step of visually observing the emitted visible light that is transmitted outward through the patient's body, the medical device distally along the flexible guide rod toward the distal end of the flexible guide rod to a selected position relative to the distal end of the flexible guide rod and within the second respiratory system passage.

2. The method for positioning a medical device in a respiratory system of a patient as set forth in claim 1, wherein the step of inserting the flexible guide rod and the guide tube together comprises inserting the flexible guide rod and the guide tube together into a body orifice of the patient's body in communication with the first respiratory system passage, wherein a distal end section of the guide tube encompassing the open distal end of the guide tube has an arcuate shape such that the guide tube extends from adjacent the body orifice to the open distal end of the guide tube and the open distal end of the guide tube generally faces the opening to the second respiratory system passage after performing the step of inserting the flexible guide rod and the flexible guide tube together.

3. The method for positioning a medical device in a respiratory system of a patient as set forth in claim 2, wherein the step of advancing the flexible guide rod through the guide tube includes bending a section of the flexible guide rod into an arcuate shape corresponding to the arcuate shape of the distal end section of the guide tube as the section of the flexible guide rod moves along the distal end section of the guide tube.

4. The method for positioning a medical device in a respiratory system of a patient as set forth in claim 1, wherein both the guide tube and the positioning apparatus have at least one matching colored indicium.

5. The method for positioning a medical device in a respiratory system of a patient as set forth in claim 1, wherein the flexible guide rod comprises an optical fiber having a distal end adjacent the distal end of the flexible guide rod, and a proximal end configured to remain outside the patient's body during said method for positioning a medical device, wherein the visible light source is adjacent the proximal end of the optical fiber, wherein said emitting visible light from the visible light source comprises transmitting visible light from the visible light source located outside the body through the optical fiber of the flexible guide rod.

6. The method for positioning a medical device in a respiratory system of a patient as set forth in claim 1, wherein the flexible guide rod includes a plurality of markers spaced predetermined distances from the distal end of the flexible guide rod, the method further comprising:

visibly observing, after said inserting the flexible guide rod, one or more of the markers outside the patient to determine a position of the distal end of the flexible guide rod in the treatment portion of the respiratory system of the patient's body.

7. The method for positioning a medical device in a respiratory system of a patient as set forth in claim 1, further comprising:

endoscopically observing the flexible guide rod in the respiratory system of the patient's body during said inserting the flexible guide rod.

8. The method for positioning a medical device in a respiratory system of a patient as set forth in claim 1, wherein the opening to the second respiratory system passage is formed in a wall of the first respiratory system passage.

9. The method for positioning a medical device in a respiratory system of a patient as set forth in claim 1, wherein the step of advancing the flexible guide rod relative through the guide tube comprises moving the distal end of the flexible guide rod in an inferior direction of the patient.

10. The method for positioning a medical device in a respiratory system of a patient as set forth in claim 9, wherein the step of moving the distal end of the flexible guide rod in the inferior direction comprises moving the distal end of the flexible guide rod in the inferior direction along the second respiratory system passage.

11. The method for positioning a medical device in a respiratory system of a patient as set forth in claim 1, wherein the upper section of the positioning apparatus comprises a single piece of monolithic material that extends seamlessly about the cylindrical passage of the upper section.

12. The method for positioning a medical device in a respiratory system of a patient as set forth in claim 1, wherein the cylindrical passage of the upper section of the positioning apparatus has a length and the cylindrical central passage of the body section of the positioning apparatus has a length that is greater than the length of the cylindrical passage of the upper section of the positioning apparatus.

13. The method for positioning a medical device in a respiratory system of a patient as set forth in claim 1, wherein the body section of the positioning apparatus has a length extending parallel to a longitudinal axis of the central cylindrical passage extending therethrough and the upper section of the positioning apparatus has a length extending parallel to the length of the body section, wherein the length of the body section is greater than the length of the upper section.

14. A method for positioning a medical device in a respiratory system of a patient, the method comprising:

providing a medical device system including a positioning apparatus configured to enable the insertion of a flexible guide rod into a passage of a respiratory system of the patient and a guide tube in which the flexible guide rod is slidably received, the positioning apparatus having a body section and an upper section, the body section having a cylindrical central passage, the upper section slidably coupled to the body section such that the upper section slidably moves relative to the body section, and the upper section having a cylindrical passage, such that at least a portion of the cylindrical passage of the upper section and a portion of the cylindrical passage of the body section are parallel, a visible light source operatively connected to the flexible guide rod such that visible light from the visible light source can be emitted outward from adjacent the distal end of the flexible guide rod, wherein the flexible guide rod is slidably receivable in the guide tube;

inserting the flexible guide rod and the guide tube together into a body orifice of the patient's body and then along a first respiratory system passage of the respiratory system of the patient's body until a distal end of the flexible guide rod and an open distal end of the guide tube are located adjacent an opening to a second respiratory system passage of the respiratory system extending transversely to the first respiratory system passage, wherein a distal end section of the guide tube encompassing the open distal end of the guide tube has an arcuate shape such that the guide tube extends from adjacent the body orifice to the open distal end of the guide tube and the open distal end of the guide tube generally faces the opening to the second respiratory system passage after performing the step of inserting the flexible guide rod and the flexible guide tube together;

after performing the step of inserting the flexible guide rod and the guide tube together until the distal end of the flexible guide rod and the open distal end of the guide tube are located adjacent the opening to the second respiratory system passage, advancing the flexible guide rod relative to the guide tube in a distal direction such that the distal end of the flexible guide rod moves distally away from the open distal end of the guide tube and into the second respiratory system passage, wherein the step of advancing the flexible guide rod relative to the guide tube includes bending a section of the flexible guide rod into an arcuate shape corresponding to the arcuate shape of the distal end section of the guide tube as the section of the flexible guide rod moves along the distal end section of the guide tube;

emitting visible light from the visible light source outward from adjacent the distal end of the flexible guide rod such that the emitted visible light is transmitted from within the second respiratory system passage and outward through the patient's body;

visually observing, outside the patient's body, the emitted visible light that is transmitted from within the second respiratory system passage and outward through the patient's body to determine the location of the distal end of the flexible guide rod within said treatment portion of the respiratory system of the patient's body;

wherein the medical device system further includes an inflatable balloon slidably movable relative to the guide tube, the method further comprising:

after performing the step of inserting the flexible guide rod and the guide tube together, slidably moving the inflatable balloon distally relative to the guide tube such that the inflatable balloon moves distally into to the second respiratory system passage; and after the step of slidably moving the inflatable balloon, inflating the inflatable balloon to apply a force against body tissue in the respiratory system of the patient's body.

15. The method for positioning a medical device in a respiratory system of a patient as set forth in claim 14, wherein the opening to the second respiratory system passage is formed in a wall of the first respiratory system passage.

16. The method for positioning a medical device in a respiratory system of a patient as set forth in claim 14, wherein the step of advancing the flexible guide rod relative to the guide tube comprises moving the distal end of the flexible guide rod in an inferior direction of the patient.

17. The method for positioning a medical device in a respiratory system of a patient as set forth in claim 16, wherein the step of moving the distal end of the flexible guide rod in the inferior direction comprises moving the distal end of the flexible guide rod in the inferior direction along the second respiratory system passage.

18. The method for positioning a medical device in a respiratory system of a patient as set forth in claim 14, wherein the upper section of the positioning apparatus comprises a single piece of monolithic material that extends seamlessly about the cylindrical passage of the upper section.

19. The method for positioning a medical device in a respiratory system of a patient as set forth in claim 14, wherein the cylindrical passage of the upper section of the positioning apparatus has a length and the cylindrical central passage of the body section of the positioning apparatus has a length that is greater than the length of the cylindrical passage of the upper section of the positioning apparatus.

20. The method for positioning a medical device in a respiratory system of a patient as set forth in claim 14, wherein the body section of the positioning apparatus has a length extending parallel to a longitudinal axis of the central cylindrical passage extending therethrough and the upper section of the positioning apparatus has a length extending parallel to the length of the body section, wherein the length of the body section is greater than the length of the upper section.

* * * * *